(12) United States Patent
Ge

(10) Patent No.: US 8,969,584 B2
(45) Date of Patent: Mar. 3, 2015

(54) PIM KINASE INHIBITORS AND PREPARATION METHODS AND USE IN MEDICINAL MANUFACTURE THEREOF

(71) Applicant: Yu Ge, Shanghai (CN)

(72) Inventor: Yu Ge, Shanghai (CN)

(73) Assignee: Jikai Biosciences, Inc., Shanghai (CN)

( * ) Notice: Subject to any disclaimer, the term of this patent is extended or adjusted under 35 U.S.C. 154(b) by 0 days.

(21) Appl. No.: 14/177,131

(22) Filed: Feb. 10, 2014

(65) Prior Publication Data

US 2014/0162998 A1 Jun. 12, 2014

Related U.S. Application Data

(63) Continuation of application No. PCT/CN2012/001061, filed on Aug. 8, 2012.

(30) Foreign Application Priority Data

Aug. 11, 2011 (CN) .......................... 2011 1 0229731
Aug. 1, 2012 (CN) .......................... 2012 1 0271445

(51) Int. Cl.
| | | |
|---|---|---|
| C07D 417/00 | (2006.01) |
| C07D 403/14 | (2006.01) |
| C07D 417/12 | (2006.01) |
| C07D 417/14 | (2006.01) |
| A61K 31/4439 | (2006.01) |
| A61K 31/4545 | (2006.01) |
| C07D 471/08 | (2006.01) |
| C07D 405/14 | (2006.01) |
| C07D 451/02 | (2006.01) |
| C07D 453/02 | (2006.01) |

(52) U.S. Cl.
CPC ............ *C07D 403/14* (2013.01); *C07D 417/12* (2013.01); *C07D 417/14* (2013.01); *A61K 31/4439* (2013.01); *A61K 31/4545* (2013.01); *C07D 471/08* (2013.01); *C07D 405/14* (2013.01); *C07D 451/02* (2013.01); *C07D 453/02* (2013.01)
USPC ......................................................... 548/214

(58) Field of Classification Search
USPC ......................................................... 548/214
See application file for complete search history.

(56) References Cited

U.S. PATENT DOCUMENTS

| 4,332,809 A | 6/1982 | Honma et al. |
| 4,879,295 A | 11/1989 | Yoshinaga et al. |
| 2011/0044940 A1 | 2/2011 | Shipps, Jr. et al. |

FOREIGN PATENT DOCUMENTS

| WO | WO 2008/106692 A1 | 9/2008 |
| WO | WO 2008/141976 A1 | 11/2008 |
| WO | WO 2010/078408 A1 | 7/2010 |

OTHER PUBLICATIONS

Copending U.S. Appl. No. 14/177,156, filed Feb. 10, 2014, Ge, Yu.
Marius Vantler et al., "Systematic Evaluation of Anti-Apoptotic Growth Factor Signaling in Vascular Smooth Muscle Cells," The Journal of Biological Chemistry, vol. 280, No. 14, pp. 14168-14176 (Issue of Apr. 8, 2005).
Peter S. Hammerman et al., "Pim and Akt oncogenes are independent regulators of hemotopoietic cell growth and survival," Blood, vol. 105, No. 11, pp. 4477-4483 (Jun. 1, 2005).
Casey J. Fox et al., "The Pim kinases control rapamycin-resistant T cell survival and activation," The Journal of Experimental Medicine, vol. 201, No. 2, pp. 259-266 (Juanuary 17, 2005).
D.A. Fruman, "Towards an understanding of isoform specificity in phosphoinositide 3-kinase signalling in lymphocytes," Biochem. Soc. Trans. vol. 32, pp. 315-319 (2004).
H. Theo Cuypers et al., "Murine leukemia virus-induced T-cell lymphomagenesis: integration of proviruses in a distrinct chromosomal region," Cell, vol. 37, pp. 141-150 (May 1984).
Beth Levine et al., "Autophagy in cell death: an innocent convict?" The Journal of Clinical Investigation, vol. 115, No. 10, pp. 2679-2688 (Oct. 2005).
Nathalie M. T. Van Der Lugt et al., "Proviral tagging in Eµ-*myc* transgenic mice lacking the *Pim-1* proto-oncogene leads to compensatory activation of *Pim-2*," The EMBO Journal, vol. 14, No. 11, pp. 2536-2544 (1995).

(Continued)

*Primary Examiner* — Nizal Chandrakumar
(74) *Attorney, Agent, or Firm* — Manni Li; Mei & Mark LLP

(57) ABSTRACT

A Pim kinase inhibitor compound having the structure represented by Formula I, and isomers, diastereomers, enantiomers, tautomers, and pharmaceutically acceptable salts thereof. The compounds significantly inhibit Pim kinase activity and can be used to prepare drugs for treating Pim kinase mediated diseases, such as cancers, autoimmune diseases, allergic reactions, or organ transplant rejection. Also provided are methods for preparing the compounds represented by Formula I.

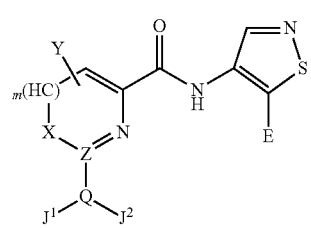

I

11 Claims, No Drawings

(56) References Cited

OTHER PUBLICATIONS

Hans-Guido Wendel et al., "Survival signalling by Akt and eIF4E in oncogenesis and cancer therapy," Nature, 428, pp. 332-337 (Mar. 18, 2004).

Maarten Van Lohuizen et al., "Predisposition to lymphomagenesis in *pim*-1 transgenic mice: Cooperation with c-*myc* and N-*myc* in murine leukemia virus-induced tumors," Cell 56, Issue 4, pp. 673-682 (Feb. 24, 1989).

Robert Amson et al., "The human protooncogene product p33pim is expressed during fetal hematopoiesis and in diverse leukemias," Proc. Natl. Acad. Sci. USA, vol. 86, pp. 8857-8861 (Nov. 1989).

T.L. Cibull et al., "Overexpression of Pim-1 during progression of prostatic adenocarcinoma," J. Clin. Pathol., vol. 59, pp. 285-288 (2006).

Amos M. Cohen et al., "Increased Expression of the hPim-2 gene in human chronic lymphocytic leukemia and non-Hodgkin lymphoma," Leuk. Lymph., 45, pp. 951-955 (2004).

Chifumi Fujii et al., "Aberrant expression of serine/threonine kinase Pim-3 in hepatocellular carcinoma development and its role in the proliferation of human hepatoma cell lines," Int. J. Cancer, vol. 114, pp. 209-218 (2005).

Ying-Yi Li et al., "Pim-3, a proto-oncogene with serine/threonine kinase activity, is aberrantly expressed in human pancreatic cancer and phosphorylates bad to block bad-mediated apoptosis in human pancreatic cancer cell lines," Cancer Res., vol. 66, pp. 6741-6747 (Jul. 1, 2006).

Teija L.T. Aho et al., "Pim-1 kinase promotes inactivation of the pro-apoptotic bad protein by phosphorylating it on the $Ser^{112}$ gatekeeper site," FEBS Letters, vol. 571, pp. 43-49 (2004).

Zeping Wang et al., "Phosphorylation of the cell cycle inhibitor $p21^{Cip1/WAF1}$ by Pim-1 kinase," Biochem. Biophys. Acta, vol. 1593, pp. 45-55 (2002).

Malte Bachmann et al., "The oncogenic serine/threonine kinase Pim-1 phosphorylates and inhibits the activity of Cdc25C-associated kinase 1 (C-TAK1)," The Journal of Biological Chemistry, vol. 279, No. 46, pp. 48319-48328 (Issue of Nov. 12, 2004).

Teija L. T. Aho et al., "Expression of human *pim* family genes is selectively up-regulated by cytokines promoting T helper type 1, but not T helper type 2, cell differentiation," Immunology, vol. 116, pp. 82-88 (2005).

PIM KINASE INHIBITORS AND PREPARATION METHODS AND USE IN MEDICINAL MANUFACTURE THEREOF

CROSS-REFERENCE AND RELATED APPLICATIONS

The subject application is a continuation of PCT international application PCT/CN2012/001061 filed on Aug. 8, 2012, which in turn claims priority on Chinese patent applications CN 201110229731.X filed on Aug. 11, 2011 and CN 201210271445.4 filed on Aug. 1, 2012. The contents and subject matter of the PCT and Chinese priority applications are incorporated herein by reference.

TECHNICAL FIELD

The present invention relates to medicinal chemistry, particularly PIM kinase inhibitors, methods of preparation, and their pharmaceutical application in treating diseases.

BACKGROUND

PIM kinase family consists of three homologous serine/threonine kinases, Pim-1, Pim-2, and Pim-3, which belong to calmodulin-dependent protein kinase-related family (CAMK). Researches have shown that PIM kinases are widely expressed in hematopoietic tissues (J. Biol. Chem., 280, 14168-14176, 2005; Blood, 105, 4477-4483, 2005) and play important roles in cell survival and proliferation. Since PIM kinases are overexpressed in a variety of malignancies and inflammations (J. Exp. Med., 201, 259-266, 2005; Biochem. Soc. Trans., 32, 315-319, 2004), they are more and more being targeted for treating cancers and immune dysfunctions. PIM-1 (Provirus Integration of Maloney 1) was originally identified in a series of insertional mutagenesis studies of retroviruses, as a frequent proviral integration site in Moloney murine leukemia virus-induced T-cell lymphomas, and PIM-1 was named based on that finding (Cell, 37, 141-150, 1984). It was found later that the genes encoding PIM-2 (Provirus Integration of Maloney 2) have the same defect (J. Clin. Invest., 115, 2679-2688, 2005). Pim-2 has similar effects as and compensatory to Pim-1 (J EMBO, 14, 2536, 1995). PIM-3 was initially named as KID-1 (Kinase Induced by Depolarization 1), but renamed to Pim-3 because of its high sequence similarity to Pim-1 (Nature, 428, 332-337, 2005; Cell, 56, 673-682, 1989). PIM-1, 2, 3 are overly expressed in many hematopoietic malignancies (PNAS USA, 86, 8857-8861, 1989). PIM-1 was found to be overexpressed in the development of prostate cancer (J. Clin. Pathol., 59, 285-288, 2006). PIM-2 expression is elevated in human chronic lymphocytic leukemia and non-Hodgkin's lymphoma leukemia (Leuk. Lymph., 45, 951-955, 2004), the aberrant expression of PIM-3 is believed to have played an important role in the development and proliferation of live fibroma (Int. J. Cancer, 114, 209-218, 2005) and pancreatic cancer (Cancer Res., 66, 6741-6747, 2006).

PIM-1, 2, 3 have effects on the survival and proliferation of hematopoietic cells in response to growth factors stimulation. PIM-1, 2, 3 triple knockout mice are viable and fertile while displaying reduced body size and impairment of proliferation of hematopoietic cells in response to growth factors. Knocking out one of 3 kinases does not have obvious effect on mice, indicating some overlapping functions among PIM kinases (Cell, 56, 673-682, 1989). The substrates of PIM kinases include Bcl-2 family members such as pro-apoptotic BAD protein (FEBS Letters, 571, 43-49, 2004), cell cycle regulating p21 (Biochim Biophys. Acta, 1593, 45-55, 2002), CDC25A, C-TA (J. Biol. Chem., 279, 48319-48328, 2004), protein synthesis related 4EBP1 (Blood, 105, 4477-4483, 2005). These functions of PIM kinases indicate that PIM kinases can prevent apoptosis and promote cell growth and proliferation. Their overexpression in cancer cells promotes the survival and proliferation of the cancer cells. Therefore, inhibiting the PIM kinase activities in cancer cell is a new effective way of treating cancers. Besides cancer, PIM inhibitors can also be used to treat autoimmune diseases, allergic reactions, and organ transplant rejection (Immunology, 116, 82-88, 2005).

SUMMARY OF THE INVENTION

The present invention provides chemical compounds having certain biological activities that include, but not limited to, inhibiting cell proliferation, promoting apoptosis, and modulating protein kinase activities. The present invention provides compounds that inhibit the activities of PIM-1, PIM-2 and PIM-3 kinases. The present invention also provides methods for preparing novel chemical compounds, and analogs thereof, and methods of using these compounds to treat cancers, autoimmune diseases, allergic reactions, and organ transplant rejection.

The PIM kinase inhibitors of the present invention have the following general structural formula I, and their isomers, diastereomers, enantiomers, tautomers, and pharmaceutically acceptable salts,

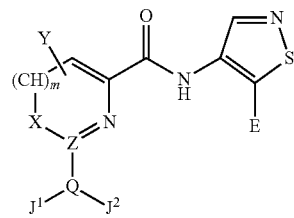

Wherein,
E, $J^1$, $J^2$, Q, X, Y, Z, m of Formula I are:
When m is 0, X is S, O, N or CH;
When m is 1, X is CH or N;
Z is CH or N;
Y is H or $N(R^1R^2)$, each of $R^1$, $R^2$ is independently selected from H or optionally substituted $C_1$-$C_8$ hydrocarbon group; or
Y is H or $N(R^1C(=O)R^2)$, each of $R^1$, $R^2$ is independently selected from H or optionally substituted $C_1$-$C_8$ hydrocarbon group;
E is $N(R^3R^4)$, each of $R^3$, $R^4$ is independently selected from optionally substituted $C_1$-$C_8$ hydrocarbon group; or
E is

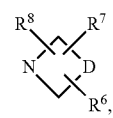

Wherein,
D is a linear chain of 1-5 $CH_2$; or
D is a linear chain containing 1 O atom or $NR^5$ group and the rest is 1-5 $CH_2$; $R^5$ is H or optionally substituted $C_1$-$C_8$ hydrocarbon group;

$R^6$, $R^7$, $R^8$ is independently selected from H, halo, $OR^9$, $NR^{10}R^{11}$ or optionally substituted $C_1$-$C_8$ hydrocarbon group; wherein $R^9$, $R^{10}$, $R^{11}$ is independently selected from H or optionally substituted $C_1$-$C_8$ hydrocarbon group; or $R^6$, $R^7$, $R^8$ are joined together to form a chain so that the ring to which they are attached is an optionally substituted $C_6$-$C_{14}$ membered spiral ring, bicyclic ring or fused ring group; or E is substituted phenyl group

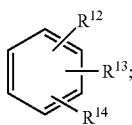

Wherein,
$R^{12}R^{13}$, $R^{14}$ is independently selected from H, halo, $OR^{15}$, $NR^{16}R^{17}$, $C(=O)NR^{18}R^{19}$ or optionally substituted $C_1$-$C_8$ hydrocarbon group; or E is 5 or 6 membered hetero aromatic group containing 1 or 2 hetero atoms such as

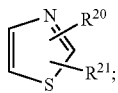

$R^{20}$, $R^{20}$ is independently selected from H, halo, $OR^{15}$, $NR^{16}R^{17}$, $C(=O)NR^{18}R^{19}$ or optionally substituted $C_1$-$C_8$ hydrocarbon group;
$R^{15}$, $R^{16}$, $R^{17}$, $R^{18}$, $R^{19}$ is independently selected from H or optionally substituted $C_1$-$C_8$ hydrocarbon group;
E is $OR^{22}$;
Wherein,
$R^{22}$ is optionally substituted $C_1$-$C_8$ hydrocarbon group; or
$R^{22}$ is a group described in the following formula:

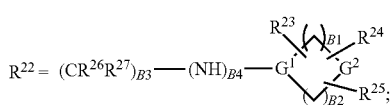

Wherein,
Each of $R^{23}$, $R^{24}$, $R^{25}$ is independently selected from H, halo, $OR^{15}$, $NR^{16}R^{17}$, $C(=O)NR^{18}R^{19}$ or optionally substituted $C_1$-$C_8$ hydrocarbon group; or $R^{23}$, $R^{24}$ and $R^{25}$, together with the atoms to which they are attached, may be joined together to form a chain so that the ring to which they are attached is a substituted $C_6$-$C_{14}$ membered spiral ring, bicyclic ring or fused ring group;
$G^1$ is CH or N;
$G^2$ is $NR^{28}$, $CHR^{29}$ or O;
B1 and B2 each independently represents 0, 1, 2 or 3;
B3 is 0, 1 or 2;
B4 is 0, 1;
Each of $R^{26}$ and $R^{27}$ is independently selected from H or optionally substituted $C_1$-$C_8$ hydrocarbon group;
$R^{28}$ is H, optionally substituted hydrocarbon group, optionally substituted cyclic hydrocarbon group, optionally substituted heterocyclic hydrocarbon group, $C(=O)R^{30}$, $C(=O)OR^{30}$ or $C(=O)NHR^{30}$;
$R^{29}$ is OH, $NHR^{30}$, $C(=O)OR^{30}$ or $C(=O)NHR^{30}$;
$R^{30}$ is H or optionally substituted $C_1$-$C_8$ hydrocarbon group;
Q is C, CH or N;

$J^1$, $J^2$ is independently selected from H or optionally substituted $C_1$-$C_8$ hydrocarbon group, $OR^{31}$, $NHR^{31}$ or $C(=O)R^{31}$; or $J^1$, $J^2$ together with CH they are attached, are joined together to form a $C_3$-$C_8$ membered cycloalkyl; or $J^1$, $J^2$ together with the atoms to which they are attached and at least one hetero atom to form $C_4$-$C_7$ membered heterocycloalkyl; on such $C_3$-$C_8$ membered cycloalkyl and $C_4$-$C_7$ membered heterocycloalkyl, one or more position can be optionally substituted with halo, $OR^{32}$, $NHR^{33}$ or optionally substituted $C_1$-$C_8$ hydrocarbon group, or such substituents are joined together to form a chain so that the ring to which they are attached is a substituted $C_6$-$C_{14}$ membered spiral ring, bicyclic ring or fused ring group; or $J^1$, $J^2$ together with C atom they are attached, are joined together to form aromatic rings, such as benzene ring and naphthlene, or $J^1$, $J^2$ together with C they are attached and at least one heteroatom, are joined together to form $C_5$-$C_6$ membered aromatic heterocycles, such as pyridine, pyrimidine, pyrazine, imidazole, thiazole, isoxazole, oxazole or pyrrole, on the aromatic rings and hetero aromatic rings, one or more position can be optionally substituted with halo, CN, $OR^{32}$, $NHR^{33}$ or optionally substituted $C_1$-$C_8$ hydrocarbon group, or such substituents are joined together to form a chain so that the ring to which they are attached is an optionally substituted $C_6$-$C_{14}$ membered aromatic spiral ring, bicyclic ring or fused ring group; or $J^1$, $J^2$ together with N atom they are attached, are joined together to form $C_4$-$C_7$ membered heterocycloalkyl group, or $J^1$, $J^2$ together with N atom they are attached, and at least one hetero atom, are joined together to form $C_4$-$C_7$ membered heterocycloalkyl group; on these $C_4$-$C_7$ membered heterocycloalkyl group, one or more position can be optionally substituted with halo, CN, $OR^{32}$, $NHR^{33}$ or optionally substituted $C_1$-$C_8$ hydrocarbon group, or such substituents are joined together to form a chain so that the ring to which they are attached is an optionally substituted $C_6$-$C_{14}$ membered aromatic spiral ring, bicyclic ring or fused ring group;

$R^{31}$ is H or optionally substituted $C_1$-$C_8$ hydrocarbon group;
Each of $R^{32}$, $R^{33}$ is independently selected from H or optionally substituted $C_1$-$C_8$ hydrocarbon group, optionally substituted $C_3$-$C_8$ cyclic hydrocarbon group, optionally substituted $C_4$-$C_7$ membered heterocyclic hydrocarbon group, $C(=O)R^{34}$, $C(=O)OR^{34}$ or $C(=O)NHR^{34}$;
$R^{34}$ is H or optionally substituted $C_1$-$C_8$ hydrocarbon group.

DETAILED DESCRIPTION OF THE INVENTION

As used herein, the term 'subtituent' refers to atom or atomic group that replaces the hydrogen atoms of the molecule. As used herein, 'optionally substituted' substituent refers to substituents that each of the replacible hydrogen atoms on the substituents may be substituted by other atom or atomic group.

As used herein, the term 'hydrocarbon group' refers to alkyl group (saturated aliphatic group), alkenyl group (having at least one carbon-carbon double bond), alkynyl group (having at least one carbon-carbon triple bond); The 'hydrocarbon group' may be linear, branced or cyclic; the 'hydrocarbon group' may be aliphatic or aromatic.

As used herein, the term 'cyclic hydrocarbon group' refers to cycloalkyl group or cycloalkenyl group (having at least one carbon-carbon double bond), aromatic group; 'cyclic hydrocarbon group' may be monocyclic, bicyclic or multi-cyclic group; 'cyclic hydrocarbon group' may be spiral or fused ring.

As used herein, the term 'hetero cyclic hydrocarbon group' refers to cycloalkyl group or cycloalkenyl group (having at least one carbon-carbon double bond), aromatic group with one or more ring atoms are hetero atoms such as N, O, S, or combination thereof; 'hetero cyclic hydrocarbon group' may be monocyclic, bicyclic or multi-cyclic group; 'hetero cyclic hydrocarbon group' may be spiral or fused ring.

As used herein, the term 'substituent' include but not limited to: halo (F, Cl, Br, I), —$OR^{26}$, —$OC(=O)R^{26}$, —$OC(=O)NR^{26}R^{27}$, =O, —$S_R^{26}$, —$SOR^{26}$, —$SO_2R^{26}$, —$SO_2NR^{26}R^{27}$, —$C(=O)R^{26}$, —$C(=O)OR^{26}$, —$C(=O)NR^{26}R^{27}$, —$R^{26}CN$, —$NR^{26}R^{27}$, —$NHC(=O)R^{26}$, —$NHC(=O)NR^{26}R^{27}$, —$NHC(=S)NR^{26}R^{27}$, halogenated (F, Cl, Br, I) hydrocarbon;

Wherein,

Each of $R^{26}$ and $R^{27}$ is independently selected from H or optionally substituted $C_1$-$C_8$ hydrocarbon group.

The compounds described in the present invention that are acidic in nature can form pharmaceutically acceptable salts by reacting with physiologically compatible organic or inorganic bases, such as readily soluble alkali and alkaline earth salts, and salts formed from reacting with ammonia, N-methyl-glucamine, dimethyl-glucamine, ethyl-glucamine, lysine, ethanolamine, glucosamine, sarcosine, serine, tris(hydroxymethyl)aminomethane, 1-amino-2,3,4-butanetriol The compounds described in the present invention that are basic in nature can form pharmaceutically acceptable salts by reacting with physiologically compatible organic or inorganic acids, such as the salts formed by reacting with hydrochloric acid, hydrobromic acid, sulfuric acid, phosphoric acid, methanesulfonic acid, toluenesulfonic acid, carbonic acid, succinic acid, citric acid, benzoic acid, oxalic acid, malonic acid, salicylic acid, malic acid, fumaric acid, maleic acid, acetic acid, ascorbic acid.

The compounds in the present invention may be pure chiral compounds, racemic mixtures, optically active compounds, pure diastereomers, or mixed diastereomers The present invention provides PIM kinase inhibitors which include the following compounds:

5-amino-2-(2,6-difluorophenyl)-N-(5-(piperidin-4-yloxy)isothiazol-4-yl)thiazole-4-carboxamide (1)
N-(5-(azepan-4-yloxy)isothiazol-4-yl)-2-(2,6-difluorophenyl)thiazole-4-carboxamide (2)
N-(5-(4-carbamoylphenyl)isothiazol-4-yl)-2-(2,6-difluorophenyl)thiazole-4-carboxamide (3)
N-(5-(4-carbamoylphenyl)isothiazol-4-yl)-6-(2,6-difluorophenyl)picolinamide (4)
2-(2,6-difluorophenyl)-N-(5-(2-morpholinothiazol-4-yl)isothiazol-4-yl)thiazole-4-carboxamide (5)
2-(2,6-difluorophenyl)-N-(5-morpholinoisothiazol-4-yl)thiazole-4-carboxamide (6)
5-amino-2-(2,6-difluorophenyl)-N-(5-morpholinoisothiazol-4-yl)thiazole-4-carboxamide (7)
6-(2,6-difluorophenyl)-N-(5-morpholinoisothiazol-4-yl)picolinamide (8)
tert-butyl (1-(4-(2-(2,6-difluorophenyl)thiazole-4-carboxamido)isothiazol-5-yl)piperidin-4-yl)carbamate (9)
N-(5-(4-aminopiperidin-1-yl)isothiazol-4-yl)-2-(2,6-difluorophenyl)thiazole-4-carboxamide (10)
5-amino-N-(5-(4-aminopiperidin-1-yl)isothiazol-4-yl)-2-(2,6-difluorophenyl)thiazole-4-carboxamide (11)
N-(5-(4-aminopiperidin-1-yl)isothiazol-4-yl)-6-(2,6-difluorophenyl)picolinamide (12)
tert-butyl (1-(4-(2-(2,6-difluorophenyl)thiazole-4-carboxamido)isothiazol-5-yl)piperidin-3-yl)carbamate (13)
N-(5-(3-aminopiperidin-1-yl)isothiazol-4-yl)-2-(2,6-difluorophenyl)thiazole-4-carboxamide (14)
tert-butyl (1-(4-(5-amino-2-(2,6-difluorophenyl)thiazole-4-carboxamido)isothiazol-5-yl)piperidin-3-yl)carbamate (15)
N-(5-(3-aminopiperidin-1-yl)isothiazol-4-yl)-6-(2,6-difluorophenyl)picolinamide (16)
5-amino-2-(2,6-difluorophenyl)-N-(5-(4-hydroxypiperidin-1-yl)isothiazol-4-yl)thiazole-4-carboxamide (17)
2-(2,6-difluorophenyl)-N-(5-(4-hydroxypiperidin-1-yl)isothiazol-4-yl)thiazole-4-carboxamide (18)
N-(5-morpholinoisothiazol-4-yl)-2-(pyridin-4-yl)thiazole-4-carboxamide (19)
N-(5-morpholinoisothiazol-4-yl)-2-(pyridin-3-yl)thiazole-4-carboxamide (20)
N-(5-morpholinoisothiazol-4-yl)-2-(pyridin-2-yl)thiazole-4-carboxamide (21)
2-isopropyl-N-(5-morpholinoisothiazol-4-yl)thiazole-4-carboxamide (22)
N-(5-morpholinoisothiazol-4-yl)-2-(piperidin-1-yl)thiazole-4-carboxamide (23)
2-morpholino-N-(5-morpholinoisothiazol-4-yl)thiazole-4-carboxamide (24)
tert-butyl 4-(4-((5-morpholinoisothiazol-4-yl)carbamoyl)thiazol-2-yl)piperidine-1-carboxylate (25)
N-(5-morpholinoisothiazol-4-yl)-2-(piperidin-4-yl)thiazole-4-carboxamide (26)
2-acetamido-N-(5-morpholinoisothiazol-4-yl)thiazole-4-carboxamide (27)
2-(2,3-dihydrobenzo[b][1,4]dioxin-2-yl)-N-(5-morpholinoisothiazol-4-yl)thiazole-4-carboxamide (28)
1-(2-fluorophenyl)-5-methyl-N-(5-morpholinoisothiazol-4-yl)-1H-pyrazole-3-carboxamide (29)
N-(5-morpholinoisothiazol-4-yl)-2-phenyloxazole-4-carboxamide (30)
N-(5-(piperazin-1-yl)isothiazol-4-yl)-2-(pyridin-4-yl)thiazole-4-carboxamide (31)
N-(5-(piperazin-1-yl)isothiazol-4-yl)-2-(pyridin-3-yl)thiazole-4-carboxamide (32)
N-(5-(piperazin-1-yl)isothiazol-4-yl)-2-(pyridin-2-yl)thiazole-4-carboxamide (33)
2-isopropyl-N-(5-(piperazin-1-yl)isothiazol-4-yl)thiazole-4-carboxamide (34)
N-(5-(piperazin-1-yl)isothiazol-4-yl)-2-(piperidin-1-yl)thiazole-4-carboxamide (35)
2-morpholino-N-(5-(piperazin-1-yl)isothiazol-4-yl)thiazole-4-carboxamide (36)
tert-butyl 4-(4-(2-(1-(tert-butoxycarbonyl)piperidin-4-yl)thiazole-4-carboxamido)isothiazol-5-yl)piperazine-1-carboxylate (37)
N-(5-(piperazin-1-yl)isothiazol-4-yl)-2-(piperidin-4-yl)thiazole-4-carboxamide (38)
2-acetamido-N-(5-(piperazin-1-yl)isothiazol-4-yl)thiazole-4-carboxamide (39)
2-(2,3-dihydrobenzo[b][1,4]dioxin-2-yl)-N-(5-(piperazin-1-yl)isothiazol-4-yl)thiazole-4-carboxamide (40)
1-(2-fluorophenyl)-5-methyl-N-(5-(piperazin-1-yl)isothiazol-4-yl)-1H-pyrazole-3-carboxamide (41)
3-(2-fluorophenyl)-N-(5-(piperazin-1-yl)isothiazol-4-yl)-1H-pyrazole-5-carboxamide (42)
2-phenyl-N-(5-(piperazin-1-yl)isothiazol-4-yl)oxazole-4-carboxamide (43)
2-(2,6-difluorophenyl)-N-(5-(4-(1-hydroxyethyl)piperidin-1-yl)isothiazol-4-yl)thiazole-4-carboxamide (44)
N-(5-(3,8-diazabicyclo[3.2.1]octan-3-yl)isothiazol-4-yl)-2-(2,6-difluorophenyl)thiazole-4-carboxamide (45)
2-(2,6-difluorophenyl)-N-(5-(piperazin-1-yl)isothiazol-4-yl)thiazole-4-carboxamide (46)

6-(2,6-difluorophenyl)-N-(5-(4-hydroxypiperidin-1-yl) isothiazol-4-yl)picolinamide (47)
2-(2,6-difluorophenyl)-N-(5-(4-hydroxyazepan-1-yl) isothiazol-4-yl)thiazole-4-carboxamide (48)
5-amino-2-(2,6-difluorophenyl)-N-(5-(4-hydroxyazepan-1-yl)isothiazol-4-yl)thiazole-4-carboxamide (49)
6-(2,6-difluorophenyl)-N-(5-(4-hydroxyazepan-1-yl) isothiazol-4-yl)picolinamide (50)
2-(2,6-difluorophenyl)-N-(5-(5-hydroxy-3,4-dihydroisoquinolin-2(1H)-yl)isothiazol-4-yl)thiazole-4-carboxamide (51)
6-(2,6-difluorophenyl)-N-(5-(5-hydroxy-3,4-dihydroisoquinolin-2(1H)-yl)isothiazol-4-yl)picolinamide (52)
(S)-2-(2,6-difluorophenyl)-N-(5-(3-(hydroxymethyl)morpholino)isothiazol-4-yl)thiazole-4-carboxamide (53)
2-(2,6-difluorophenyl)-N-(5-(piperidin-4-yloxy)isothiazol-4-yl)thiazole-4-carboxamide (54)
N-(5-(azetidin-3-ylmethoxy)isothiazol-4-yl)-2-(2,6-difluorophenyl)thiazole-4-carboxamide (55)
3-amino-N-(5-(azetidin-3-yloxy)isothiazol-4-yl)-6-(2,6-difluorophenyl)picolinamide (56)
N-(5-(azetidin-3-yloxy)isothiazol-4-yl)-2-(2,6-difluorophenyl)thiazole-4-carboxamide (57)
6-(2,6-difluorophenyl)-N-(5-(piperidin-4-yloxy)isothiazol-4-yl)-picolinamide (58)
5-amino-N-(5-((4-carbamoylcyclohexyl)oxy)isothiazol-4-yl)-2-(2,6-difluorophenyl)thiazole-4-carboxamide (59)
2-(2,6-difluorophenyl)-N-(5-((3-methyloxetan-3-yl)methoxy)isothiazol-4-yl)thiazole-4-carboxamide (60)
3-amino-N-(5-(3-aminopiperidin-1-yl)isothiazol-4-yl)-6-(2,6-difluorophenyl)-picolinamide (61)
2-(2,6-difluorophenyl)-N-(5-(piperidin-4-ylmethoxy) isothiazol-4-yl)thiazole-4-carboxamide (62)
3-amino-6-(2,6-difluorophenyl)-N-(5-(piperidin-4-ylmethoxy)isothiazol-4-yl)picolinamide (63)
(S)-2-(2,6-difluorophenyl)-N-(5-(pyrrolidin-3-yloxy) isothiazol-4-yl)thiazole-4-carboxamide (64)
(R)-2-(2,6-difluorophenyl)-N-(5-(pyrrolidin-3-yloxy) isothiazol-4-yl)thiazole-4-carboxamide (65)
5-amino-N-(5-(3-aminopiperidin-1-yl)isothiazol-4-yl)-2-(2, 6-difluorophenyl)thiazole-4-carboxamide (66)
2-(2,6-difluorophenyl)-N-(5-(3-hydroxypiperidin-1-yl) isothiazol-4-yl)thiazole-4-carboxamide (67)
5-amino-2-(2,6-difluorophenyl)-N-(5-(3-hydroxypiperidin-1-yl)isothiazol-4-yl)thiazole-4-carboxamide (68)
(S)-5-amino-2-(2,6-difluorophenyl)-N-(5-(pyrrolidin-3-yloxy)isothiazol-4-yl)thiazole-4-carboxamide (69)
(R)-5-amino-2-(2,6-difluorophenyl)-N-(5-(pyrrolidin-3-yloxy)isothiazol-4-yl)thiazole-4-carboxamide (70)
3-amino-6-(2,6-difluorophenyl)-N-(5-(3-hydroxypiperidin-1-yl)isothiazol-4-yl)picolinamide (71)
6-(2,6-difluorophenyl)-N-(5-(3-hydroxypiperidin-1-yl) isothiazol-4-yl)picolinamide (72)
5-amino-N-(5-(azepan-4-yloxy)isothiazol-4-yl)-2-(2,6-difluorophenyl)thiazole-4-carboxamide (73)
3-amino-6-(2,6-difluorophenyl)-N-(5-(3-hydroxypropoxy) isothiazol-4-yl)picolinamide (74)
5-amino-N-(5-((trans-4-aminocyclohexyl)oxy)isothiazol-4-yl)-2-(2,6-difluorophenyl)thiazole-4-carboxamide (75)
5-amino-2-(2,6-difluorophenyl)-N-(5-(piperidin-4-ylmethoxy)isothiazol-4-yl)thiazole-4-carboxamide (76)
5-amino-N-(5-(4-aminobutoxy)isothiazol-4-yl)-2-(2,6-difluorophenyl)thiazole-4-carboxamide (77)
5-amino-2-(2,6-difluorophenyl)-N-(5-(4-hydroxybutoxy) isothiazol-4-yl)thiazole-4-carboxamide (78)
5-amino-2-(2,6-difluorophenyl)-N-(5-(2-hydroxyethoxy) isothiazol-4-yl)thiazole-4-carboxamide (79)
5-amino-2-(2,6-difluorophenyl)-N-(5-(3-hydroxypropoxy) isothiazol-4-yl)thiazole-4-carboxamide (80)
5-amino-2-(2,6-difluorophenyl)-N-(5-(3-hydroxypropoxy) isothiazol-4-yl)thiazole-4-carboxamide (81)
5-amino-2-(2,6-difluorophenyl)-N-(5-(3-hydroxy-3-methylbutoxy)isothiazol-4-yl)thiazole-4-carboxamide (82)
2-(2,6-difluorophenyl)-5-formamido-N-(5-((4-hydroxy-4-methylpentyl)oxy)isothiazol-4-yl)thiazole-4-carboxamide (83)
5-amino-2-(2,6-difluorophenyl)-N-(5-((4-hydroxypentyl) oxy)isothiazol-4-yl)thiazole-4-carboxamide (84)
2-(2,6-difluorophenyl)-N-(5-((4-hydroxypentyl)oxy) isothiazol-4-yl)thiazole-4-carboxamide (85)
5-amino-2-(2,6-difluorophenyl)-N-(5-((4-hydroxy-4-methylpentyl)oxy)isothiazol-4-yl)thiazole-4-carboxamide (86)
2-(2,6-difluorophenyl)-N-(5-((4-hydroxy-4-methylpentyl) oxy)isothiazol-4-yl)thiazole-4-carboxamide (87)
5-amino-2-(2,6-difluorophenyl)-N-(5-(2-(2,2-dimethyl-1,3-dioxolan-4-yl)ethoxy)isothiazol-4-yl)thiazole-4-carboxamide (88)
5-amino-2-(2,6-difluorophenyl)-N-(5-((2,2-dimethyl-1,3-dioxolan-4-yl)methoxy)isothiazol-4-yl)thiazole-4-carboxamide (89)
5-amino-2-(2,6-difluorophenyl)-N-(5-(2,3-dihydroxypropoxy)isothiazol-4-yl)thiazole-4-carboxamide (90)
5-amino-2-(2,6-difluorophenyl)-N-(5-(3,4-dihydroxybutoxy)isothiazol-4-yl)thiazole-4-carboxamide (91)
2-(2,6-difluorophenyl)-N-(5-(3,4-dihydroxybutoxy)isothiazol-4-yl)thiazole-4-carboxamide (92)
5-amino-N-(5-(3-aminopropoxy)isothiazol-4-yl)-2-(2,6-difluorophenyl)thiazole-4-carboxamide (93)
5-amino-2-(2,6-difluorophenyl)-N-(5-(3-(methylamino)propoxy)isothiazol-4-yl)thiazole-4-carboxamide (94)
5-amino-2-(2,6-difluorophenyl)-N-(5-(4-(methylamino)butoxy)isothiazol-4-yl)thiazole-4-carboxamide (95)
2-(2,6-difluorophenyl)-N-(5-((4-hydroxy-4-methylpentyl) oxy)isothiazol-4-yl)-5-(methylamino)thiazole-4-carboxamide (96)

Preferred compounds are:
5-amino-2-(2,6-difluorophenyl)-N-(5-(piperidin-4-yloxy) isothiazol-4-yl)thiazole-4-carboxamide (1)
N-(5-(azepan-4-yloxy)isothiazol-4-yl)-2-(2,6-difluorophenyl)thiazole-4-carboxamide (2)
N-(5-(4-carbamoylphenyl)isothiazol-4-yl)-2-(2,6-difluorophenyl)thiazole-4-carboxamide (3)
N-(5-(4-carbamoylphenyl)isothiazol-4-yl)-6-(2,6-difluorophenyl)picolinamide (4)
2-(2,6-difluorophenyl)-N-(5-(2-morpholinothiazol-4-yl) isothiazol-4-yl)thiazole-4-carboxamide (5)
N-(5-(4-aminopiperidin-1-yl)isothiazol-4-yl)-2-(2,6-difluorophenyl)thiazole-4-carboxamide (10)
5-amino-N-(5-(4-aminopiperidin-1-yl)isothiazol-4-yl)-2-(2, 6-difluorophenyl)thiazole-4-carboxamide (11)
N-(5-(4-aminopiperidin-1-yl)isothiazol-4-yl)-6-(2,6-difluorophenyl)picolinamide (12)
N-(5-(3-aminopiperidin-1-yl)isothiazol-4-yl)-2-(2,6-difluorophenyl)thiazole-4-carboxamide (14)
N-(5-(3-aminopiperidin-1-yl)isothiazol-4-yl)-6-(2,6-difluorophenyl)picolinamide (16)
5-amino-2-(2,6-difluorophenyl)-N-(5-(4-hydroxypiperidin-1-yl)isothiazol-4-yl)thiazole-4-carboxamide (17)
2-(2,6-difluorophenyl)-N-(5-(4-hydroxypiperidin-1-yl) isothiazol-4-yl)thiazole-4-carboxamide (18)
N-(5-morpholinoisothiazol-4-yl)-2-(pyridin-2-yl)thiazole-4-carboxamide (21)
N-(5-(piperazin-1-yl)isothiazol-4-yl)-2-(pyridin-2-yl)thiazole-4-carboxamide (33)

N-(5-(3,8-diazabicyclo[3.2.1]octan-3-yl)isothiazol-4-yl)-2-(2,6-difluorophenyl)thiazole-4-carboxamide (45)
2-(2,6-difluorophenyl)-N-(5-(piperazin-1-yl)isothiazol-4-yl)thiazole-4-carboxamide (46)
2-(2,6-difluorophenyl)-N-(5-(4-hydroxyazepan-1-yl)isothiazol-4-yl)thiazole-4-carboxamide (48)
5-amino-2-(2,6-difluorophenyl)-N-(5-(4-hydroxyazepan-1-yl)isothiazol-4-yl)thiazole-4-carboxamide (49)
6-(2,6-difluorophenyl)-N-(5-(4-hydroxyazepan-1-yl)isothiazol-4-yl)picolinamide (50)
2-(2,6-difluorophenyl)-N-(5-(piperidin-4-yloxy)isothiazol-4-yl)thiazole-4-carboxamide (54)
N-(5-(azetidin-3-ylmethoxy)isothiazol-4-yl)-2-(2,6-difluorophenyl)thiazole-4-carboxamide (55)
3-amino-N-(5-(azetidin-3-yloxy)isothiazol-4-yl)-6-(2,6-difluorophenyl)picolinamide (56)
N-(5-(azetidin-3-yloxy)isothiazol-4-yl)-2-(2,6-difluorophenyl)thiazole-4-carboxamide (57)
6-(2,6-difluorophenyl)-N-(5-(piperidin-4-yloxy)isothiazol-4-yl)-picolinamide (58)
5-amino-N-(5-((4-carbamoylcyclohexyl)oxy)isothiazol-4-yl)-2-(2,6-difluorophenyl)thiazole-4-carboxamide (59)
2-(2,6-difluorophenyl)-N-(5-((3-methyloxetan-3-yl)methoxy)isothiazol-4-yl)thiazole-4-carboxamide (60)
3-amino-N-(5-(3-aminopiperidin-1-yl)isothiazol-4-yl)-6-(2,6-difluorophenyl)-picolinamide (61)
2-(2,6-difluorophenyl)-N-(5-(piperidin-4-ylmethoxy)isothiazol-4-yl)thiazole-4-carboxamide (62)
3-amino-6-(2,6-difluorophenyl)-N-(5-(piperidin-4-ylmethoxy)isothiazol-4-yl)picolinamide (63)
(S)-2-(2,6-difluorophenyl)-N-(5-(pyrrolidin-3-yloxy)isothiazol-4-yl)thiazole-4-carboxamide (64)
(R)-2-(2,6-difluorophenyl)-N-(5-(pyrrolidin-3-yloxy)isothiazol-4-yl)thiazole-4-carboxamide (65)
5-amino-N-(5-(3-aminopiperidin-1-yl)isothiazol-4-yl)-2-(2,6-difluorophenyl)thiazole-4-carboxamide (66)
2-(2,6-difluorophenyl)-N-(5-(3-hydroxypiperidin-1-yl)isothiazol-4-yl)thiazole-4-carboxamide (67)
5-amino-2-(2,6-difluorophenyl)-N-(5-(3-hydroxypiperidin-1-yl)isothiazol-4-yl)thiazole-4-carboxamide (68)
(S)-5-amino-2-(2,6-difluorophenyl)-N-(5-(pyrrolidin-3-yloxy)isothiazol-4-yl)thiazole-4-carboxamide (69)
(R)-5-amino-2-(2,6-difluorophenyl)-N-(5-(pyrrolidin-3-yloxy)isothiazol-4-yl)thiazole-4-carboxamide (70)
3-amino-6-(2,6-difluorophenyl)-N-(5-(3-hydroxypiperidin-1-yl)isothiazol-4-yl)picolinamide (71)
6-(2,6-difluorophenyl)-N-(5-(3-hydroxypiperidin-1-yl)isothiazol-4-yl)picolinamide (72)
5-amino-N-(5-(azepan-4-yloxy)isothiazol-4-yl)-2-(2,6-difluorophenyl)thiazole-4-carboxamide (73)
3-amino-6-(2,6-difluorophenyl)-N-(5-(3-hydroxypropoxy)isothiazol-4-yl)picolinamide (74)
5-amino-N-(5-((trans-4-aminocyclohexyl)oxy)isothiazol-4-yl)-2-(2,6-difluorophenyl)thiazole-4-carboxamide (75)
5-amino-2-(2,6-difluorophenyl)-N-(5-(piperidin-4-ylmethoxy)isothiazol-4-yl)thiazole-4-carboxamide (76)
5-amino-N-(5-(4-aminobutoxy)isothiazol-4-yl)-2-(2,6-difluorophenyl)thiazole-4-carboxamide (77)
5-amino-2-(2,6-difluorophenyl)-N-(5-(4-hydroxybutoxy)isothiazol-4-yl)thiazole-4-carboxamide (78)
5-amino-2-(2,6-difluorophenyl)-N-(5-(2-hydroxyethoxy)isothiazol-4-yl)thiazole-4-carboxamide (79)
5-amino-2-(2,6-difluorophenyl)-N-(5-(3-hydroxypropoxy)isothiazol-4-yl)thiazole-4-carboxamide (80)
5-amino-2-(2,6-difluorophenyl)-N-(5-(3-hydroxypropoxy)isothiazol-4-yl)thiazole-4-carboxamide (81)
5-amino-2-(2,6-difluorophenyl)-N-(5-(3-hydroxy-3-methylbutoxy)isothiazol-4-yl)thiazole-4-carboxamide (82)
2-(2,6-difluorophenyl)-5-formamido-N-(5-((4-hydroxy-4-methylpentyl)oxy)isothiazol-4-yl)thiazole-4-carboxamide (83)
5-amino-2-(2,6-difluorophenyl)-N-(5-((4-hydroxypentyl)oxy)isothiazol-4-yl)thiazole-4-carboxamide (84)
2-(2,6-difluorophenyl)-N-(5-((4-hydroxypentyl)oxy)isothiazol-4-yl)thiazole-4-carboxamide (85)
5-amino-2-(2,6-difluorophenyl)-N-(5-((4-hydroxy-4-methylpentyl)oxy)isothiazol-4-yl)thiazole-4-carboxamide (86)
2-(2,6-difluorophenyl)-N-(5-((4-hydroxy-4-methylpentyl)oxy)isothiazol-4-yl)thiazole-4-carboxamide (87)
5-amino-2-(2,6-difluorophenyl)-N-(5-(2-(2,2-dimethyl-1,3-dioxolan-4-yl)ethoxy)isothiazol-4-yl)thiazole-4-carboxamide (88)
5-amino-2-(2,6-difluorophenyl)-N-(5-((2,2-dimethyl-1,3-dioxolan-4-yl)methoxy)isothiazol-4-yl)thiazole-4-carboxamide (89)
5-amino-2-(2,6-difluorophenyl)-N-(5-(3,4-dihydroxybutoxy)isothiazol-4-yl)thiazole-4-carboxamide (91)
2-(2,6-difluorophenyl)-N-(5-(3,4-dihydroxybutoxy)isothiazol-4-yl)thiazole-4-carboxamide (92)
5-amino-N-(5-(3-aminopropoxy)isothiazol-4-yl)-2-(2,6-difluorophenyl)thiazole-4-carboxamide (93)
5-amino-2-(2,6-difluorophenyl)-N-(5-(3-(methylamino)propoxy)isothiazol-4-yl)thiazole-4-carboxamide (94)
5-amino-2-(2,6-difluorophenyl)-N-(5-(4-(methylamino)butoxy)isothiazol-4-yl)thiazole-4-carboxamide (95)
2-(2,6-difluorophenyl)-N-(5-((4-hydroxy-4-methylpentyl)oxy)isothiazol-4-yl)-5-(methylamino)thiazole-4-carboxamide (96)

More preferred compounds are:
5-amino-2-(2,6-difluorophenyl)-N-(5-(piperidin-4-yloxy)isothiazol-4-yl)thiazole-4-carboxamide (1)
N-(5-(azepan-4-yloxy)isothiazol-4-yl)-2-(2,6-difluorophenyl)thiazole-4-carboxamide (2)
N-(5-(4-carbamoylphenyl)isothiazol-4-yl)-2-(2,6-difluorophenyl)thiazole-4-carboxamide (3)
N-(5-(4-carbamoylphenyl)isothiazol-4-yl)-6-(2,6-difluorophenyl)picolinamide (4)
2-(2,6-difluorophenyl)-N-(5-(2-morpholinothiazol-4-yl)isothiazol-4-yl)thiazole-4-carboxamide (5)
N-(5-(4-aminopiperidin-1-yl)isothiazol-4-yl)-2-(2,6-difluorophenyl)thiazole-4-carboxamide (10)
5-amino-N-(5-(4-aminopiperidin-1-yl)isothiazol-4-yl)-2-(2,6-difluorophenyl)thiazole-4-carboxamide (11)
N-(5-(4-aminopiperidin-1-yl)isothiazol-4-yl)-6-(2,6-difluorophenyl)picolinamide (12)
N-(5-(3-aminopiperidin-1-yl)isothiazol-4-yl)-2-(2,6-difluorophenyl)thiazole-4-carboxamide (14)
N-(5-(3-aminopiperidin-1-yl)isothiazol-4-yl)-6-(2,6-difluorophenyl)picolinamide (16)
5-amino-2-(2,6-difluorophenyl)-N-(5-(4-hydroxypiperidin-1-yl)isothiazol-4-yl)thiazole-4-carboxamide (17)
2-(2,6-difluorophenyl)-N-(5-(4-hydroxypiperidin-1-yl)isothiazol-4-yl)thiazole-4-carboxamide (18)
N-(5-(3,8-diazabicyclo[3.2.1]octan-3-yl)isothiazol-4-yl)-2-(2,6-difluorophenyl)thiazole-4-carboxamide (45)
5-amino-2-(2,6-difluorophenyl)-N-(5-(4-hydroxyazepan-1-yl)isothiazol-4-yl)thiazole-4-carboxamide (49)
2-(2,6-difluorophenyl)-N-(5-(piperidin-4-yloxy)isothiazol-4-yl)thiazole-4-carboxamide (54)
N-(5-(azetidin-3-ylmethoxy)isothiazol-4-yl)-2-(2,6-difluorophenyl)thiazole-4-carboxamide (55)
3-amino-N-(5-(azetidin-3-yloxy)isothiazol-4-yl)-6-(2,6-difluorophenyl)picolinamide (56)

N-(5-(azetidin-3-yloxy)isothiazol-4-yl)-2-(2,6-difluorophenyl)thiazole-4-carboxamide (57)
6-(2,6-difluorophenyl)-N-(5-(piperidin-4-yloxy)isothiazol-4-yl)-picolinamide (58)
5-amino-N-(5-((4-carbamoylcyclohexyl)oxy)isothiazol-4-yl)-2-(2,6-difluorophenyl)thiazole-4-carboxamide (59)
2-(2,6-difluorophenyl)-N-(5-((3-methyloxetan-3-yl)methoxy)isothiazol-4-yl)thiazole-4-carboxamide (60)
3-amino-N-(5-(3-aminopiperidin-1-yl)isothiazol-4-yl)-6-(2,6-difluorophenyl)-picolinamide (61)
2-(2,6-difluorophenyl)-N-(5-(piperidin-4-ylmethoxy)isothiazol-4-yl)thiazole-4-carboxamide (62)
3-amino-6-(2,6-difluorophenyl)-N-(5-(piperidin-4-ylmethoxy)isothiazol-4-yl)picolinamide (63)
(S)-2-(2,6-difluorophenyl)-N-(5-(pyrrolidin-3-yloxy)isothiazol-4-yl)thiazole-4-carboxamide (64)
(R)-2-(2,6-difluorophenyl)-N-(5-(pyrrolidin-3-yloxy)isothiazol-4-yl)thiazole-4-carboxamide (65)
5-amino-N-(5-(3-aminopiperidin-1-yl)isothiazol-4-yl)-2-(2,6-difluorophenyl)thiazole-4-carboxamide (66)
2-(2,6-difluorophenyl)-N-(5-(3-hydroxypiperidin-1-yl)isothiazol-4-yl)thiazole-4-carboxamide (67)
5-amino-2-(2,6-difluorophenyl)-N-(5-(3-hydroxypiperidin-1-yl)isothiazol-4-yl)thiazole-4-carboxamide (68)
(S)-5-amino-2-(2,6-difluorophenyl)-N-(5-(pyrrolidin-3-yloxy)isothiazol-4-yl)thiazole-4-carboxamide (69)
(R)-5-amino-2-(2,6-difluorophenyl)-N-(5-(pyrrolidin-3-yloxy)isothiazol-4-yl)thiazole-4-carboxamide (70)
3-amino-6-(2,6-difluorophenyl)-N-(5-(3-hydroxypiperidin-1-yl)isothiazol-4-yl)picolinamide (71)
6-(2,6-difluorophenyl)-N-(5-(3-hydroxypiperidin-1-yl)isothiazol-4-yl)picolinamide (72)
5-amino-N-(5-(azepan-4-yloxy)isothiazol-4-yl)-2-(2,6-difluorophenyl)thiazole-4-carboxamide (73)
3-amino-6-(2,6-difluorophenyl)-N-(5-(3-hydroxypropoxy)isothiazol-4-yl)picolinamide (74)
5-amino-N-(5-((trans-4-aminocyclohexyl)oxy)isothiazol-4-yl)-2-(2,6-difluorophenyl)thiazole-4-carboxamide (75)
5-amino-2-(2,6-difluorophenyl)-N-(5-(piperidin-4-ylmethoxy)isothiazol-4-yl)thiazole-4-carboxamide (76)
5-amino-N-(5-(4-aminobutoxy)isothiazol-4-yl)-2-(2,6-difluorophenyl)thiazole-4-carboxamide (77)
5-amino-2-(2,6-difluorophenyl)-N-(5-(4-hydroxybutoxy)isothiazol-4-yl)thiazole-4-carboxamide (78)
5-amino-2-(2,6-difluorophenyl)-N-(5-(3-hydroxypropoxy)isothiazol-4-yl)thiazole-4-carboxamide (80)
5-amino-2-(2,6-difluorophenyl)-N-(5-(3-hydroxypropoxy)isothiazol-4-yl)thiazole-4-carboxamide (81)
5-amino-2-(2,6-difluorophenyl)-N-(5-(3-hydroxy-3-methylbutoxy)isothiazol-4-yl)thiazole-4-carboxamide (82)
2-(2,6-difluorophenyl)-5-formamido-N-(5-((4-hydroxy-4-methylpentyl)oxy)isothiazol-4-yl)thiazole-4-carboxamide (83)
5-amino-2-(2,6-difluorophenyl)-N-(5-((4-hydroxypentyl)oxy)isothiazol-4-yl)thiazole-4-carboxamide (84)
2-(2,6-difluorophenyl)-N-(5-((4-hydroxypentyl)oxy)isothiazol-4-yl)thiazole-4-carboxamide (85)
5-amino-2-(2,6-difluorophenyl)-N-(5-((4-hydroxy-4-methylpentyl)oxy)isothiazol-4-yl)thiazole-4-carboxamide (86)
2-(2,6-difluorophenyl)-N-(5-((4-hydroxy-4-methylpentyl)oxy)isothiazol-4-yl)thiazole-4-carboxamide (87)
5-amino-2-(2,6-difluorophenyl)-N-(5-(2-(2,2-dimethyl-1,3-dioxolan-4-yl)ethoxy)isothiazol-4-yl)thiazole-4-carboxamide (88)
5-amino-2-(2,6-difluorophenyl)-N-(5-((2,2-dimethyl-1,3-dioxolan-4-yl)methoxy)isothiazol-4-yl)thiazole-4-carboxamide (89)
5-amino-2-(2,6-difluorophenyl)-N-(5-(3,4-dihydroxybutoxy)isothiazol-4-yl)thiazole-4-carboxamide (91)
2-(2,6-difluorophenyl)-N-(5-(3,4-dihydroxybutoxy)isothiazol-4-yl)thiazole-4-carboxamide (92)
5-amino-N-(5-(3-aminopropoxy)isothiazol-4-yl)-2-(2,6-difluorophenyl)thiazole-4-carboxamide (93)
5-amino-2-(2,6-difluorophenyl)-N-(5-(3-(methylamino)propoxy)isothiazol-4-yl)thiazole-4-carboxamide (94)
5-amino-2-(2,6-difluorophenyl)-N-(5-(4-(methylamino)butoxy)isothiazol-4-yl)thiazole-4-carboxamide (95)
2-(2,6-difluorophenyl)-N-(5-((4-hydroxy-4-methylpentyl)oxy)isothiazol-4-yl)-5-(methylamino)thiazole-4-carboxamide (96)

The present invention also provides the methods of synthesis of the above PIM kinase inhibitors.

The compounds in this invention are made from commercial available starting materials and reagents. This invention is illustrated in the following scheme:

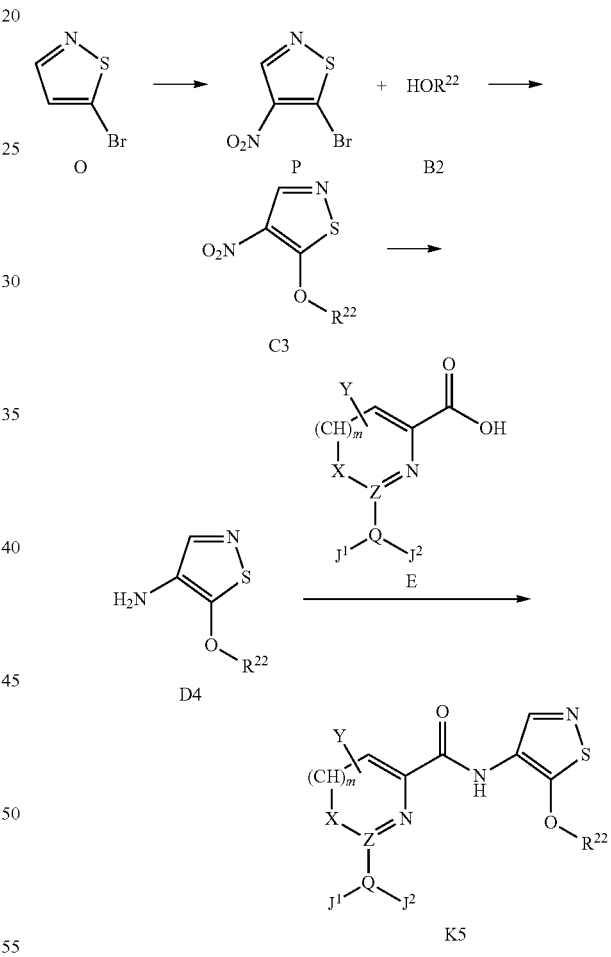

In the above scheme, X, Y, Z, $J^1$, $J^2$, Q, m and $R^{22}$ are the same as defined earlier.

(1) The general procedure for the synthesis of compounds when E of Formula I is ether group:

5-bromoisothiazole (O) (1 eq.) is nitrated to 4-nitro-5-bromoisothiazole (P) in a mixed acid of concentrated $H_2SO_4$ and concentrated $HNO_3$ (3:1 ratio; 10-50 eq.) at 70° C. To a protected or unprotected alcohol B2 (1 eq.) in a solvent, for example THF (tetrahydrofuran) at room temperature (25° C.) was added a base, for example NaH (1.2 eq.) and stirred for 0.5-1 hour. 4-nitro-5-bromoisothiazole P (0.8 eq.) was then added. The mixture was then heated to, for example 65° C., and stirred for 2-10 hours, to form ether C3. C3 (1 eq.) reacts with Na$_2$S$_2$O$_4$ (3 eq.) in a solvent, for example methanol, in the presence of a base, for example saturated NaHCO$_3$ solution (3 eq.), under heated conditions, for example 35° C., for 1-10 hours to form aminoisothiazole D4. A protected or unprotected carboxylic acid E (1 eq.) reacts with aminoisothiazole D4 (1 eq.) in a solvent, for example DMF (N,N-dimethyl formaldehyde) in the presence of a coupling reagent, for example HATU (1-[bis(dimethylamino)methylene]-1H-1,2,3-triazolo[4,5-b]pyridinium 3-oxid hexafluorophosphate) (1.2 eq.) and a base, for example DIEA (N,N-diisopropylethylamine) (3 eq.), in a solvent, for example DMF, at heated conditions, for example 40-50° C., for 1-5 hours to form an ether K5. If there is no protecting group in K5, then K5 is final ether product of Formula I where E is ether group. If K5 is protected by protecting group, for example BOC (tert-butyloxycarbonyl), it's deprotected by treating with mixture of TFA (trifluoroacetic acid) (10-100 eq.) with equal volume of dichloromethane at room temperature (25° C.) for 1-16 hours. The final ether product K5 of Formula I where E is ether group is obtained after removing the solvent in vacuo at room temperature (25° C.).

(2) The general procedure for the synthesis of compounds when E of Formula I is aromatic or heteroaromatic group:

NaHCO$_3$ water solution (3 eq.), under heated conditions, for example 120° C. for 10-60 min, to form a nitroisothiazole intermediate C4. C4 (1 eq.) reacts with Na$_2$S$_2$O$_4$ (3 eq.) in a solvent, for example methanol, in the presence of a base, for example saturated NaHCO$_3$ solution (3 eq.) under heated conditions, for example 35° C., for 1-10 hours to form aminoisothiazole D5. A protected or unprotected carboxylic acid E (1 eq.) reacts with aminoisothiazole D5 (1 eq.) in a solvent, for example DMF in the presence of a coupling reagent, for example HATU (1.2 eq.) and a base, for example DIEA (3 eq.), in a solvent, for example DMF at heated conditions, for example 40-50° C., for 1-5 hours to form bi-aryl compound K6. If there is no protecting group in K6, then K6 is final bi-aryl product of Formula I where E is aromatic or heteroaromatic group. If K6 is protected by protecting group, for example BOC, it's deprotected by treating with mixture of TFA (10-100 eq.) with equal volume of dichloromethane at room temperature (25° C.) for 1-16 hours. The final bi-aryl product K6 of Formula I where E is aromatic or heteroaromatic group is obtained after removing the solvent in vacuo at room temperature (25° C.).

(3) The general procedure for the synthesis of compounds when E of Formula I is secondary amine group:

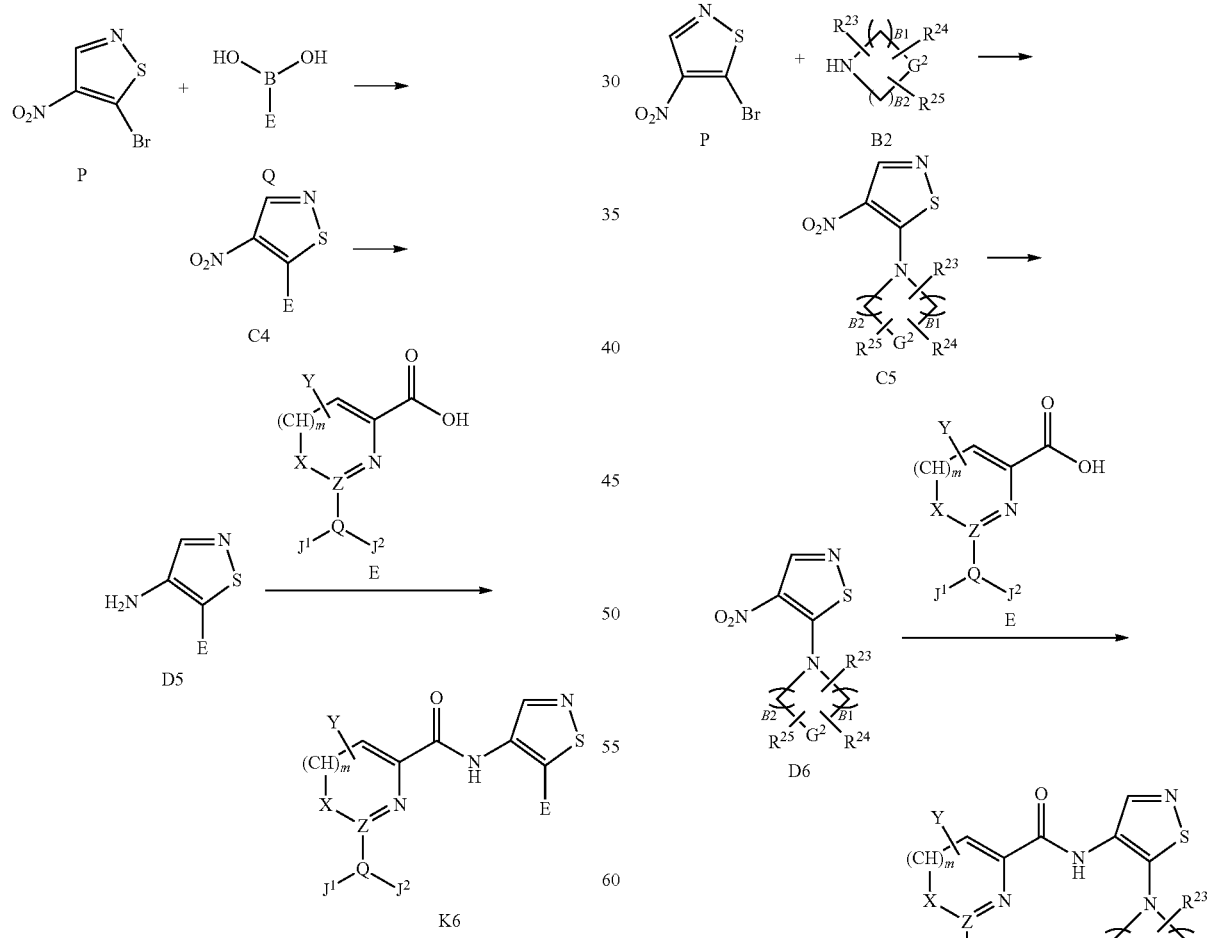

4-nitro-5-bromoisothiazole P (1 eq.) reacts with protected or unprotected boronic acid Q (1 eq.) in a solvent, for example dioxane, in the presence of a catalyst, for example bis(tri-tert-butylphosphine)palladium (0), a base, for example saturated 4-nitro-5-bromoisothiazole P (1 eq.) reacts with protected or unprotected secondary amine B2 (1 eq.) in a solvent, for example dioxane, in the presence of a base, for example saturated DIEA (2 eq.), under heated conditions, for example 40° C. for 1-4 hours, to form a nitroisothiazole intermediate C5. C5 (1 eq.) reacts with Na₂S₂O₄ (3 eq.) in a solvent, for example methanol, in the presence of a base, for example saturated NaHCO₃ water solution (3 eq.) under heated conditions, for example 35° C., for 1-10 hours to form aminoisothiazole D6. A protected or unprotected carboxylic acid E (1 eq.) reacts with aminoisothiazole D6 (1 eq.) in a solvent, for example DMF in the presence of a coupling reagent, for example HATU (1.2 eq.) and a base, for example DIEA (3 eq.), in a solvent, for example DMF at heated conditions, for example 40-50° C., for 1-5 hours to form bi-aryl compound K7. If there is no protecting group in K6, then K6 is final amine product of Formula I where E is secondary amine group. If K7 is protected by protecting group, for example BOC, it's deprotected by treating with mixture of TFA (10-100 eq.) with equal volume of dichloromethane at room temperature (25° C.) for 1-16 hours. The final amine product K7 of Formula I where E is secondary amino group is obtained after removing the solvent in vacuo at room temperature (25° C.).

The present invention also provides the pharmaceutical application of the above PIM kinase inhibitors.

The PIM kinase assays showed that all compounds in all the examples can significantly inhibit the PIM-1 activity. At 3 μM concentration, most compounds showed over 50% inhibition of PIM-1 kinase activity, some as high as 100% except 10 compounds (25, 26, 28, 36, 39, 40, 41, 42, 43, 52) which have PIM-1 inhibition rate of 20-50%. The compounds of in the examples also show excellent inhibitory activities against PIM-2 and PIM-3 kinase. At 3 μM concentration, they can inhibit PIM-2 and PIM-3 by as much as 100%. Therefore, the PIM kinase inhibitors in the present invention can be used for pharmaceuticals.

The present invention provides the use of the above PIM kinase inhibitors as drugs to treat or prevent cancers.

The present invention provides the use of the above PIM kinase inhibitors as drugs to treat or prevent autoimmune diseases.

The present invention provides the use of the above PIM kinase inhibitors as drugs to treat or prevent allergic reactions.

The present invention provides the use of the above PIM kinase inhibitors as drugs to treat or prevent atherosclerosis.

The present invention provides the use of the above PIM kinase inhibitors as drugs to treat or prevent organ transplant rejection.

The drugs in present invention use PIM kinase inhibitors as active ingredients along with excipients The present invention provides the new application of PIM kinase inhibitors and has significant clinical value.

EXAMPLES

The following examples are set forth for illustration only to help understand the invention described herein and not to be construed as limiting the present invention in any manner.

Example 1

Synthesis of 5-amino-2-(2,6-difluorophenyl)-N-(5-(piperidin-4-yloxy)isothiazol-4-yl)thiazole-4-carboxamide (1)

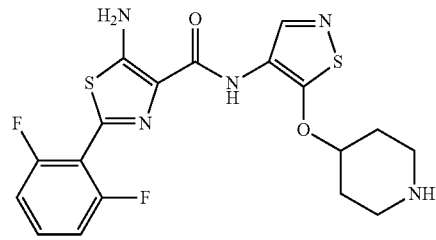 [SMILES: Nc1sc(-c2c(F)cccc2F)nc1C(=O)Nc1cnsc1OC1CCNCC1]

(1) Synthesis of 5-bromo-4-nitroisothiazole (P)

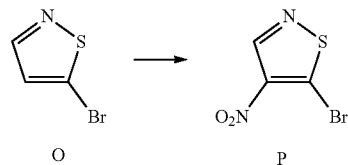

To a solution of concentrated H₂SO₄ (15 mL) and HNO₃ (6 mL) at 0° C. was added 5-bromoisothiazole (O) (5.0 g, 29.4 mmol). The mixture was then stirred at 70° C. for 1.5 hours. After cooling to room temperature, it was poured into stirring ice water (120 mL). The mixture was then extracted with ethyl acetate twice (150 mL×2). The combined organic phases were dried over Na₂SO₄ and concentrated in vacuo at room temperature (25° C.). The residue was purified with flash column (eluent: 5-20% ethyl acetate/petroleum ether) to afford the product 5-bromo-4-nitroisothiazole (P) (4.4 g, 21 mmol).

(2) Synthesis of tert-butyl 4-(4-nitroisothiazol-5-yloxy)piperidine-1-carboxylate (1C3)

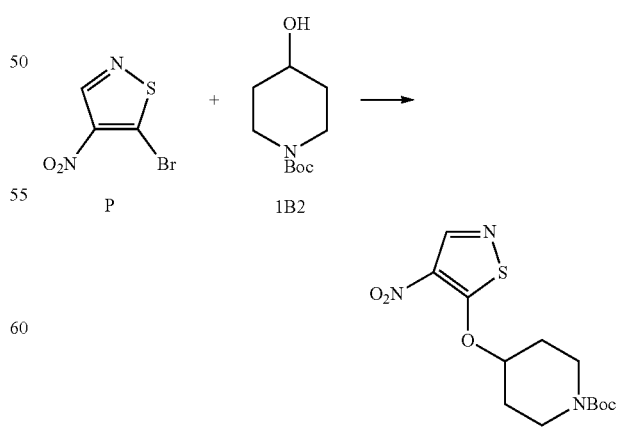

To a solution of tert-butyl 4-hydroxypiperidine-1-carboxylate (1B2) (464 mg, 2.3 mmol) in dioxane (10 mL) at room temperature was added NaH (114 mg, 2.8 mmol). The mixture was stirred for 20 min and 5-bromo-4-nitroisothiazole (P) (400 mg, 1.9 mmol) was added. The mixture was stirred at 65° C. for 5 hours, cooled to room temperature, diluted with ethyl acetate (100 mL), washed with brine, dried over $Na_2SO_4$, and concentrated in vacuo at room temperature (25° C.). The residue was purified with flash column (eluent: 10-30% ethyl acetate/petroleum ether) to afford the product tert-butyl 4-(4-nitroisothiazol-5-yloxy)piperidine-1-carboxylate (1C3) (280 mg, 0.85 mmol).

(3) tert-butyl 4-(4-aminoisothiazol-5-yloxy)piperidine-1-carboxylate (1D4)

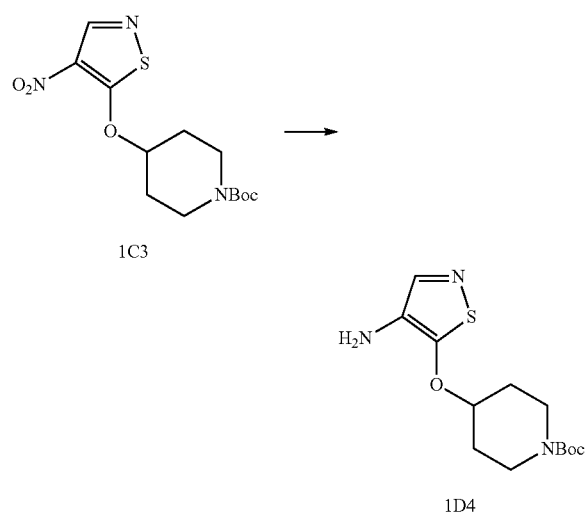

To a solution of tert-butyl 4-(4-nitroisothiazol-5-yloxy)piperidine-1-carboxylate (1C3) (213 mg, 0.67 mmol) in methanol (4 mL) at room temperature was added water (3 mL), saturated $NaHCO_3$ solution (3 mL) and $Na_2S_2O_4$ (340 mg, 2 mmol). The mixture was stirred at 35° C. for 3 hours, cooled to room temperature, diluted with ethyl acetate (100 mL), washed with brine, dried over $Na_2SO_4$, and concentrated in vacuo at room temperature (25° C.). The residue was purified with flash column (eluent: 10-30% ethyl acetate/petroleum ether) to afford the product tert-butyl 4-(4-aminoisothiazol-5-yloxy)piperidine-1-carboxylate (1D4) (80 mg, 0.27 mmol).

(4) Synthesis of tert-butyl 4-(4-(5-amino-2-(2,6-difluorophenyl)thiazole-4-carboxamido)isothiazol-5-yloxy)piperidine-1-carboxylate (1A)

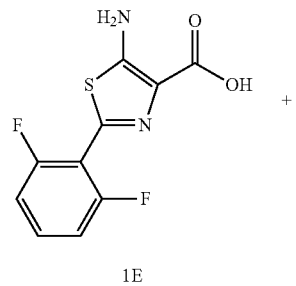

+

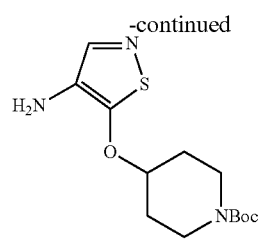

→ tert-butyl 4-(4-aminoisothiazol-5-yloxy)piperidine-1-carboxylate (1D4) (47 mg, 0.156 mmol), 5-amino-2-(2,6-difluorophenyl)thiazole-4-carboxylic acid (1E) (40 mg, 0.156 mmol), HATU (71 mg, 0.187 mmol) and DIEA (84 μL, 0.468 mmol) were mixed in DMF (5 mL), stirred at 50° C. for 1 hour, cooled to room temperature, diluted with ethyl acetate (50 mL), washed with brine, dried over $Na_2SO_4$, and concentrated in vacuo at room temperature (25° C.). The residue was purified with flash column (eluent: 10-30% ethyl acetate/petroleum ether) to afford the product tert-butyl 4-(4-(5-amino-2-(2,6-difluorophenyl)thiazole-4-carboxamido)isothiazol-5-yloxy)piperidine-1-carboxylate (1A) (17 mg, 0.031 mmol).

(5) Synthesis of 5-amino-2-(2,6-difluorophenyl)-N-(5-(piperidin-4-yloxy)isothiazol-4-yl)thiazole-4-carboxamide (1)

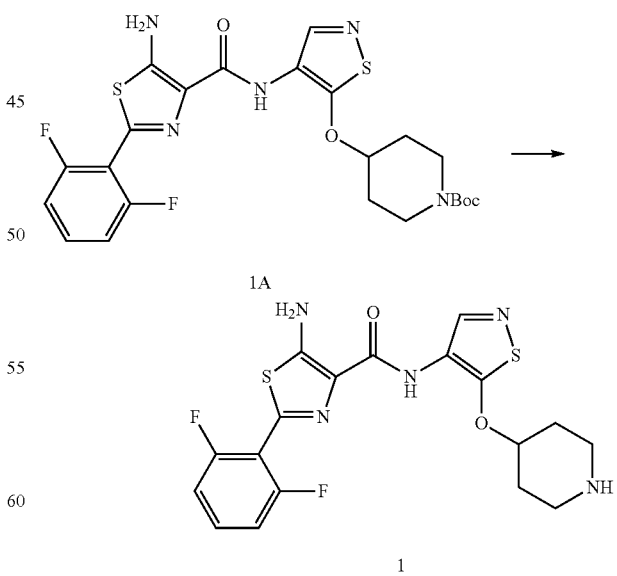

To a solution of tert-butyl 4-(4-(5-amino-2-(2,6-difluorophenyl)thiazole-4-carboxamido)isothiazol-5-yloxy)piperidine-1-carboxylate (1A) (10 mg, 0.02 mmol) in $CH_2Cl_2$ (1 mL) at room temperature (25° C.) was added TFA (trifluoroacetic acid) (0.5 mL), stirred for 10 min and then concentrated in vacuo at room temperature (25° C.) to afford the product 5-amino-2-(2,6-difluorophenyl)-N-(5-(piperidin-4-yloxy)isothiazol-4-yl)thiazole-4-carboxamide (1) (5 mg, 0.011 mmol)

Example 2

Synthesis of N-(5-(azepan-4-yloxy)isothiazol-4-yl)-2-(2,6-difluorophenyl)thiazole-4-carboxamide (2)

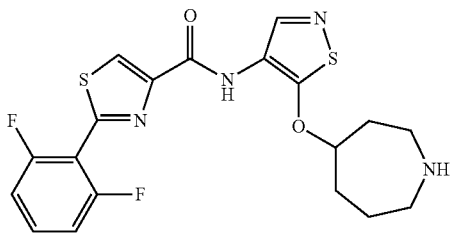 [SMILES: O=C(Nc1cnsc1OC1CCCNCC1)c1csc(-c2c(F)cccc2F)n1]

Following the procedure described in Example 1, and substituting Compound 1B2 in Step (1) with tert-butyl 4-hydroxyazepane-1-carboxylate (2B2) (200 mg, 0.93 mmol) and Compound 1E in Step 4 with 2-(2,6-difluorophenyl)thiazole-4-carboxylic acid (2E) (40 mg, 0.166 mmol), the title compound 2 (35 mg, 0.080 mmol) was obtained.

Example 3

Synthesis of N-(5-(4-carbamoylphenyl)isothiazol-4-yl)-2-(2,6-difluorophenyl)thiazole-4-carboxamide (3)

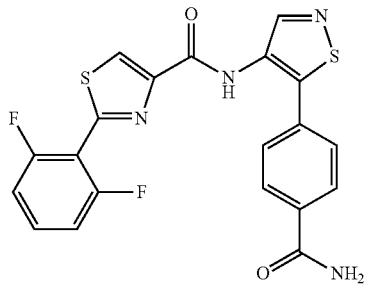 [SMILES: NC(=O)c1ccc(-c2sncc2NC(=O)c2csc(-c3c(F)cccc3F)n2)cc1]

(1) Synthesis of 4-(4-nitroisothiazol-5-yl)benzamide (3C4)

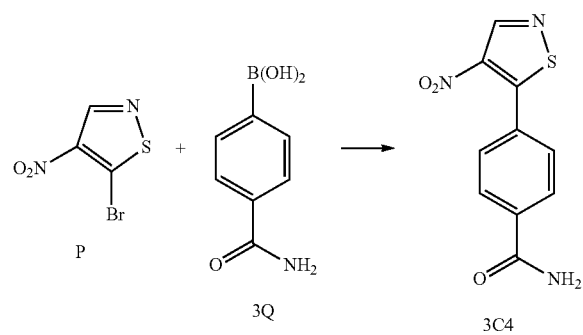

To a solution of 4-carbamoylphenylboronic acid (3Q) (157 mg, 0.96 mmol) and 5-bromo-4-nitroisothiazole (P) (200 mg, 0.96 mmol) in dioxane was bubbled was nitrogen gas for 5 min Bis(tri-tert-butylphosphine)palladium (0) (49 mg, 0.096 mmol) and 1.2M NaHCO₃ water solution (241 mg, 2.9 mmol) was added and stirred at 120° C. under nitrogen atmosphere for 15 min The mixture was cooled to room temperature, diluted with ethyl acetate (50 mL), washed with water, and concentrated in vacuo at room temperature (25° C.) to afford the product 4-(4-nitroisothiazol-5-yl)benzamide (3C4) (250 mg, 96 mmol)

(2) Synthesis of 4-(4-aminoisothiazol-5-yl)benzamide (3D5)

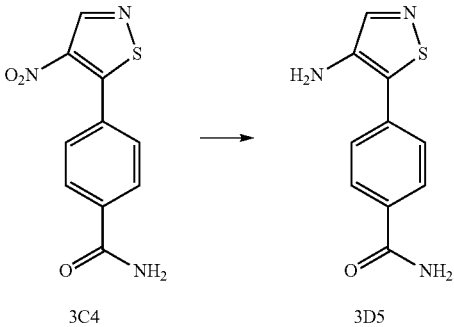 [SMILES: NC(=O)c1ccc(-c2sncc2[N+](=O)[O-])cc1 ; NC(=O)c1ccc(-c2sncc2N)cc1]

Following the procedure described in Step 3 of Example 1, and substituting Compound 1C3 with 4-(4-nitroisothiazol-5-yl)benzamide (3C3) (250 mg, 1.0 mmol), 4-(4-aminoisothiazol-5-yl)benzamide (3D5) (209 mg, 0.954 mmol) was obtained.

(3) Synthesis of N-(5-(4-carbamoylphenyl)isothiazol-4-yl)-2-(2,6-difluorophenyl)thiazole-4-carboxamide (3)

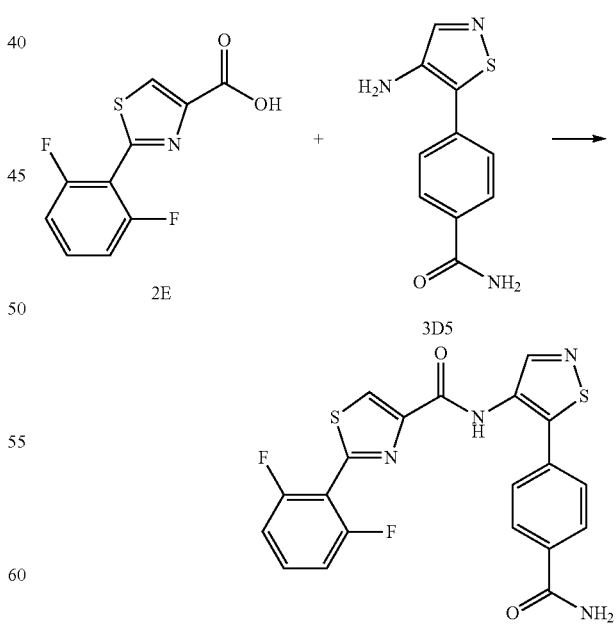

Following the procedure described in Step 4 of Example 1, and substituting Compounds 1D4 and 1E with 4-(4-aminoisothiazol-5-yl)benzamide (3D5) (80 mg, 0.37 mmol) and 2-(2,6-difluorophenyl)thiazole-4-carboxylic acid (2E) (88 mg, 0.365 mmol) respectively, the title compound 3 (8 mg, 0.018 mmol) was obtained.

Example 4

Synthesis of N-(5-(4-carbamoylphenyl)isothiazol-4-yl)-6-(2,6-difluorophenyl)picolinamide (4)

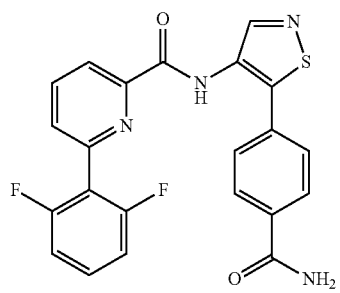 [SMILES: NC(=O)c1ccc(-c2sncc2NC(=O)c2cccc(-c3c(F)cccc3F)n2)cc1]

Following the procedure described in Example 3, and substituting Compound 2E in Step (3) with 6-(2,6-difluorophenyl)picolinic acid (4E) (54 mg, 0.228 mmol) the title compound 4 (11 mg, 0.025 mmol) was obtained.

Example 5

Synthesis of 2-(2,6-difluorophenyl)-N-(5-(2-morpholinothiazol-4-yl)isothiazol-4-yl)thiazole-4-carboxamide (5)

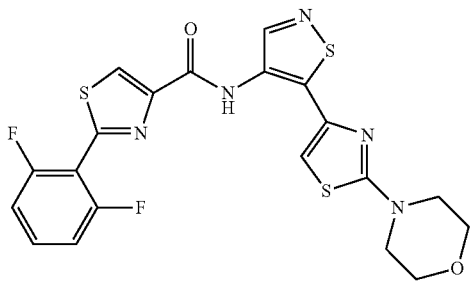 [SMILES: O=C(Nc1cnsc1-c1csc(N2CCOCC2)n1)c1csc(-c2c(F)cccc2F)n1]

Following the procedure described in Example 3, and substituting Compound 3Q in Step (1) with 4-(4-(((4,4,5,5-tetramethyl-1,3,2-dioxaborolan-2-yl)oxy)thiazol-2-yl)morpholine (5Q) (283 mg, 0.96 mmol), the title compound 5 (130 mg, 0.456 mmol) was obtained.

Example 6

Synthesis of 2-(2,6-difluorophenyl)-N-(5-morpholinoisothiazol-4-yl)thiazole-4-carboxamide (6)

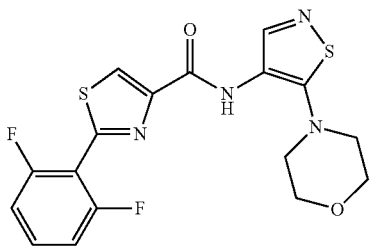 [SMILES: O=C(Nc1cnsc1N1CCOCC1)c1csc(-c2c(F)cccc2F)n1]

(1) Synthesis of 4-(4-nitroisothiazol-5-yl)morpholine (6C6)

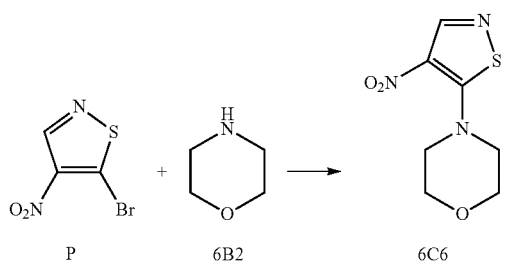

To a solution of 5-bromo-4-nitroisothiazole (P) (500 mg, 2.39 mmol) and morpholine (6B2) (620 mg, 7.12 mmol) in dioxane (10 mL) at room temperature (25° C.) was added DIEA (851 µL, 4.78 mmol). The solution was stirred for 30 min and HPLC showed the reaction was complete. Water (10 mL) was then added. A precipitate was formed, filtered and air dried at room temperature to get the product 6C6 (500 mg, 2.32 mmol).

(2) Synthesis of 5-morpholinoisothiazol-4-amine (6D8)

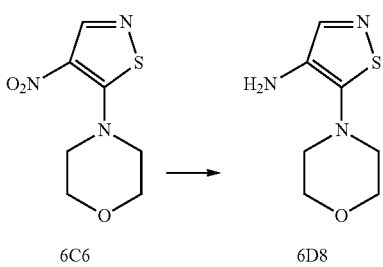

Following the procedure described in Example 1, and substituting Compound 1C3 in Step (3) with 4-(4-nitroisothiazol-5-yl)morpholine (6C6) (500 mg, 2.32 mmol) the compound 6D8 (300 mg, 1.62 mmol) was obtained.

(3) Synthesis of 2-(2,6-difluorophenyl)-N-(5-morpholinoisothiazol-4-yl)thiazole-4-carboxamide (6)

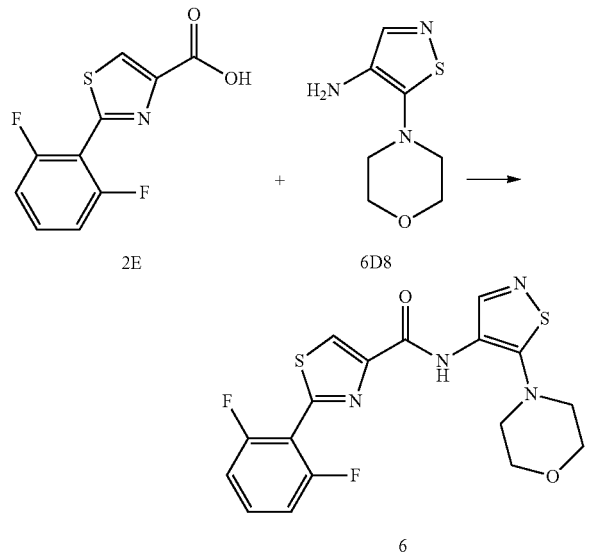

Following the procedure described in Step 4 of Example 1, and substituting Compounds 1D4 and 1E with 5-morpholinoisothiazol-4-amine (6D8) (100 mg, 0.54 mmol) and 2-(2,6-difluorophenyl)thiazole-4-carboxylic acid (2E) (156 mg, 0.647 mmol) respectively, the title compound 6 (100 mg, 0.245 mmol) was obtained.

Example 7

Synthesis of 5-amino-2-(2,6-difluorophenyl)-N-(5-morpholinoisothiazol-4-yl)thiazole-4-carboxamide (7)

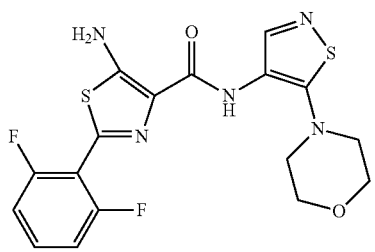 [SMILES: Nc1sc(-c2c(F)cccc2F)nc1C(=O)Nc1cnsc1N1CCOCC1]

Following the procedure described in Example 6, and substituting Compound 2E in Step (3) with 5-amino-2-(2,6-difluorophenyl)thiazole-4-carboxylic acid (1E) (70 mg, 0.27 mmol), the title compound 7 (5 mg, 0.012 mmol) was obtained.

Example 8

Synthesis of 6-(2,6-difluorophenyl)-N-(5-morpholinoisothiazol-4-yl)picolinamide (8)

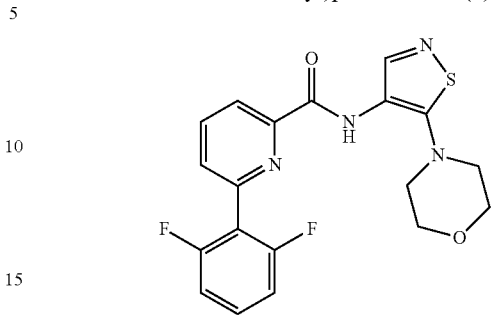

Following the procedure described in Example 7, and substituting Compound 2E in Step (3) with 6-(2,6-difluorophenyl)picolinic acid (4E) (120 mg, 0.51 mmol), the title compound 8 (100 mg, 0.249 mmol) was obtained.

Example 9

Synthesis of tert-butyl (1-(4-(2-(2,6-difluorophenyl)thiazole-4-carboxamido)isothiazol-5-yl)piperidin-4-yl)carbamate (9)

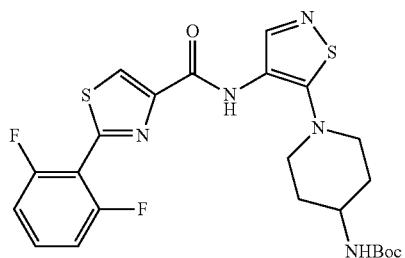 [SMILES: CC(C)(C)OC(=O)NC1CCN(c2sncc2NC(=O)c2csc(-c3c(F)cccc3F)n2)CC1]

Following the procedure described in Example 6, and substituting Compound 6B2 in Step (1) with tert-butyl (1-methylpiperidin-4-yl)carbamate (9 L) (316 mg, 1.58 mmol), the title compound 9 (109 mg, 0.211 mmol) was obtained.

Example 10

Synthesis of N-(5-(4-aminopiperidin-1-yl)isothiazol-4-yl)-2-(2,6-difluorophenyl)thiazole-4-carboxamide (10)

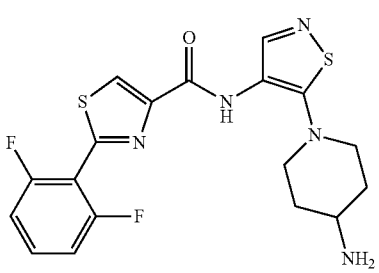 [SMILES: NC1CCN(c2sncc2NC(=O)c2csc(-c3c(F)cccc3F)n2)CC1]

Following the procedure described in the Step (5) of Example 1, and substituting Compound 1 with tert-butyl (1-(4-(2-(2,6-difluorophenyl)thiazole-4-carboxamido)isothiazol-5-yl)piperidin-4-yl)carbamate (9) (110 mg, 0.20 mmol), the title compound 10 (50 mg, 0.119 mmol) was obtained.

Example 11

Synthesis of 5-amino-N-(5-(4-aminopiperidin-1-yl)isothiazol-4-yl)-2-(2,6-difluorophenyl)thiazole-4-carboxamide (11)

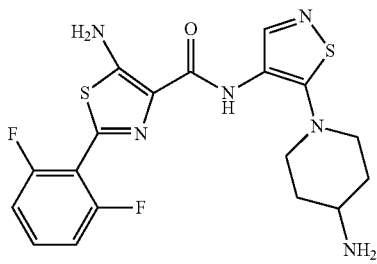 [SMILES: Nc1sc(-c2c(F)cccc2F)nc1C(=O)Nc1cnsc1N1CCC(N)CC1]

Following the procedure described in Example 9 and 10, and substituting Compound 2E in Step (1) of Example 9 with 5-amino-2-(2,6-difluorophenyl)thiazole-4-carboxylic acid (1E) (50 mg, 0.195 mmol), the title compound 11 (14 mg, 0.032 mmol) was obtained.

Example 12

Synthesis of N-(5-(4-aminopiperidin-1-yl)isothiazol-4-yl)-6-(2,6-difluorophenyl)picolinamide (12)

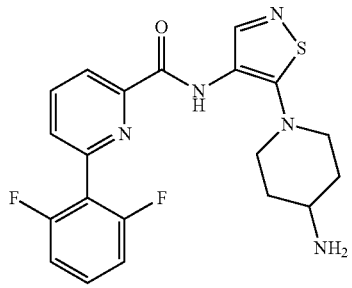 [SMILES: NC1CCN(c2sncc2NC(=O)c2cccc(-c3c(F)cccc3F)n2)CC1]

Following the procedure described in Example 11, and substituting Compound 1E in Step (3) with 6-(2,6-difluorophenyl)picolinic acid (4E) (50 mg, 0.21 mmol), the title compound 12 (25 mg, 0.060 mmol) was obtained.

Example 13

Synthesis of tert-butyl (1-(4-(2-(2,6-difluorophenyl)thiazole-4-carboxamido)isothiazol-5-yl)piperidin-3-yl)carbamate (13)

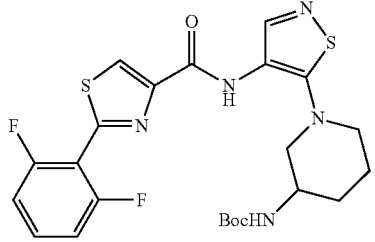

Following the procedure described in Example 6, and substituting Compound 6B2 in Step (1) with tert-butyl piperidin-3-ylcarbamate (13 L) (287 mg, 1.44 mmol), the title compound 13 (100 mg, 0.192 mmol) was obtained.

Example 14

Synthesis of N-(5-(3-aminopiperidin-1-yl)isothiazol-4-yl)-2-(2,6-difluorophenyl)thiazole-4-carboxamide (14)

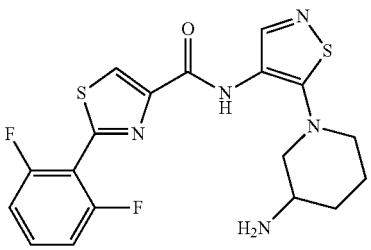 [SMILES: NC1CCCN(c2sncc2NC(=O)c2csc(-c3c(F)cccc3F)n2)C1]

Following the procedure described in the Step (5) of Example 1, and substituting Compound 1A with tert-butyl (1-(4-(2-(2,6-difluorophenyl)thiazole-4-carboxamido)isothiazol-5-yl)piperidin-3-yl)carbamate (13) (40 mg, 0.077 mmol), the title compound 14 (18 mg, 0.043 mmol) was obtained.

Example 15

Synthesis of tert-butyl (1-(4-(5-amino-2-(2,6-difluorophenyl)thiazole-4-carboxamido)isothiazol-5-yl)piperidin-3-yl)carbamate (15)

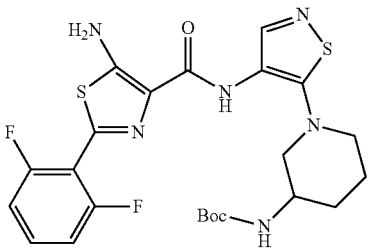 [SMILES: CC(C)(C)OC(=O)NC1CCCN(c2sncc2NC(=O)c2nc(-c3c(F)cccc3F)sc2N)C1]

Following the procedure described in Example 13, and substituting Compound 2E in Step (3) with 5-amino-2-(2,6-difluorophenyl)thiazole-4-carboxylic acid (1E) (34 mg, 0.133 mmol), the title compound 15 (48 mg, 0.0896 mmol)) was obtained.

Example 16

Synthesis of N-(5-(3-aminopiperidin-1-yl)isothiazol-4-yl)-6-(2,6-difluorophenyl)picolinamide (16)

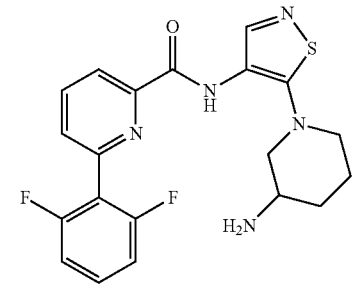 [SMILES: NC1CCCN(c2sncc2NC(=O)c2cccc(-c3c(F)cccc3F)n2)C1]

Following the procedure described in Example 11, and substituting Compound 2E with 6(2,6-difluorophenyl)picolinic acid (4E) (39 mg, 0.166 mmol), the title compound 16 (18 mg, 0.043 mmol) was obtained.

Example 17

Synthesis of 5-amino-2-(2,6-difluorophenyl)-N-(5-(4-hydroxypiperidin-1-yl)isothiazol-4-yl)thiazole-4-carboxamide (17)

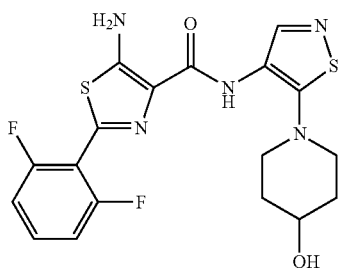 [SMILES: Nc1sc(-c2c(F)cccc2F)nc1C(=O)Nc1cnsc1N1CCC(O)CC1]

Following the procedure described in Example 6, and substituting Compound 6B2 in Step (1) with piperidin-4-ol (17B2) (159 mg, 1.57 mmol), the title compound 17 (50 mg, 0.114 mmol) was obtained.

Example 18

Synthesis of 2-(2,6-difluorophenyl)-N-(5-(4-hydroxypiperidin-1-yl)isothiazol-4-yl)thiazole-4-carboxamide (18)

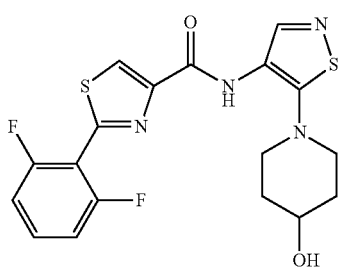 [SMILES: O=C(Nc1cnsc1N1CCC(O)CC1)c1csc(-c2c(F)cccc2F)n1]

Following the procedure described in Example 17, and substituting Compound 1E with 2-(2,6-difluorophenyl)thiazole-4-carboxylic acid (2E) (67 mg, 0.278 mmol), the title compound 18 (18 mg, 0.043 mmol) was obtained.

Example 19

Synthesis of N-(5-morpholinoisothiazol-4-yl)-2-(pyridin-4-yl)thiazole-4-carboxamide (19)

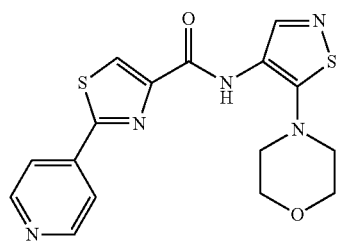 [SMILES: O=C(Nc1cnsc1N1CCOCC1)c1csc(-c2ccncc2)n1]

Following the procedure described in Step (3) of Example 6, and substituting Compound 2E with 2-(pyridin-4-yl)thiazole-4-carboxylic acid (19E) (50 mg, 0.24 mmol), the title compound 19 (50 mg, 0.134 mmol) was obtained.

Example 20

Synthesis of N-(5-morpholinoisothiazol-4-yl)-2-(pyridin-3-yl)thiazole-4-carboxamide (20)

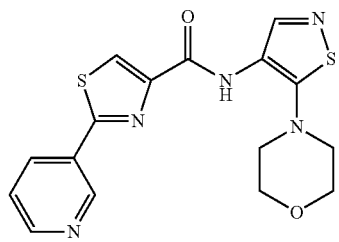 [SMILES: O=C(Nc1cnsc1N1CCOCC1)c1csc(-c2cccnc2)n1]

Following the procedure described in Step (3) of Example 6, and substituting Compound 2E with 2-(pyridin-3-yl)thiazole-4-carboxylic acid (20E) (50 mg, 0.24 mmol), the title compound 20 (80 mg, 0.214 mmol) was obtained.

Example 21

Synthesis of N-(5-morpholinoisothiazol-4-yl)-2-(pyridin-2-yl)thiazole-4-carboxamide (21)

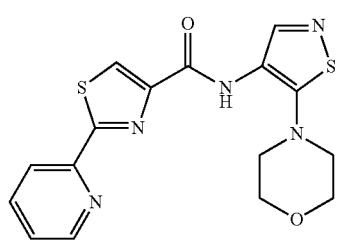 [SMILES: O=C(Nc1cnsc1N1CCOCC1)c1csc(-c2ccccn2)n1]

Following the procedure described in Step (3) of Example 6, and substituting Compound 2E with 2-(pyridin-2-yl)thiazole-4-carboxylic acid (21E) (50 mg, 0.24 mmol), the title compound 21 (20 mg, 0.054 mmol) was obtained.

Example 22

Synthesis of 2-isopropyl-N-(5-morpholinoisothiazol-4-yl)thiazole-4-carboxamide (22)

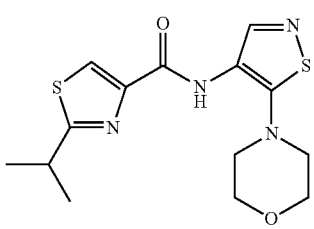 [SMILES: CC(C)c1nc(C(=O)Nc2cnsc2N2CCOCC2)cs1]

Following the procedure described in Step (3) of Example 6, and substituting Compound 2E with 2-isopropyl-N-(5-morpholinoisothiazol-4-yl)thiazole-4-carboxamide (22E) (77 mg, 0.43 mmol), the title compound 22 (68 mg, 0.195 mmol) was obtained.

Example 23

Synthesis of N-(5-morpholinoisothiazol-4-yl)-2-(piperidin-1-yl)thiazole-4-carboxamide (23)

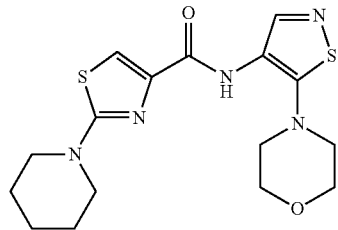 [SMILES: O=C(Nc1cnsc1N1CCOCC1)c1csc(N2CCCCC2)n1]

Following the procedure described in Step (3) of Example 6, and substituting Compound 2E with 2-(piperidin-1-yl)thiazole-4-carboxylic acid (23E) (69 mg, 0.325 mmol), the title compound 23 (100 mg, 0.264 mmol) was obtained.

Example 24

Synthesis of 2-morpholino-N-(5-morpholinoisothiazol-4-yl)thiazole-4-carboxamide (24)

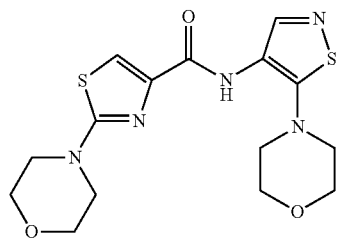 [SMILES: O=C(Nc1cnsc1N1CCOCC1)c1csc(N2CCOCC2)n1]

Following the procedure described in Step (3) of Example 6, and substituting Compound 2E with 2-morpholinothiazole-4-carboxylic acid (24E) (58 mg, 0.271 mmol), the title compound 24 (70 mg, 0.184 mmol) was obtained.

Example 25

Synthesis of tert-butyl 4-(4-((5-morpholinoisothiazol-4-yl)carbamoyl)thiazol-2-yl)piperidine-1-carboxylate (25)

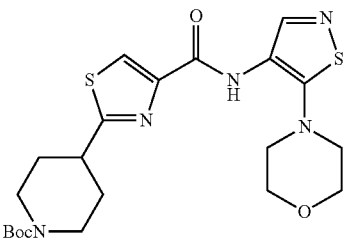 [SMILES: CC(C)(C)OC(=O)N1CCC(c2nc(C(=O)Nc3cnsc3N3CCOCC3)cs2)CC1]

Following the procedure described in Step (3) of Example 6, and substituting Compound 2E with 2-(1-(tert-butoxycarbonyl)piperidin-4-yl)thiazole-4-carboxylic acid (25E) (101 mg, 0.324 mmol), the title compound 25 (140 mg, 0.29 mmol) was obtained.

Example 26

Synthesis of N-(5-morpholinoisothiazol-4-yl)-2-(piperidin-4-yl)thiazole-4-carboxamide (26)

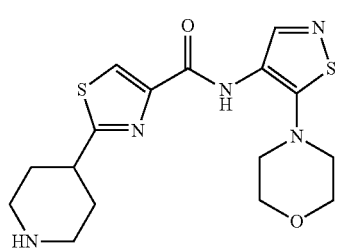 [SMILES: O=C(Nc1cnsc1N1CCOCC1)c1csc(C2CCNCC2)n1]

Following the procedure described in Step (3) of Example 6, and substituting Compound 2E with 2-(1-(tert-butoxycarbonyl)piperidin-4-yl)thiazole-4-carboxylic acid (26E) (110 mg, 0.23 mmol), the title compound 26 (39 mg, 0.103 mmol) was obtained.

Example 27

Synthesis of 2-acetamido-N-(5-morpholinoisothiazol-4-yl)thiazole-4-carboxamide (27)

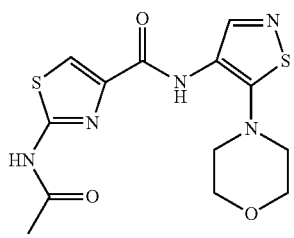 [SMILES: CC(=O)Nc1nc(C(=O)Nc2cnsc2N2CCOCC2)cs1]

Following the procedure described in Step (3) of Example 6, and substituting Compound 2E with 2-acetamido-N-(5-morpholinoisothiazol-4-yl)thiazole-4-carboxamide (27E) (90 mg, 0.484 mmol), the title compound 27 (100 mg, 0.283 mmol) was obtained.

Example 28

Synthesis of 2-(2,3-dihydrobenzo[b][1,4]dioxin-2-yl)-N-(5-morpholinoisothiazol-4-yl)thiazole-4-carboxamide (28)

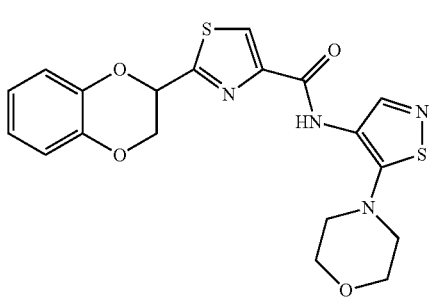 [SMILES: O=C(Nc1cnsc1N1CCOCC1)c1csc(C2COc3ccccc3O2)n1]

Following the procedure described in Step (3) of Example 6, and substituting Compound 2E with 2-(2,3-dihydrobenzo[b][1,4]dioxin-2-yl)thiazole-4-carb oxylic acid (28E) (136 mg, 0.517 mmol), the title compound 28 (100 mg, 0.232 mmol) was obtained.

Example 29

Synthesis of 1-(2-fluorophenyl)-5-methyl-N-(5-morpholinoisothiazol-4-yl)-1H-pyrazole-3-carboxamide (29)

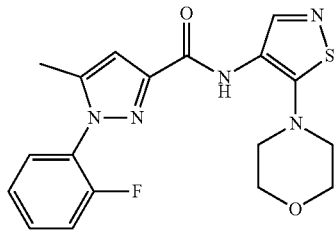 [SMILES: Cc1cc(C(=O)Nc2cnsc2N2CCOCC2)nn1-c1ccccc1F]

Following the procedure described in Step (3) of Example 6, and substituting Compound 2E with 1-(2-fluorophenyl)-5-methyl-1H-pyrazole-3-carboxylic acid (29E) (114 mg, 0.518 mmol), the title compound 29 (120 mg, 0.31 mmol) was obtained.

Example 30

Synthesis of N-(5-morpholinoisothiazol-4-yl)-2-phenyloxazole-4-carboxamide (30)

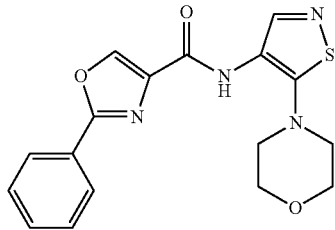 [SMILES: O=C(Nc1cnsc1N1CCOCC1)c1coc(-c2ccccc2)n1]

Following the procedure described in Step (3) of Example 6, and substituting Compound 2E with 2-phenyloxazole-4-carboxylic acid (30E) (98 mg, 0.52 mmol), the title compound 30 (100 mg, 0.28 mmol) was obtained.

Example 31

Synthesis of N-(5-(piperazin-1-yl)isothiazol-4-yl)-2-(pyridin-4-yl)thiazole-4-carboxamide (31)

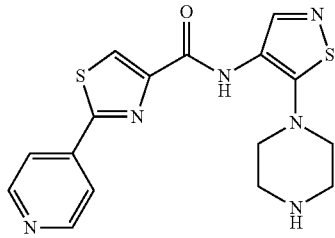 [SMILES: O=C(Nc1cnsc1N1CCNCC1)c1csc(-c2ccncc2)n1]

(1) Synthesis of tert-butyl 4-(4-nitroisothiazol-5-yl)piperazine-1-carboxylate (31C3)

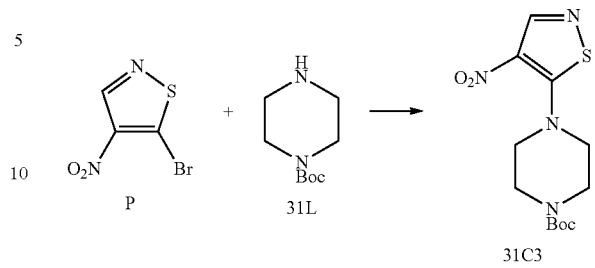

Following the procedure described in Step (1) of Example 6, and substituting Compound 6B2 in Step (1) with tert-butyl piperazine-1-carboxylate (31 L) (356 mg, 1.91 mmol), the Compound 31C3 (600 mg, 1.91 mmol) was obtained.

(2) Synthesis of tert-butyl 4-(4-aminoisothiazol-5-yl)piperazine-1-carboxylate (31D3)

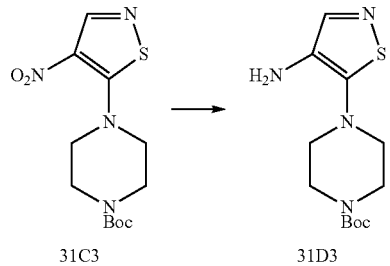 [SMILES: CC(C)(C)OC(=O)N1CCN(c2sncc2[N+](=O)[O-])CC1 ; CC(C)(C)OC(=O)N1CCN(c2sncc2N)CC1]

Following the procedure described in Step (3) of Example 1, and substituting Compound 6C3 in Step (1) with tert-butyl 4-(4-nitroisothiazol-5-yl)piperazine-1-carboxylate (31C3) (600 mg, 1.91 mmol), Compound 31D3 (410 mg, 1.44 mmol) was obtained.

(3) Synthesis of tert-butyl 4-(4-(2-(pyridin-4-yl)thiazole-4-carboxamido)isothiazol-5-yl)piperazine-1-carboxylate (31A)

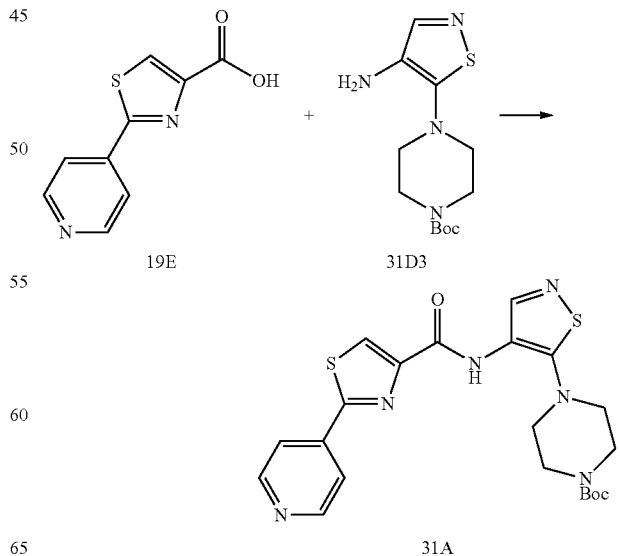

Following the procedure described in Step (3) of Example 6, and substituting Compounds 2E and 6D8 with 2-(pyridin-4-yl)thiazole-4-carboxylic acid (19E) (58 mg, 0.28 mmol) and tert-butyl 4-(4-aminoisothiazol-5-yl)piperazine-1-carboxylate (31D3) (80 mg, 0.28 mmol) respectively, Compound 31A (120 mg, 0.25 mmol) was obtained.

(4) Synthesis of N-(5-(piperazin-1-yl)isothiazol-4-yl)-2-(pyridin-4-yl)thiazole-4-carboxamide (31)

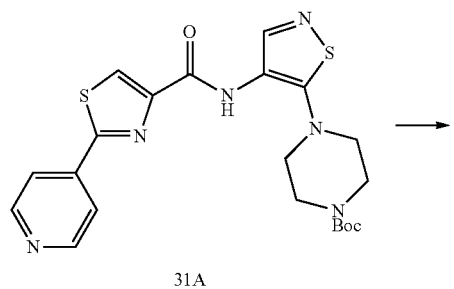

31A

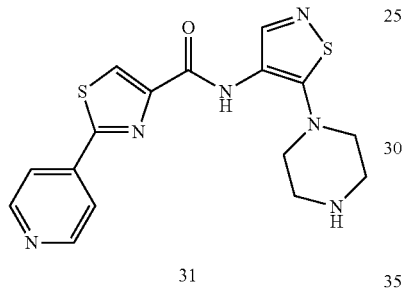

31

Following the procedure described in Step (5) Example 1, and substituting Compound 1A with tert-butyl 4-(4-(2-(pyridin-4-yl)thiazole-4-carboxamido)isothiazol-5-yl)piperazine-1-carboxylate (31A) (100 mg, 0.21 mmol), the title compound 31 (58 mg, 0.156 mmol) was obtained.

Example 32

Synthesis of N-(5-(piperazin-1-yl)isothiazol-4-yl)-2-(pyridin-3-yl)thiazole-4-carboxamide (32)

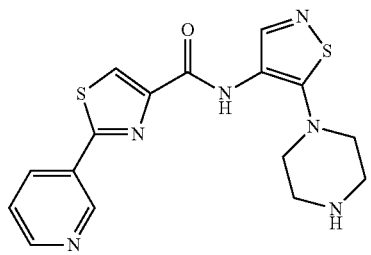 [SMILES: O=C(Nc1cnsc1N1CCNCC1)c1csc(-c2cccnc2)n1]

Following the procedure described in Example 31, and substituting Compound 19E with 2-(pyridin-3-yl)thiazole-4-carboxylic acid (20E) (120 mg, 0.25 mmol), the title compound 32 (63 mg, 0.169 mmol) was obtained.

Example 33

Synthesis of N-(5-(piperazin-1-yl)isothiazol-4-yl)-2-(pyridin-2-yl)thiazole-4-carboxamide (33)

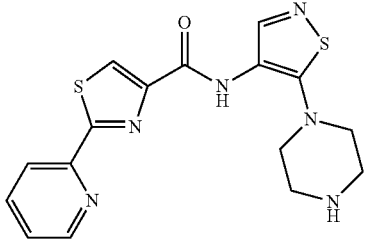 [SMILES: O=C(Nc1cnsc1N1CCNCC1)c1csc(-c2ccccn2)n1]

Following the procedure described in Example 31, and substituting Compound 19E with 2-(pyridin-2-yl)thiazole-4-carboxylic acid (21E) (98 mg, 0.476 mmol), the title compound 33 (32 mg, 0.086 mmol) was obtained.

Example 34

Synthesis of 2-isopropyl-N-(5-(piperazin-1-yl)isothiazol-4-yl)thiazole-4-carboxamide (34)

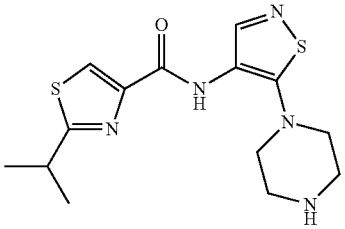 [SMILES: CC(C)c1nc(C(=O)Nc2cnsc2N2CCNCC2)cs1]

Following the procedure described in Example 31, and substituting Compound 19E with 2-isopropyl-N-(5-morpholinoisothiazol-4-yl)thiazole-4-carb oxamide (22E) (51 mg, 0.298 mmol), the title compound 34 (51 mg, 0.151 mmol) was obtained.

Example 35

Synthesis of N-(5-(piperazin-1-yl)isothiazol-4-yl)-2-(piperidin-1-yl)thiazole-4-carboxamide (35)

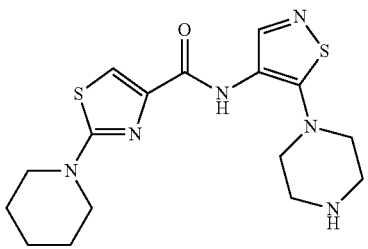 [SMILES: O=C(Nc1cnsc1N1CCNCC1)c1csc(N2CCCCC2)n1]

Following the procedure described in Example 31, and substituting Compound 19E with 2-(piperidin-1-yl)thiazole-4-carboxylic acid (23E) (55 mg, 0.26 mmol), the title compound 35 (16 mg, 0.042 mmol) was obtained.

Example 36

Synthesis of 2-morpholino-N-(5-(piperazin-1-yl)isothiazol-4-yl)thiazole-4-carboxamide (36)

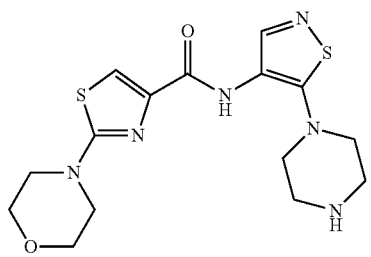 [SMILES: O=C(Nc1cnsc1N1CCNCC1)c1csc(N2CCOCC2)n1]

Following the procedure described in Example 31, and substituting Compound 19E with 2-morpholinothiazole-4-carboxylic acid (24E) (55 mg, 0.257 mmol), the title compound 36 (40 mg, 0.105 mmol) was obtained.

Example 37 and Example 38

Synthesis of tert-butyl 4-(4-(2-(1-(tert-butoxycarbonyl)piperidin-4-yl)thiazole-4-carboxamido)isothiazol-5-yl)piperazine-1-carboxylate (37) 和 N-(5-(piperazin-1-yl)isothiazol-4-yl)-2-(piperidin-4-yl)thiazole-4-carboxamide (38)

37
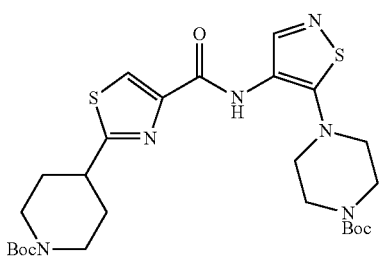

38
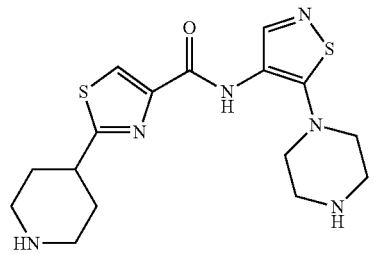

Following the procedure described in Example 31, and substituting Compound 19E with 2-(1-(tert-butoxycarbonyl)piperidin-4-yl)thiazole-4-carboxylic acid (25E) (92 mg, 0.295 mmol), the title compound 37 (150 mg, 0.26 mmol) and 38 (80 mg, 0.211 mmol) were obtained.

Example 39

Synthesis of 2-acetamido-N-(5-(piperazin-1-yl)isothiazol-4-yl)thiazole-4-carboxamide (39)

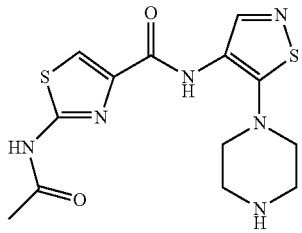 [SMILES: CC(=O)Nc1nc(C(=O)Nc2cnsc2N2CCNCC2)cs1]

Following the procedure described in Example 31, and substituting Compound 19E with 2-acetamido-N-(5-morpholinoisothiazol-4-yl)thiazole-4-carboxamide (27E) (63 mg, 0.339 mmol), the title compound 39 (63 mg, 0.339 mmol) was obtained.

Example 40

Synthesis of 2-(2,3-dihydrobenzo[b][1,4]dioxin-2-yl)-N-(5-(piperazin-1-yl)isothiazol-4-yl)thiazole-4-carboxamide (40)

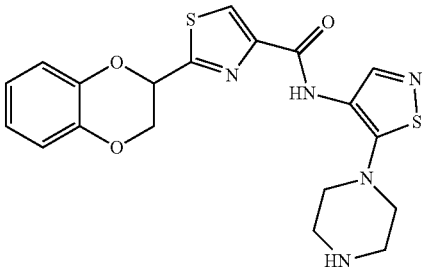 [SMILES: O=C(Nc1cnsc1N1CCNCC1)c1csc(C2COc3ccccc3O2)n1]

Following the procedure described in Example 31, and substituting Compound 19E with 2-(2,3-dihydrobenzo[b][1,4]dioxin-2-yl)thiazole-4-carboxylic acid (28E) (88 mg, 0.33 mmol), the title compound 40 (15 mg, 0.035 mmol) was obtained.

Example 41

Synthesis of 1-(2-fluorophenyl)-5-methyl-N-(5-(piperazin-1-yl)isothiazol-4-yl)-1H-pyrazole-3-carboxamide (41)

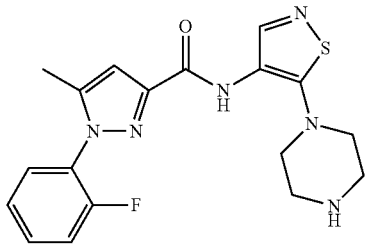 [SMILES: Cc1cc(C(=O)Nc2cnsc2N2CCNCC2)nn1-c1ccccc1F]

Following the procedure described in Example 31, and substituting Compound 19E with 1-(2-fluorophenyl)-5-methyl-1H-pyrazole-3-carboxylic acid (29E) (74 mg, 0.336 mmol), the title compound 41 (30 mg, 0.078 mmol) was obtained.

Example 42

Synthesis of 3-(2-fluorophenyl)-N-(5-(piperazin-1-yl)isothiazol-4-yl)-1H-pyrazole-5-carboxamide (42)

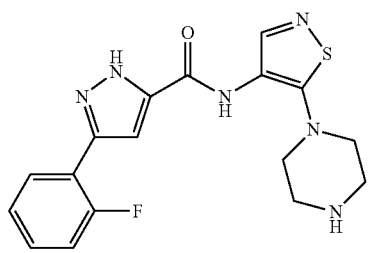 [SMILES: O=C(Nc1cnsc1N1CCNCC1)c1cc(-c2ccccc2F)n[nH]1]

Following the procedure described in Example 31, and substituting Compound 19E with 3-(2-fluorophenyl)-1H-pyrazole-5-carboxylic acid (42E) (65 mg, 0.315 mmol), the title compound 42 (30 mg, 0.080 mmol) was obtained.

Example 43

Synthesis of 2-phenyl-N-(5-(piperazin-1-yl)isothiazol-4-yl)oxazole-4-carboxamide (43)

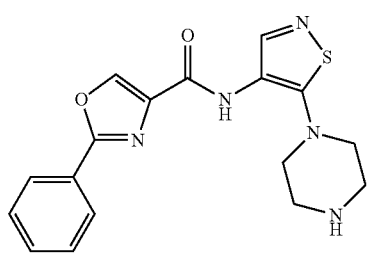 [SMILES: O=C(Nc1cnsc1N1CCNCC1)c1coc(-c2ccccc2)n1]

Following the procedure described in Example 31, and substituting Compound 19E with 2-phenyloxazole-4-carboxylic acid (30E) (64 mg, 0.34 mmol), the title compound 43 (30 mg, 0.085 mmol) was obtained.

Example 44

Synthesis of 2-(2,6-difluorophenyl)-N-(5-(4-(1-hydroxyethyl)piperidin-1-yl)isothiazol-4-yl)thiazole-4-carboxamide (44)

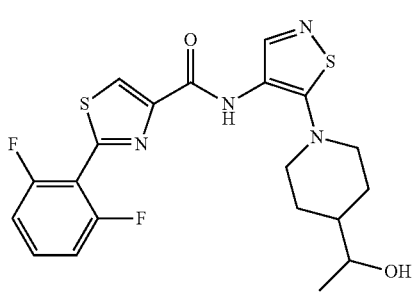 [SMILES: CC(O)C1CCN(c2sncc2NC(=O)c2csc(-c3c(F)cccc3F)n2)CC1]

Following the procedure described in Example 6, and substituting Compound 6B2 with 1-(piperidin-4-yl)ethanol (44 L) (349 mg, 1.43 mmol), the title compound 44 (50 mg, 0.111 mmol) was obtained.

Example 45

Synthesis of N-(5-(3,8-diazabicyclo[3.2.1]octan-3-yl)isothiazol-4-yl)-2-(2,6-difluorophenyl)thiazole-4-carboxamide (45)

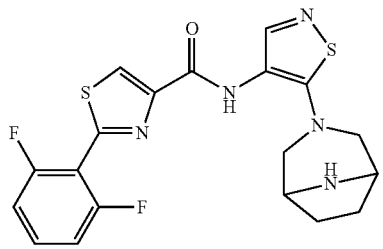 [SMILES: O=C(Nc1cnsc1N1CC2CCC(C1)N2)c1csc(-c2c(F)cccc2F)n1]

Following the procedure described in Example 6, and substituting Compound 6B2 with 8-methyl-3,8-diazabicyclo[3.2.1]octane (45 L) (62 mg, 0.29 mmol), the title compound 45 (65 mg, 0.15 mmol) was obtained.

Example 46

Synthesis of 2-(2,6-difluorophenyl)-N-(5-(piperazin-1-yl)isothiazol-4-yl)thiazole-4-carboxamide (46)

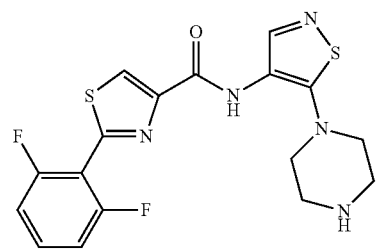 [SMILES: O=C(Nc1cnsc1N1CCNCC1)c1csc(-c2c(F)cccc2F)n1]

Following the procedure described in Example 6, and substituting Compound 6B2 with tert-butyl piperazine-1-carboxylate (46 L) (356 mg, 1.91 mmol), the title compound 46 (35 mg, 0.082 mmol) was obtained.

Example 47

Synthesis of 6-(2,6-difluorophenyl)-N-(5-(4-hydroxypiperidin-1-yl)isothiazol-4-yl)picolinamide (47)

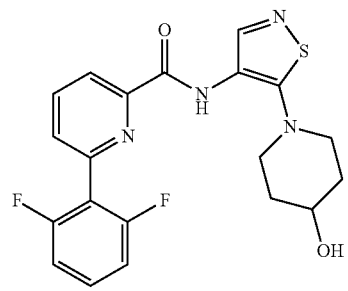

Following the procedure described in Example 8, and substituting Compound 6B2 with piperidin-4-ol (17B2) (159 mg, 1.57 mmol), the title compound 47 (65 mg, 0.156 mmol) was obtained.

Example 48

Synthesis of 2-(2,6-difluorophenyl)-N-(5-(4-hydroxyazepan-1-yl)isothiazol-4-yl)thiazole-4-carboxamide (48)

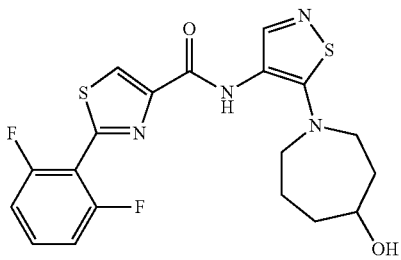 [SMILES: O=C(Nc1cnsc1N1CCCC(O)CC1)c1csc(-c2c(F)cccc2F)n1]

Following the procedure described in Example 6, and substituting Compound 6B2 with azepan-4-ol (48B2) (165 mg, 1.43 mmol), the title compound 48 (22 mg, 0.050 mmol) was obtained.

Example 49

Synthesis of 5-amino-2-(2,6-difluorophenyl)-N-(5-(4-hydroxyazepan-1-yl)isothiazol-4-yl)thiazole-4-carboxamide (49)

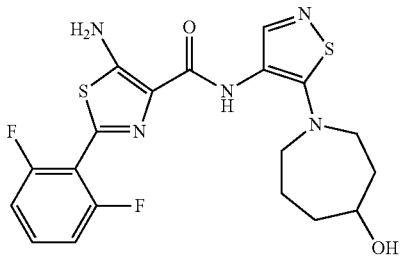 [SMILES: Nc1sc(-c2c(F)cccc2F)nc1C(=O)Nc1cnsc1N1CCCC(O)CC1]

Following the procedure described in Example 7, and substituting Compound 6B2 with azepan-4-ol (48B2) (165 mg, 1.43 mmol), the title compound 49 (8 mg, 0.018 mmol) was obtained.

Example 50

Synthesis of 6-(2,6-difluorophenyl)-N-(5-(4-hydroxyazepan-1-yl)isothiazol-4-yl)picolinamide (50)

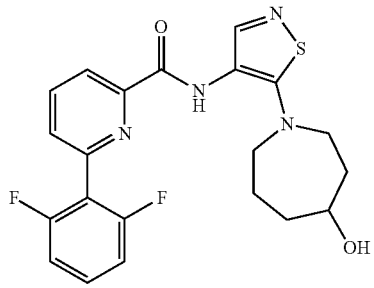

Following the procedure described in Example 8, and substituting Compound 6B2 with azepan-4-ol (48B2) (165 mg, 1.43 mmol), the title compound 50 (12 mg, 0.028 mmol) was obtained.

Example 51

Synthesis of 2-(2,6-difluorophenyl)-N-(5-(5-hydroxy-3,4-dihydroisoquinolin-2(1H)-yl)isothiazol-4-yl)thiazole-4-carboxamide (51)

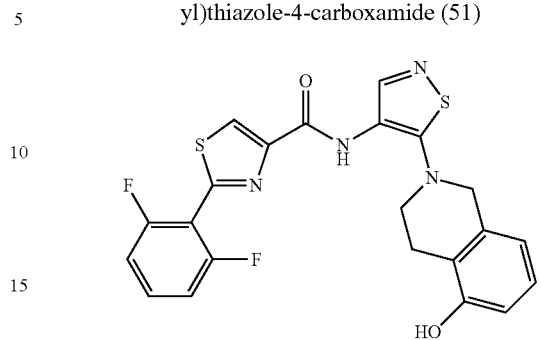

Following the procedure described in Example 6, and substituting Compound 6B2 with 1,2,3,4-tetrahydroisoquinolin-5-ol (51B2) (240 mg, 1.61 mmol), the title compound 51 (18 mg, 0.038 mmol) was obtained.

Example 52

Synthesis of 6-(2,6-difluorophenyl)-N-(5-(5-hydroxy-3,4-dihydroisoquinolin-2(1H)-yl)isothiazol-4-yl)picolinamide (52)

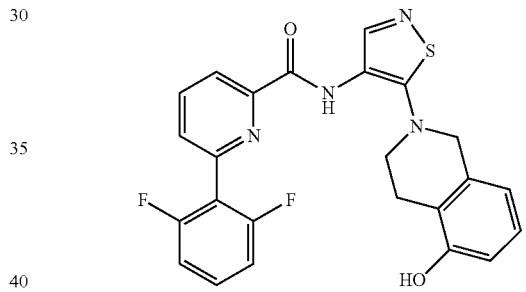

Following the procedure described in Example 8, and substituting Compound 6B2 with 1,2,3,4-tetrahydroisoquinolin-5-ol (51B2) (240 mg, 1.61 mmol), the title compound 52 (23 mg, 0.050 mmol) was obtained.

Example 53

Synthesis of (S)-2-(2,6-difluorophenyl)-N-(5-(3-(hydroxymethyl)morpholino)isothiazol-4-yl)thiazole-4-carboxamide (53)

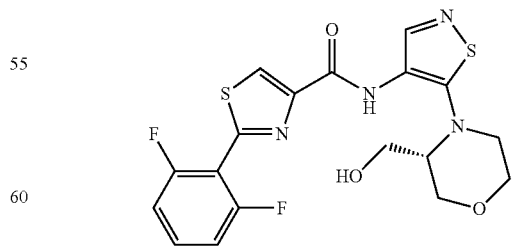

Following the procedure described in Example 6, and substituting Compound 6B2 with (S)-morpholin-3-ylmethanol (53B2) (500 mg, 4.31 mmol), the title compound 53 (18 mg, 0.041 mmol) was obtained.

Example 54

Synthesis of 2-(2,6-difluorophenyl)-N-(5-(piperidin-4-yloxy)isothiazol-4-yl)thiazole-4-carboxamide (54)

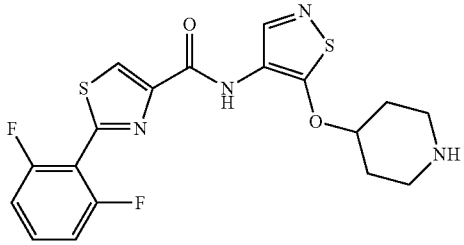 [SMILES: O=C(Nc1cnsc1OC1CCNCC1)c1csc(-c2c(F)cccc2F)n1]

Following the procedure described in Example 1, and substituting Compound 1E with 2-(2,6-difluorophenyl)thiazole-4-carboxylic acid (2E) (40 mg, 0.166 mmol), the title compound 54 (14 mg, 0.0306 mmol) was obtained.

Example 55

Synthesis of N-(5-(azetidin-3-ylmethoxy)isothiazol-4-yl)-2-(2,6-difluorophenyl)thiazole-4-carboxamide (55)

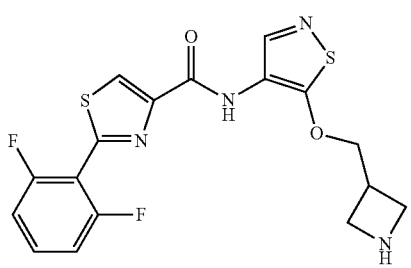 [SMILES: O=C(Nc1cnsc1OCC1CNC1)c1csc(-c2c(F)cccc2F)n1]

Following the procedure described in Example 1, and substituting Compounds 1B2 in Step (2) and 1E in Step (4) with tert-butyl 3-(hydroxymethyl)azetidine-1-carboxylate (55B2) (200 mg, 1.07 mmol) and 2-(2,6-difluorophenyl)thiazole-4-carboxylic acid (2E) (40 mg, 0.166 mmol) respectively, the title compound 55 (18 mg, 0.0441 mmol) was obtained.

Example 56

Synthesis of 3-amino-N-(5-(azetidin-3-yloxy)isothiazol-4-yl)-6-(2,6-difluorophenyl)picolinamide (56)

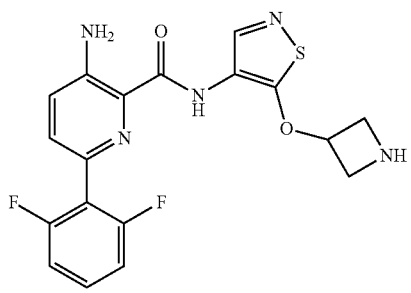 [SMILES: Nc1ccc(-c2c(F)cccc2F)nc1C(=O)Nc1cnsc1OC1CNC1]

Following the procedure described in Example 1, and substituting Compounds 1B2 in Step (2) and 1E in Step (4) with tert-butyl 3-hydroxyazetidine-1-carboxylate (56B2) (200 mg, 1.07 mmol) and 3-amino-6-(2,6-difluorophenyl)picolinic acid (56E) (40 mg, 0.166 mmol) respectively, the title compound 56 (21 mg, 0.0521 mmol) was obtained.

Example 57

Synthesis of N-(5-(azetidin-3-yloxy)isothiazol-4-yl)-2-(2,6-difluorophenyl)thiazole-4-carboxamide (57)

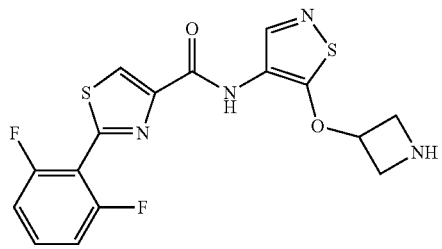 [SMILES: O=C(Nc1cnsc1OC1CNC1)c1csc(-c2c(F)cccc2F)n1]

Following the procedure described in Example 1, and substituting Compounds 1B2 in Step (2) and 1E in Step (4) with tert-butyl 3-(hydroxymethyl)azetidine-1-carboxylate (55B2) (200 mg, 1.07 mmol) and 2-(2,6-difluorophenyl)thiazole-4-carboxylic acid (2E) (40 mg, 0.166 mmol) respectively, the title compound 57 (22 mg, 0.0558 mmol) was obtained.

Example 58

Synthesis of 6-(2,6-difluorophenyl)-N-(5-(piperidin-4-yloxy)isothiazol-4-yl)-picolinamide (58)

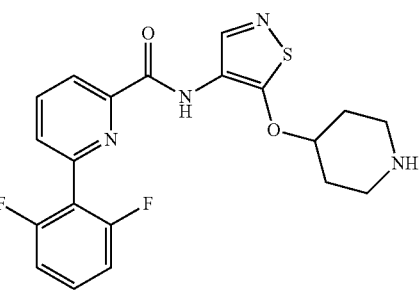

Following the procedure described in Example 1, and substituting Compound 1E with 6-(2,6-difluorophenyl)picolinic acid (4E) (40 mg 0.170 mmol), the title compound 58 (28 mg, 0.0673 mmol) was obtained.

Example 59

Synthesis of 5-amino-N-(5-((4-carbamoylcyclohexyl)oxy)isothiazol-4-yl)-2-(2,6-difluorophenyl)thiazole-4-carboxamide (59)

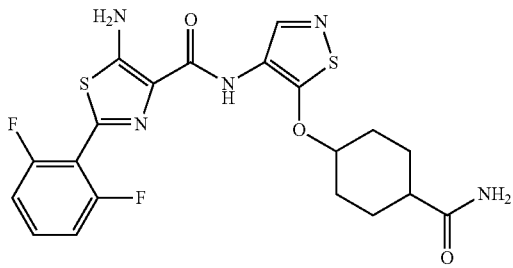 [SMILES: NC(=O)C1CCC(Oc2sncc2NC(=O)c2nc(-c3c(F)cccc3F)sc2N)CC1]

Following the procedure described in Step (1) to Step (4) of Example 1, and substituting Compound 1B2 in Step (2) with 4-hydroxycyclohexanecarboxamide (59B2) (100 mg, 0.699 mmol), the title compound 59 (10 mg, 0.0209 mmol) was obtained.

Example 60

Synthesis of 2-(2,6-difluorophenyl)-N-(5-((3-methyloxetan-3-yl)methoxy)isothiazol-4-yl)thiazole-4-carboxamide (60)

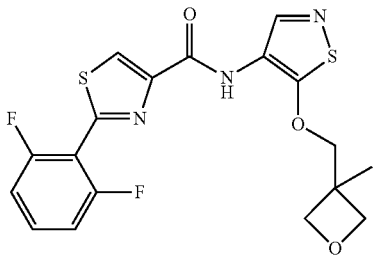 [SMILES: CC1(COc2sncc2NC(=O)c2csc(-c3c(F)cccc3F)n2)COC1]

Following the procedure described in Step (1) to Step (4) of Example 1, and substituting Compound 1B2 in Step (2) with (3-methyloxetan-3-yl)methanol (60B2) (50 mg, 0.490 mmol), the title compound 60 (22 mg, 0.0520 mmol) was obtained.

Example 61

Synthesis of 3-amino-N-(5-(3-aminopiperidin-1-yl)isothiazol-4-yl)-6-(2,6-difluorophenyl)-picolinamide (61)

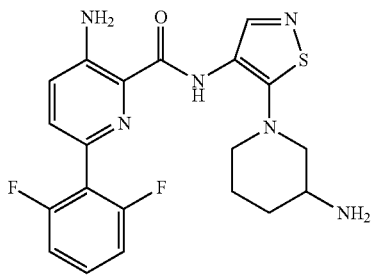 [SMILES: Nc1ccc(-c2c(F)cccc2F)nc1C(=O)Nc1cnsc1N1CCCC(N)C1]

Following the procedure described in Examples 13 and 15, and substituting Compound 2E with 3-amino-6-(2,6-difluorophenyl)picolinic acid (56E) (40 mg, 0.160 mmol), the title compound 61 (26 mg, 0.0604 mmol) was obtained.

Example 62

Synthesis of 2-(2,6-difluorophenyl)-N-(5-(piperidin-4-ylmethoxy)isothiazol-4-yl)thiazole-4-carboxamide (62)

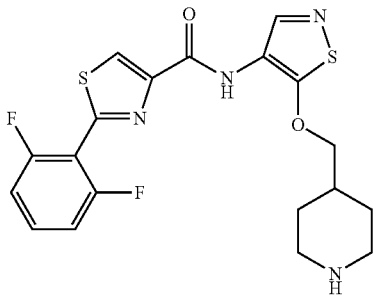 [SMILES: O=C(Nc1cnsc1OCC1CCNCC1)c1csc(-c2c(F)cccc2F)n1]

Following the procedure described in Example 1, and substituting Compounds 1B2 in Step (2) and 1E in Step (4) with tert-butyl 4-(hydroxymethyl)piperidine-1-carboxylate (62B2) (50 mg, 0.233 mmol) and 2-(2,6-difluorophenyl)thiazole-4-carboxylic acid (2E) (40 mg, 0.166 mmol) respectively, the title compound 62 (14 mg, 0.0321 mmol) was obtained.

Example 63

Synthesis of 3-amino-6-(2,6-difluorophenyl)-N-(5-(piperidin-4-ylmethoxy)isothiazol-4-yl)picolinamide (63)

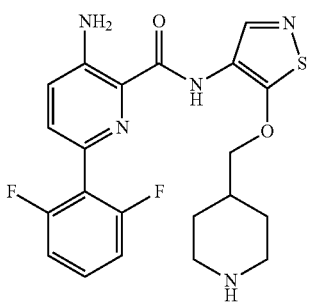 [SMILES: Nc1ccc(-c2c(F)cccc2F)nc1C(=O)Nc1cnsc1OCC1CCNCC1]

Following the procedure described in Example 1, and substituting Compounds 1B2 in Step (2) and 1E in Step (4) with tert-butyl 4-(hydroxymethyl)piperidine-1-carboxylate (62B2) (50 mg, 0.233 mmol) and 3-amino-6-(2,6-difluorophenyl)picolinic acid (56E) (40 mg, 0.160 mmol) respectively, the title compound 63 (17 mg, 0.0382 mmol) was obtained.

Example 64

Synthesis of (S)-2-(2,6-difluorophenyl)-N-(5-(pyrrolidin-3-yloxy)isothiazol-4-yl)thiazole-4-carboxamide (64)

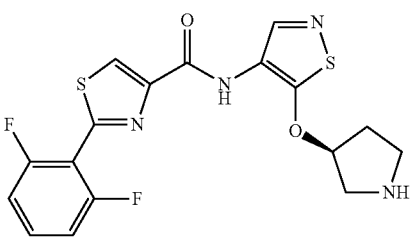 [SMILES: O=C(Nc1cnsc1O[C@H]1CCNC1)c1csc(-c2c(F)cccc2F)n1]

Following the procedure described in Example 1, and substituting Compounds 1B2 in Step (2) and 1E in Step (4) with (S)-tert-butyl 3-hydroxypyrrolidine-1-carboxylate (64B2) (50 mg, 0.267 mmol) and 2-(2,6-difluorophenyl)thiazole-4-carboxylic acid (2E) (40 mg, 0.166 mmol) respectively, the title compound 64 (19 mg, 0.0466 mmol) was obtained.

Example 65

Synthesis of (R)-2-(2,6-difluorophenyl)-N-(5-(pyrrolidin-3-yloxy)isothiazol-4-yl)thiazole-4-carboxamide (65)

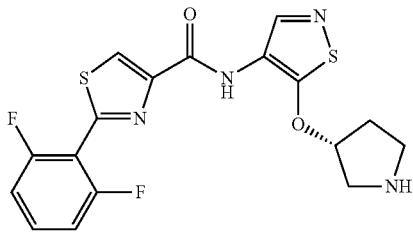 [SMILES: O=C(Nc1cnsc1O[C@@H]1CCNC1)c1csc(-c2c(F)cccc2F)n1]

Following the procedure described in Example 1, and substituting Compounds 1B2 in Step (2) and 1E in Step (4) with (R)-tert-butyl 3-hydroxypyrrolidine-1-carboxylate (50 mg, 0.267 mmol) and 2-(2,6-difluorophenyl)thiazole-4-carboxylic acid (2E) (40 mg, 0.166 mmol) respectively, the title compound 65 (18 mg, 0.0441 mmol) was obtained.

Example 66

Synthesis of 5-amino-N-(5-(3-aminopiperidin-1-yl)isothiazol-4-yl)-2-(2,6-difluorophenyl)thiazole-4-carboxamide (66)

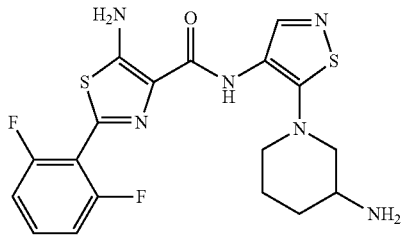 [SMILES: Nc1sc(-c2c(F)cccc2F)nc1C(=O)Nc1cnsc1N1CCCC(N)C1]

Following the procedure described in Example 14, and substituting Compound 13 with tert-butyl (1-(4-(5-amino-2-(2,6-difluorophenyl)thiazole-4-carboxamido)isothiazol-5-yl)piperidin-3-yl)carbamate (15) (40 mg, 0.0746 mmol), the title compound 66 (28 mg, 0.0642 mmol) was obtained.

Example 67

Synthesis of 2-(2,6-difluorophenyl)-N-(5-(3-hydroxypiperidin-1-yl)isothiazol-4-yl)thiazole-4-carboxamide (67)

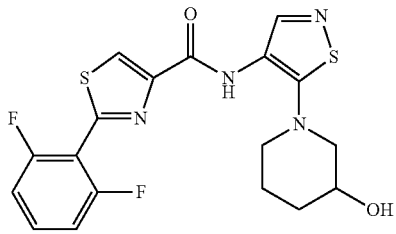 [SMILES: O=C(Nc1cnsc1N1CCCC(O)C1)c1csc(-c2c(F)cccc2F)n1]

Following the procedure described in Example 6, and substituting Compound 6B2 with piperidin-3-ol (67B2) (50 mg, 0.495 mmol), the title compound 67 (9 mg, 0.0211 mmol) was obtained.

Example 68

Synthesis of 5-amino-2-(2,6-difluorophenyl)-N-(5-(3-hydroxypiperidin-1-yl)isothiazol-4-yl)thiazole-4-carboxamide (68)

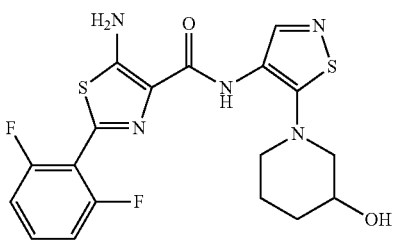 [SMILES: Nc1sc(-c2c(F)cccc2F)nc1C(=O)Nc1cnsc1N1CCCC(O)C1]

Following the procedure described in Example 67, and substituting Compound 2E with 5-amino-2-(2,6-difluorophenyl)thiazole-4-carboxylic acid (1E) (70 mg, 0.273 mmol), the title compound 68 (10 mg, 0.0229 mmol) was obtained.

Example 69

Synthesis of (S)-5-amino-2-(2,6-difluorophenyl)-N-(5-(pyrrolidin-3-yloxy)isothiazol-4-yl)thiazole-4-carboxamide (69)

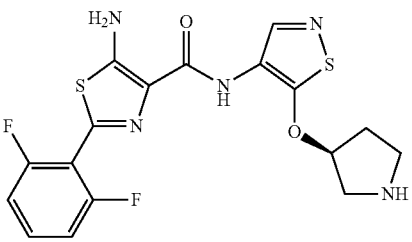 [SMILES: Nc1sc(-c2c(F)cccc2F)nc1C(=O)Nc1cnsc1O[C@H]1CCNC1]

Following the procedure described in Example 64, and substituting Compound 2E with 5-amino-2-(2,6-difluorophenyl)thiazole-4-carboxylic acid (1E) (70 mg, 0.273 mmol), the title compound 69 (31 mg, 0.0733 mmol) was obtained.

Example 70

Synthesis of (R)-5-amino-2-(2,6-difluorophenyl)-N-(5-(pyrrolidin-3-yloxy)isothiazol-4-yl)thiazole-4-carboxamide (70)

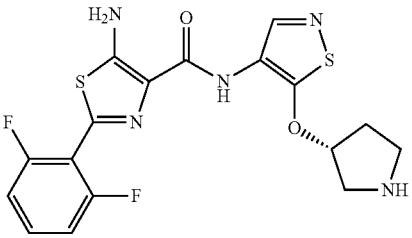 [SMILES: Nc1sc(-c2c(F)cccc2F)nc1C(=O)Nc1cnsc1O[C@@H]1CCNC1]

Following the procedure described in Example 65, and substituting Compound 2E with 5-amino-2-(2,6-difluorophenyl)thiazole-4-carboxylic acid (1E) (70 mg, 0.273 mmol), the title compound 70 (29 mg, 0.0686 mmol) was obtained.

Example 71

Synthesis of 3-amino-6-(2,6-difluorophenyl)-N-(5-(3-hydroxypiperidin-1-yl)isothiazol-4-yl)picolinamide (71)

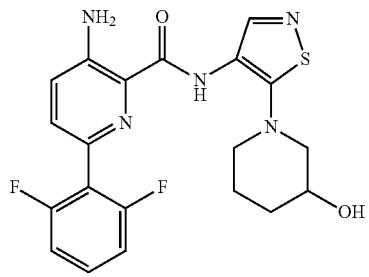 [SMILES: Nc1ccc(-c2c(F)cccc2F)nc1C(=O)Nc1cnsc1N1CCCC(O)C1]

Following the procedure described in Example 67, and substituting Compound 2E with 3-amino-6-(2,6-difluorophenyl)picolinic acid (56E) (50 mg, 0.200 mmol), the title compound 71 (14 mg, 0.0324 mmol) was obtained.

Example 72

Synthesis of 6-(2,6-difluorophenyl)-N-(5-(3-hydroxypiperidin-1-yl)isothiazol-4-yl)picolinamide (72)

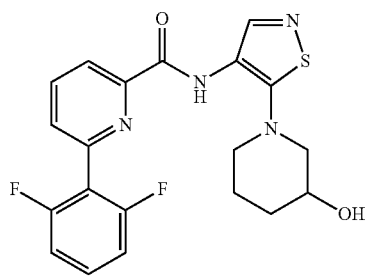 [SMILES: O=C(Nc1cnsc1N1CCCC(O)C1)c1cccc(-c2c(F)cccc2F)n1]

Following the procedure described in Example 67, and substituting Compound 2E with 6-(2,6-difluorophenyl)picolinic acid (4E) (50 mg, 0.200 mmol), the title compound 72 (15 mg, 0.0361 mmol) was obtained.

Example 73

Synthesis of 5-amino-N-(5-(azepan-4-yloxy)isothiazol-4-yl)-2-(2,6-difluorophenyl)thiazole-4-carboxamide (73)

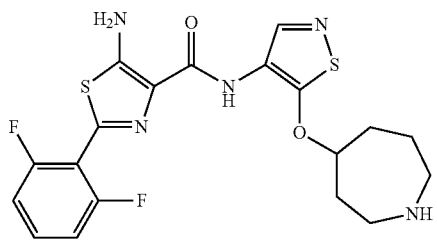 [SMILES: Nc1sc(-c2c(F)cccc2F)nc1C(=O)Nc1cnsc1OC1CCCNCC1]

Following the procedure described in Example 1, and substituting Compound 1B2 in Step (2) with tert-butyl 4-hydroxyazepane-1-carboxylate (2B2) (100 mg, 0.47 mmol), the title compound 73 (26 mg, 0.0576 mmol) was obtained.

Example 74

Synthesis of 3-amino-6-(2,6-difluorophenyl)-N-(5-(3-hydroxypropoxy)isothiazol-4-yl)picolinamide (74)

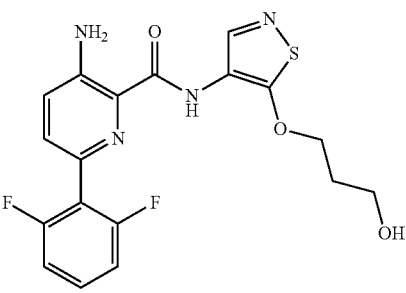 [SMILES: Nc1ccc(-c2c(F)cccc2F)nc1C(=O)Nc1cnsc1OCCCO]

Following the procedure described in Example 1, and substituting Compounds 1B2 in Step (2) and 1E in Step (4) with 3-((trimethylsilyl)oxy)propan-1-ol (74B2) (100 mg, 0.676 mmol) and 3-amino-6-(2,6-difluorophenyl)picolinic acid (56E) respectively, the title compound 74 (25 mg, 0.0616 mmol) was obtained.

Example 75

Synthesis of 5-amino-N-(5-((trans-4-aminocyclohexyl)oxy)isothiazol-4-yl)-2-(2,6-difluorophenyl)thiazole-4-carboxamide (75)

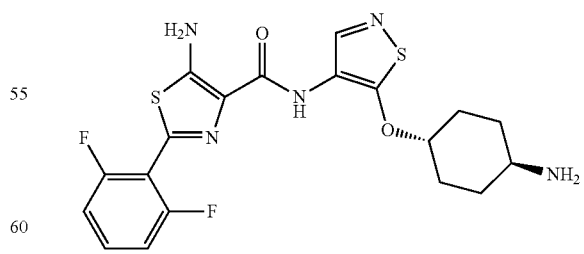

Following the procedure described in Example 1, and substituting Compound 1B2 in Step (2) with tert-butyl (trans-4-hydroxycyclohexyl)carbamate (75B2) (100 mg, 0.465 mmol), the title compound 75 (11 mg, 0.0244 mmol) was obtained.

Example 76

Synthesis of 5-amino-2-(2,6-difluorophenyl)-N-(5-(piperidin-4-ylmethoxy)isothiazol-4-yl)thiazole-4-carboxamide (76)

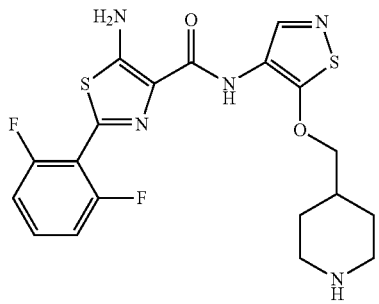 [SMILES: Nc1sc(-c2c(F)cccc2F)nc1C(=O)Nc1cnsc1OCC1CCNCC1]

Following the procedure described in Example 1, and substituting Compound 1B2 in Step (2) with tert-butyl 4-(hydroxymethyl)piperidine-1-carboxylate (62B2) (100 mg, 0.465 mmol), the title compound 76 (22 mg, 0.0488 mmol) was obtained.

Example 77

Synthesis of 5-amino-N-(5-(4-aminobutoxy)isothiazol-4-yl)-2-(2,6-difluorophenyl)thiazole-4-carboxamide (77)

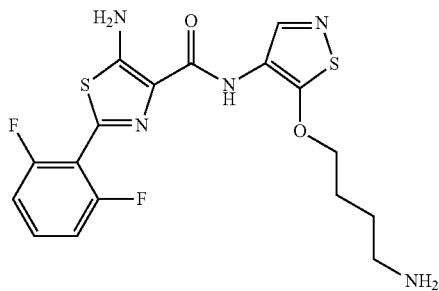 [SMILES: NCCCCOc1sncc1NC(=O)c1nc(-c2c(F)cccc2F)sc1N]

Following the procedure described in Example 1, and substituting Compound 1B2 in Step (2) with tert-butyl (4-hydroxybutyl)carbamate (77B2) (100 mg, 0.529 mmol), the title compound 77 (24 mg, 0.0531 mmol) was obtained.

Example 78

Synthesis of 5-amino-2-(2,6-difluorophenyl)-N-(5-(4-hydroxybutoxy)isothiazol-4-yl)thiazole-4-carboxamide (78)

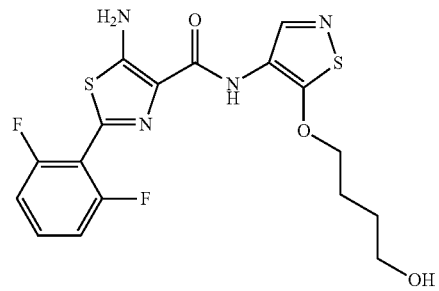 [SMILES: Nc1sc(-c2c(F)cccc2F)nc1C(=O)Nc1cnsc1OCCCCO]

Following the procedure described in Example 1, and substituting Compound 1B2 in Step (2) with 4-((trimethylsilyl)oxy)butan-1-ol (78B2) (100 mg, 0.617 mmol), the title compound 78 (29 mg, 0.0681 mmol) was obtained.

Example 79

Synthesis of 5-amino-2-(2,6-difluorophenyl)-N-(5-(2-hydroxyethoxy)isothiazol-4-yl)thiazole-4-carboxamide (79)

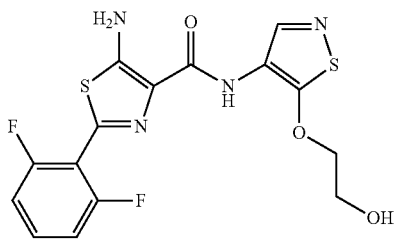 [SMILES: Nc1sc(-c2c(F)cccc2F)nc1C(=O)Nc1cnsc1OCCO]

Following the procedure described in Example 1, and substituting Compound 1B2 in Step (2) with 2-((trimethylsilyl)oxy)ethanol (79B2) (100 mg, 0.746 mmol), the title compound 79 (31 mg, 0.0779 mmol) was obtained.

Example 80

Synthesis of 5-amino-2-(2,6-difluorophenyl)-N-(5-(3-hydroxypropoxy)isothiazol-4-yl)thiazole-4-carboxamide (80)

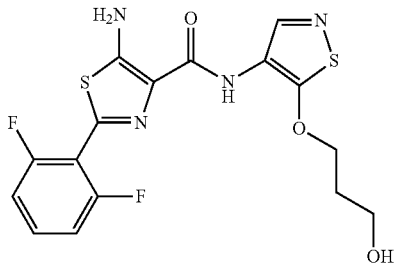 [SMILES: Nc1sc(-c2c(F)cccc2F)nc1C(=O)Nc1cnsc1OCCCO]

Following the procedure described in Example 1, and substituting Compound 1B2 in Step (2) with 3-((trimethylsilyl)oxy)propan-1-ol (74B2) (100 mg, 0.676 mmol), the title compound 80 (37 mg, 0.0655 mmol) was obtained.

Example 81

Synthesis of 5-amino-2-(2,6-difluorophenyl)-N-(5-(3-hydroxypropoxy)isothiazol-4-yl)thiazole-4-carboxamide (81)

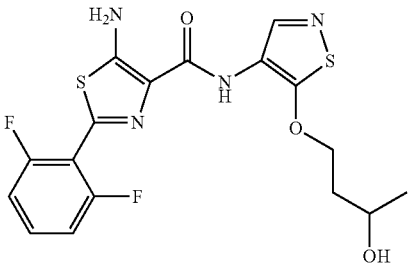 [SMILES: CC(O)CCOc1sncc1NC(=O)c1nc(-c2c(F)cccc2F)sc1N]

Following the procedure described in Step (1) to Step (4) of Example 1, and substituting Compound 1B2 in Step (2) with butane-1,3-diol (81B2) (50 mg, 0.556 mmol), the title compound 81 (12 mg, 0.0280 mmol) was obtained.

Example 82

Synthesis of 5-amino-2-(2,6-difluorophenyl)-N-(5-(3-hydroxy-3-methylbutoxy)isothiazol-4-yl)thiazole-4-carboxamide (82)

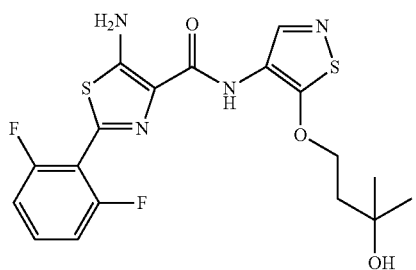 [SMILES: CC(C)(O)CCOc1sncc1NC(=O)c1nc(-c2c(F)cccc2F)sc1N]

Following the procedure described in Step (1) to Step (4) of Example 1, and substituting Compound 1B2 in Step (2) with 3-methylbutane-1,3-diol (82B2) (50 mg, 0.480 mmol), the title compound 82 (25 mg, 0.0568 mmol) was obtained.

Example 83

Synthesis of 2-(2,6-difluorophenyl)-5-formamido-N-(5-((4-hydroxy-4-methylpentyl)oxy)isothiazol-4-yl)thiazole-4-carboxamide (83)

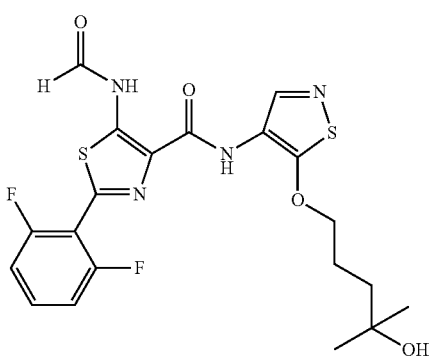 [SMILES: CC(C)(O)CCCOc1sncc1NC(=O)c1nc(-c2c(F)cccc2F)sc1NC=O]

Following the procedure described in Step (1) to Step (4) of Example 1, and substituting Compounds 1B2 in Step (2) and 1E in Step (4) with 4-methylpentane-1,4-diol (83B2) (50 mg, 0.424 mmol) and 2-(2,6-difluorophenyl)-5-formamidothiazole-4-carboxylic acid (83E) respectively, the title compound 83 (8 mg, 0.0166 mmol) was obtained.

Example 84

Synthesis of 5-amino-2-(2,6-difluorophenyl)-N-(5-((4-hydroxypentyl)oxy)isothiazol-4-yl)thiazole-4-carboxamide (84)

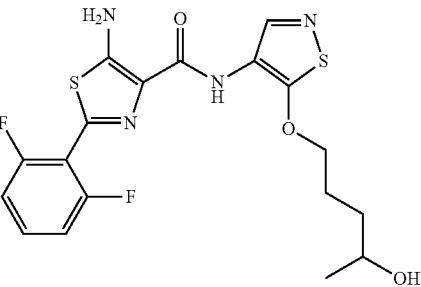

Following the procedure described in Step (1) to Step (4) of Example 1, and substituting Compound 1B2 in Step (2) with pentane-1,4-diol (84B2) (50 mg, 0.480 mmol), the title compound 84 (18 mg, 0.0409 mmol) was obtained.

Example 85

Synthesis of 2-(2,6-difluorophenyl)-N-(5-((4-hydroxypentyl)oxy)isothiazol-4-yl)thiazole-4-carboxamide (85)

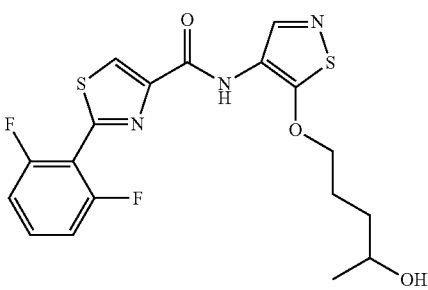 [SMILES: CC(O)CCCOc1sncc1NC(=O)c1csc(-c2c(F)cccc2F)n1]

Following the procedure described in Step (1) to Step (4) of Example 1, and substituting Compounds 1B2 in Step (2) and 1E in Step (4) with pentane-1,4-diol (84B2) (50 mg, 0.480 mmol) and 2-(2,6-difluorophenyl)thiazole-4-carboxylic acid (2E) respectively, the title compound 85 (28 mg, 0.0659 mmol) was obtained.

Example 86

Synthesis of 5-amino-2-(2,6-difluorophenyl)-N-(5-((4-hydroxy-4-methylpentyl)oxy)isothiazol-4-yl)thiazole-4-carboxamide (86)

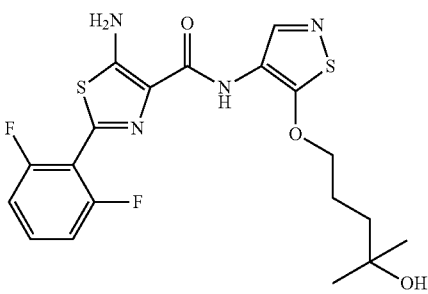 [SMILES: CC(C)(O)CCCOc1sncc1NC(=O)c1nc(-c2c(F)cccc2F)sc1N]

Following the procedure described in Step (1) to Step (4) of Example 1, and substituting Compound 1B2 in Step (2) with 4-methylpentane-1,4-diol (83B2) (50 mg, 0.424 mmol), the title compound 86 (31 mg, 0.0683 mmol) was obtained.

Example 87

Synthesis of 2-(2,6-difluorophenyl)-N-(5-((4-hydroxy-4-methylpentyl)oxy)isothiazol-4-yl)thiazole-4-carboxamide (87)

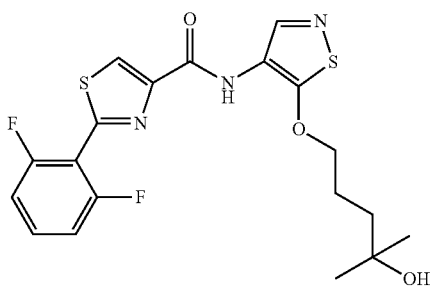 [SMILES: CC(C)(O)CCCOc1sncc1NC(=O)c1csc(-c2c(F)cccc2F)n1]

Following the procedure described in Step (1) to Step (4) of Example 1, and substituting Compounds 1B2 in Step (2) and 1E in Step (4) with 4-methylpentane-1,4-diol (83B2) (50 mg, 0.424 mmol) and 2-(2,6-difluorophenyl)thiazole-4-carboxylic acid (2E) respectively, the title compound 87 (23 mg, 0.0524 mmol) was obtained.

Example 88

Synthesis of 5-amino-2-(2,6-difluorophenyl)-N-(5-(2-(2,2-dimethyl-1,3-dioxolan-4-yl)ethoxy)isothiazol-4-yl)thiazole-4-carboxamide (88)

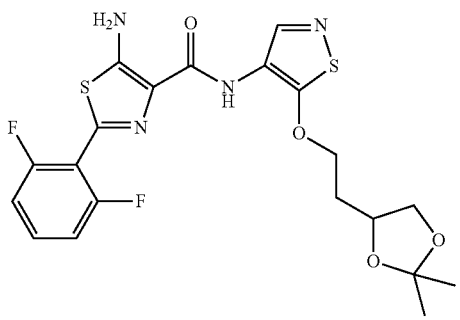 [SMILES: CC1(C)OCC(CCOc2sncc2NC(=O)c2nc(-c3c(F)cccc3F)sc2N)O1]

Following the procedure described in Step (1) to Step (4) of Example 1, and substituting Compound 1B2 in Step (2) with 2-(2,2-dimethyl-1,3-dioxolan-4-yl)ethanol (88B2) (50 mg, 0.342 mmol), the title compound 88 (34 mg, 0.0705 mmol) was obtained.

Example 89

Synthesis of 5-amino-2-(2,6-difluorophenyl)-N-(5-((2,2-dimethyl-1,3-dioxolan-4-yl)methoxy)isothiazol-4-yl)thiazole-4-carboxamide (89)

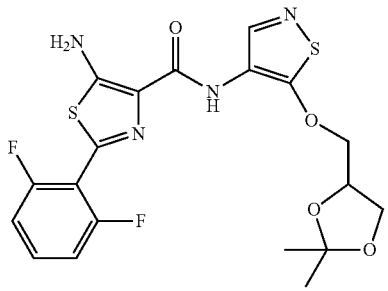 [SMILES: CC1(C)OCC(COc2sncc2NC(=O)c2nc(-c3c(F)cccc3F)sc2N)O1]

Following the procedure described in Step (1) to Step (4) of Example 1, and substituting Compound 1B2 in Step (2) with (2,2-dimethyl-1,3-dioxolan-4-yl)methanol (89B2) (50 mg, 0.379 mmol), the title compound 89 (37 mg, 0.0791 mmol) was obtained.

Example 90

Synthesis of 5-amino-2-(2,6-difluorophenyl)-N-(5-(2,3-dihydroxyprop oxy)isothiazol-4-yl)thiazole-4-carboxamide (90)

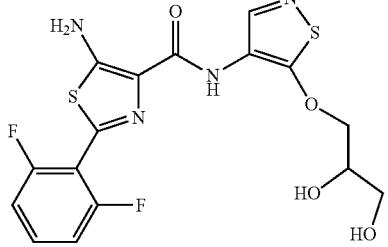

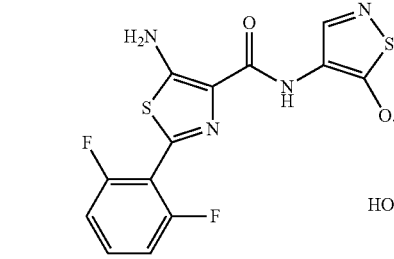

To a solution of 5-amino-2-(2,6-difluorophenyl)-N-(5-((2,2-dimethyl-1,3-dioxolan-4-yl)methoxy)isothiazol-4-yl)thiazole-4-carboxamide (89) (20 mg, 0.0427 mmol) in methanol (1 mL) at room temperature (25° C.) was added concentrated HCl (0.5 mL). The solution was stirred for 30 min and then concentrated in vacuo to afford the title compound 89 (12 mg, 0.0280 mmol)

Example 91

Synthesis of 5-amino-2-(2,6-difluorophenyl)-N-(5-(3,4-dihydroxybutoxy)isothiazol-4-yl)thiazole-4-carboxamide (91)

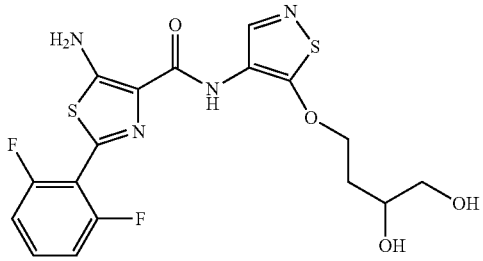 [SMILES: Nc1sc(-c2c(F)cccc2F)nc1C(=O)Nc1cnsc1OCCC(O)CO]

Following the procedure described in Example 89, and substituting Compound 89 with 5-amino-2-(2,6-difluorophenyl)-N-(5-(2-(2,2-dimethyl-1,3-dioxolan-4-yl)ethoxy)isothiazol-4-yl)thiazole-4-carboxamide (88) (20 mg, 0.415 mmol), the title compound 91 (14 mg, 0.0317 mmol) was obtained.

Example 92

Synthesis of 2-(2,6-difluorophenyl)-N-(5-(3,4-dihydroxybutoxy)isothiazol-4-yl)thiazole-4-carboxamide (92)

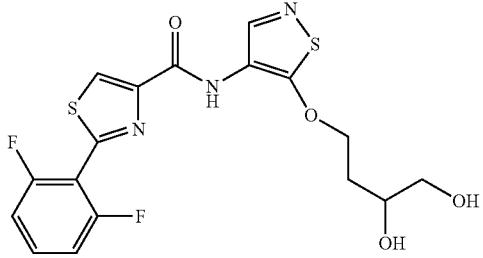 [SMILES: O=C(Nc1cnsc1OCCC(O)CO)c1csc(-c2c(F)cccc2F)n1]

Following the procedure described in Examples 88 and 91, and substituting Compound 1E with 2-(2,6-difluorophenyl)thiazole-4-carboxylic acid (2E) (50 mg, 0.207 mmol), the title compound 92 (7 mg, 0.016 mmol) was obtained.

Example 93

Synthesis of 5-amino-N-(5-(3-aminopropoxy)isothiazol-4-yl)-2-(2,6-difluorophenyl)thiazole-4-carboxamide (93)

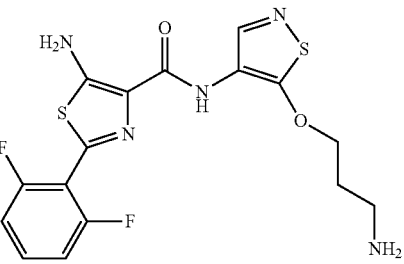 [SMILES: NCCCOc1sncc1NC(=O)c1nc(-c2c(F)cccc2F)sc1N]

Following the procedure described in Example 1, and substituting Compound 1B2 in Step (2) with tert-butyl (3-hydroxypropyl)carbamate (93B2) (50 mg, 0.286 mmol), the title compound 93 (9 mg, 0.022 mmol) was obtained.

Example 94

Synthesis of 5-amino-2-(2,6-difluorophenyl)-N-(5-(3-(methylamino)propoxy)isothiazol-4-yl)thiazole-4-carboxamide (94)

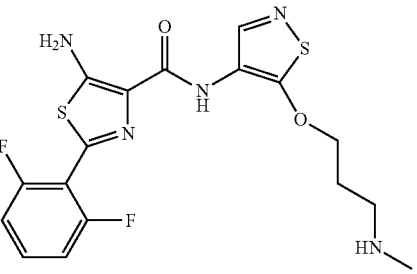 [SMILES: CNCCCOc1sncc1NC(=O)c1nc(-c2c(F)cccc2F)sc1N]

Following the procedure described in Example 1, and substituting Compound 1B2 in Step (2) with tert-butyl (3-hydroxypropyl)(methyl)carbamate (94B2) (50 mg, 0.286 mmol), the title compound 94 (9 mg, 0.0219 mmol) was obtained.

Example 95

Synthesis of 5-amino-2-(2,6-difluorophenyl)-N-(5-(4-(methylamino)butoxy)isothiazol-4-yl)thiazole-4-carboxamide (95)

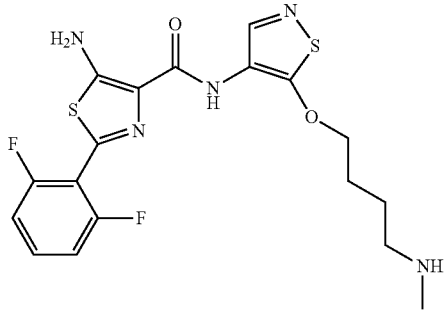 [SMILES: CNCCCCOc1sncc1NC(=O)c1nc(-c2c(F)cccc2F)sc1N]

Following the procedure described in Example 1, and substituting Compound 1B2 in Step (2) with tert-butyl (4-hydroxybutyl)(methyl)carbamate (95B2) (50 mg, 0.246 mmol), the title compound 95 (11 mg, 0.0542 mmol) was obtained.

Example 96

Synthesis of 2-(2,6-difluorophenyl)-N-(5-((4-hydroxy-4-methylpentyl)oxy)isothiazol-4-yl)-5-(methylamino)thiazole-4-carboxamide (96)

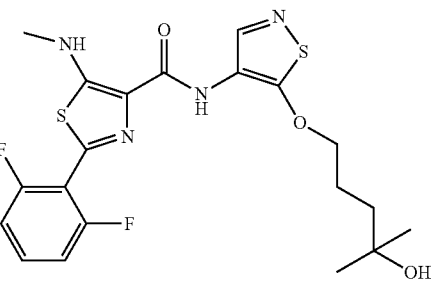

Following the procedure described in Example 1, and substituting Compounds 1B2 in Step (2) and 1E in Step (4) with 4-methylpentane-1,4-diol (83B2) (50 mg, 0.424 mmol) and 2-(2,6-difluorophenyl)-5-(methylamino)thiazole-4-carboxylic acid (96E) respectively, the title compound 96 (13 mg, 0.0278 mmol) was obtained.

Analytical data of the compound described in the examples of the present invention:

| | Structure | $^1$HNMR | MS |
|---|---|---|---|
| 1 | 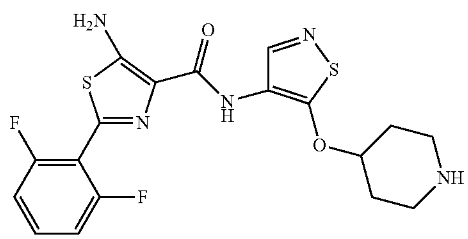 [SMILES: Nc1sc(-c2c(F)cccc2F)nc1C(=O)Nc1cnsc1OC1CCNCC1] | $^1$H NMR (400 MHz, DMSO-d6) δ 1.82-1.91 (m, 2H), 2.14-2.20 (m, 2H), 3.13-3.17-(m, 2H), 3.28 (m, 2H), 4.46-4.51 (m, 1H), 7.27 (t, 2H), 7.50-7.59 (m, 3H), 8.65 (m, 3H), 9.04 (s, 1H), | M + 1: 438 |
| 2 | 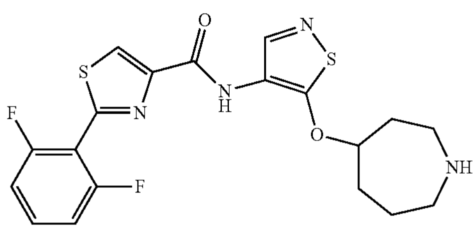 [SMILES: O=C(Nc1cnsc1OC1CCCNCC1)c1csc(-c2c(F)cccc2F)n1] | $^1$H NMR (400 MHz, DMSO-d6) δ 1.69-1.78 (m, 1H), 1.85-1.94 (m, 2H), 2.0-2.13 (m, 2H), 2.19-2.27 (m, 2H), 3.13 (m, 3H), 3.22-3.24 (m, 1H), 4.57-4.62 (m, 1H), 7.37-7.40(m, 2H), 7.64-7.73(m, 1H), 8.55 (s, 1H), 8.64 (bs, 1H), 8.70 (s, 1H), 9.75(s, 1H), | M + 1: 452 |
| 3 | 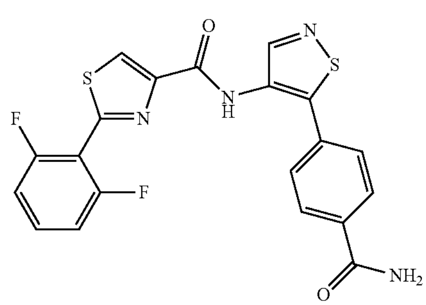 [SMILES: NC(=O)c1ccc(-c2sncc2NC(=O)c2csc(-c3c(F)cccc3F)n2)cc1] | $^1$H NMR (400 MHz, DMSO-d$_6$) 7.36 (m, 3H), 7.47(m, 1H), 7.704-7.721(d, J = 6.8 Hz, 2H), 7.980-7.997(d, J = 6.8 Hz, 2H), 8.07(m, 1H), 8.73 (s, 1H), 8.88 (s, 1H), 10.31 (s, 1H), | M: 437 |

-continued

| | Structure | ¹HNMR | MS |
|---|---|---|---|
| 4 | 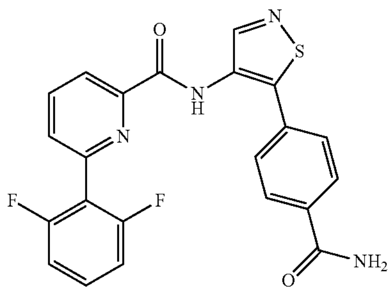 [SMILES: NC(=O)c1ccc(-c2sncc2NC(=O)c2cccc(-c3c(F)cccc3F)n2)cc1] | ¹H NMR (400 MHz, DMSO-d₆) δ 7.28-7.30 (m, 2H), 7.47(s, 1H), 7.52 (m, 1H), 7.696-7.713 (d, J = 6.8 Hz, 2H), 7.980-7.997 (d, J = 6.8 Hz, 2H), 7.82 (m, 1H), 7.98-7.99 (d, J = 6.8 Hz, 2H), 8.02 (s, 1H), 8.208-8.23 (m, 2H), 9.08 (s, 1H), 10.60 (s, 1H), | M + 23: 459 |
| 5 | 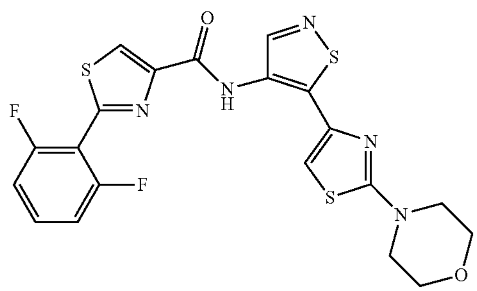 [SMILES: O=C(Nc1cnsc1-c1csc(N2CCOCC2)n1)c1csc(-c2c(F)cccc2F)n1] | ¹H NMR (400 MHz, DMSO-d₆) δ 3.24-3.26 (t, J = 3.6 Hz, 4H), 3.359-3.378(t, J = 3.6 Hz, 4H), 7.41-7.44 (m, 3H), 7.74 (m, 1H), 8.84 (s, 1H), 9.41 (s, 1H), 11.39 (s, 1H), | M + 39: 530 |
| 6 | 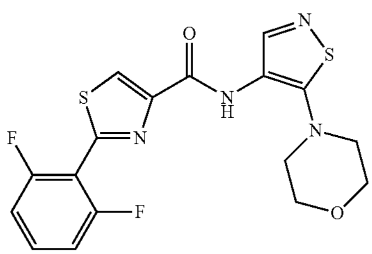 [SMILES: O=C(Nc1cnsc1N1CCOCC1)c1csc(-c2c(F)cccc2F)n1] | ¹H NMR (400 MHz, CDCl₃) δ 3.15-3.17 (t, J = 3.6 Hz, 4H), 3.91-3.93(t, J = 3.6 Hz, 4H), 7.12 (m, 2H), 7.49 (m, 1H), 8.39 (s, 1H), 9.10 (s, 1H), 9.20 (s, 1H), | M: 408 |
| 7 | 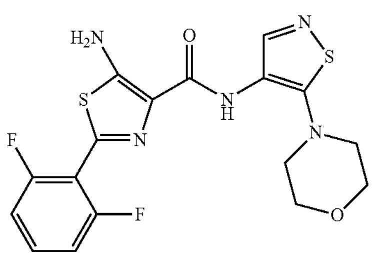 [SMILES: Nc1sc(-c2c(F)cccc2F)nc1C(=O)Nc1cnsc1N1CCOCC1] | ¹H NMR (400 MHz, CDCl₃) δ 3.14-3.16 (t, J = 3.6 Hz, 4H), 4.11-4.13 (t, J = 3.6 Hz, 4H), 6.17 (s, 2H), 7.02-7.06 (m, 2H), 7.32-7.36 (m, 1H), 8.71 (s, 1H), 9.00 (s, 1H), | M − 1: 422 |
| 8 | 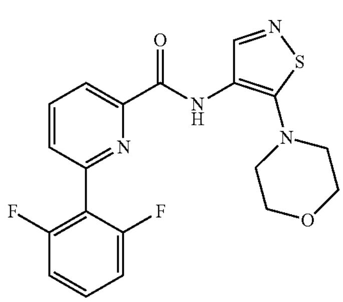 [SMILES: O=C(Nc1cnsc1N1CCOCC1)c1cccc(-c2c(F)cccc2F)n1] | ¹H NMR (400 MHz, CDCl₃) δ 3.13-3.15 (t, J = 3.6 Hz, 4H), 3.82-3.84 (t, J = 3.6 Hz, 4H), 7.07 (m, 2H), 7.46 (m, 1H), 7.74-7.75 (d, J = 4 Hz, 1H), 8.02-8.05 (t, J = 4.0 Hz, 1H), 8.29-8.30 (d, J = 4.0 Hz, 1H), 9.14 (s, 1H), 9.86 (s, 1H), | M: 402 |

-continued

| | Structure | ¹HNMR | MS |
|---|---|---|---|
| 9 | 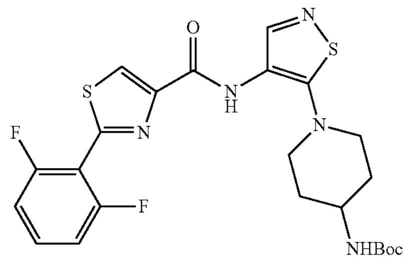 [SMILES: CC(C)(C)OC(=O)NC1CCN(c2sncc2NC(=O)c2csc(-c3c(F)cccc3F)n2)CC1] | ¹H NMR (400 MHz, CDCl₃) δ 1.25 (s, 3H), 1.67-1.68 (m, 2H), 2.06-2.08 (m, 2H), 2.97 (m, 2H), 3.41 (m, 2 H), 3.75 (m, 1H), 4.60 (s, 1H), 7.12-7.14 (m, 2H), 7.46 (m, 1H), 8.40(s, 1H), 9.02 (s, 1H), 9.10 (s, 1H), | M: 521 |
| 10 | 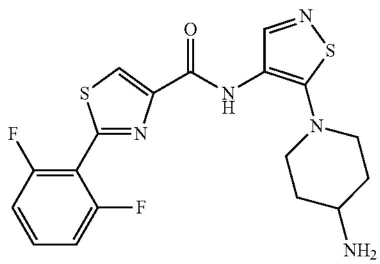 [SMILES: NC1CCN(c2sncc2NC(=O)c2csc(-c3c(F)cccc3F)n2)CC1] | ¹H NMR (400 MHz, DMSO-d₆) δ 1.67-1.70 (m, 2H), 1.93-1.94 (m, 2H), 2.98 (m, 2H), 3.15-3.16 (m, 1 H), 3.63-3.66 (m, 2H), 7.37 (m, 2H), 7.68 (m, 1H), 8.16-8.18(bs, 1H), 8.29 (s, 1H), 8.71 (s, 1H), 9.78 (s, 1H) | M + 1: 422 |
| 11 | 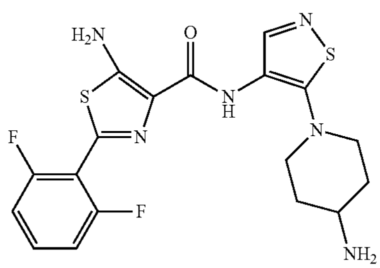 [SMILES: Nc1sc(-c2c(F)cccc2F)nc1C(=O)Nc1cnsc1N1CCC(N)CC1] | ¹H NMR (400 MHz, DMSO-d₆) δ 1.72-1.75 (m, 2H), 2.00-2.01 (m, 2H), 2.93 (m, 2H), 3.16-3.17 (m, 1 H), 3.56-3.57 (m, 2H), 7.29-7.31 (m, 2H), 7.54-7.56 (m, 1H), 7.63 (m, 2H), 8.46 (m, 4H), 8.92 (s, 1H), | M + 1: 437 |
| 12 | 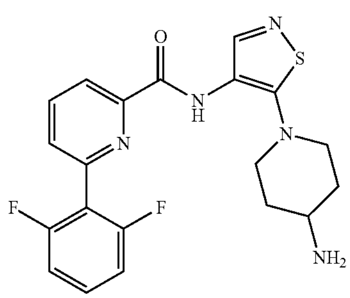 [SMILES: NC1CCN(c2sncc2NC(=O)c2cccc(-c3c(F)cccc3F)n2)CC1] | ¹H NMR (400 MHz, CD₃OD-d₄) δ 1.62-1.65 (m, 2H), 1.89 (m, 2H), 2.96-2.97 (m, 3H), 3.31-3.34 (m, 2 H), 3.63-3.66 (m, 2H), 7.18 (m, 2H), 7.54 (m, 1H), 7.82-7.84 (d, J = 5.6 Hz, 1H), 8.16-8.18 (t, J = 5.6 Hz, 1H), 8.23 (d, J = 5.6 Hz, 1H), 8.61 (s, 1H), | M + 1: 416 |
| 13 | 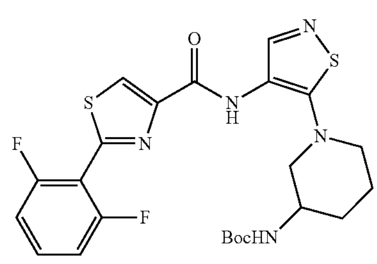 [SMILES: CC(C)(C)OC(=O)NC1CCCN(c2sncc2NC(=O)c2csc(-c3c(F)cccc3F)n2)C1] | ¹H NMR (400 MHz, CDCl₃) δ 1.25-1.28 (m, 2H), 1.39 (s, 9H), 1.58 (m, 2H), 2.80 (m, 5H), 7.09-7.13 (m, 3H), 7.45 (m, 1H), 8.40 (s, 1H), 8.94 (s, 1H), 9.14(s, 1H) | M + 1: 522 |
| 14 | 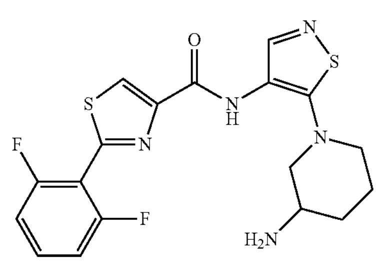 [SMILES: NC1CCCN(c2sncc2NC(=O)c2csc(-c3c(F)cccc3F)n2)C1] | ¹H NMR (400 MHz, MeOD-d₄) δ 1.56-2.15 (m, 4H), 2.95-3.22 (m, 2 H), 3.35-3.46 (m, 2H), 3.50-3.65 (m, 1 H), 4.30-4.66 (m, 3H), 7.12-7.34 (m, 2H), 7.48-7.72 (m, 1H), 8.48-8.56 (m, 1H), 8.57-8.64 (m, 1H) | M + 1: 422 |

-continued
| | Structure | ¹HNMR | MS |
|---|---|---|---|
| 15 | 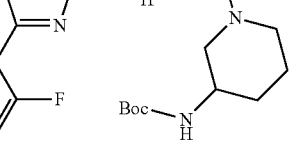 | ¹H NMR (400 MHz, MeOD-d₄) δ 1.30-1.36 (m, 1H), 1.39 (s, 9H), 1.66-2.07 (m, 3 H), 2.65-2.84 (m, 1H), 2.87-3.09 (m, 2 H), 3.44-3.56 (m, 2H), 7.01-7.22 (m, 2H), 7.36-4.55 (m, 1H), 8.43-8.71 (m, 1H), | M + 1: 438 |
| 16 | 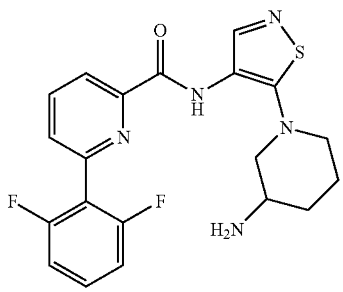 [SMILES: NC1CCCN(c2sncc2NC(=O)c2cccc(-c3c(F)cccc3F)n2)C1] | ¹H NMR (400 MHz, CDCl₃) δ 1.30-1.46 (m, 1H), 1.66-2.07 (m, 3 H), 2.65-2.84 (m, 1H), 2.87-3.09 (m, 2 H), 3.44-3.56 (m, 2H), 7.01-7.22 (m, 2H), 7.36-4.55 (m, 1H), 7.52 (m, 2H), 7.71 (m, 1H), 8.43-8.71 (m, 1H), | M + 1: 416 |
| 17 | 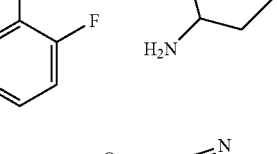 | ¹H NMR (400 MHz, MeOD₄) δ 1.61-1.83 (m, 2H), 1.89-2.11 (m, 2H), 2.91-3.13 (m, 2H), 3.45-3.63 (m, 2 H), 3.75 (s, 1H), 6.97-7.20 (m, 2H), 7.34-7.58 (m, 1H), 8.57 (s, 1H) | M − 1: 436 |
| 18 | 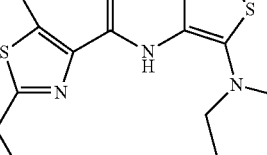 | ¹H NMR (400 MHz, CDCl₃) δ 1.71-1.93 (m, 2H), 1.94-2.17 (m, 2 H), 2.84-3.11 (m, 2H), 3.34-3.53 (m, 2 H), 3.83-4.00 (m, 1H), 7.02-7.18 (m, 2H), 7.36-7.57 (m, 1H), 8.29-8.48 (m, 1H), 8.92-9.09 (s, 1H), 9.10-9.20 (s, 1H) | M + 1: 423 |
| 19 | 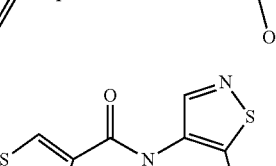 | ¹H NMR (400 MHz, CDCl₆) δ 3.18-3.20 (m, 4H), 3.91-3.93 (m, 4H), 7.82-7.84 (d, J = 5.2 Hz, 2H), 8.35 (s, 1H), 8.80-8.81 (d, J = 5.2 Hz, 2H), 8.97 (s, 1H), 9.00(s, 1H) | M − 1: 372 |
| 20 | 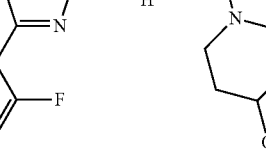 | ¹H NMR (400 MHz, CDCl₆) δ 3.18-3.20 (m, 4H), 3.91-3.93 (m, 4H), 7.47-7.48 (m, 1H), 8.22-8.24 (m, 1H), 8.30 (s, 1H), 8.74-8.75 (m, 1H), 8.98 (s, 1H), 9.00(s, 1H), 9.24 (s, 1H) | M − 1: 372 |

| | Structure | ¹HNMR | MS |
|---|---|---|---|
| 21 | 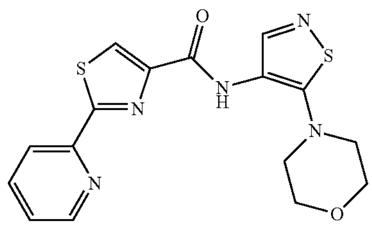 [SMILES: O=C(Nc1cnsc1N1CCOCC1)c1csc(-c2ccccn2)n1] | ¹H NMR (400 MHz, CDCl₆) δ 3.18-3.20 (m, 4H), 3.91-3.93 (m, 4H), 7.41-7.43 (m, 1H), 7.89-7.91 (m, 1H), 8.16-8.18 (m, 1H), 8.32 (s, 1H), 8.66-8.67 (m, 1H), 8.98 (s, 1H), 9.00 (s, 1H), | M − 1: 372 |
| 22 | 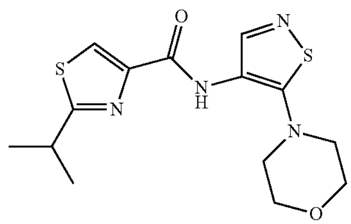 [SMILES: CC(C)c1nc(C(=O)Nc2cnsc2N2CCOCC2)cs1] | ¹H NMR (400 MHz, CDCl₃) δ 1.45-1.46 (d, J = 5.6 Hz, 6H), 3.14-3.16(m, 4H), 3.33 (m, 1H), 3.88-3.90 (m, 4H), 8.05 (s, 1H), 9.00 (s, 1H), 9.04(s, 1H), | M + 1: 339 |
| 23 | 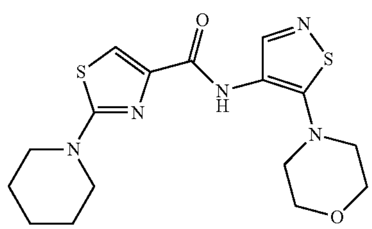 [SMILES: O=C(Nc1cnsc1N1CCOCC1)c1csc(N2CCCCC2)n1] | ¹H NMR (400 MHz, DMSO-d₆) δ 1.61 (m, 6H), 3.15-3.17 (m, 4H), 3.48 (m, 4H), 3.70-3.72 (m, 4H), 7.51 (s, 1H), 8.34 (s, 1H), 9.38 (s, 1H) | M + 1: 380 |
| 24 | 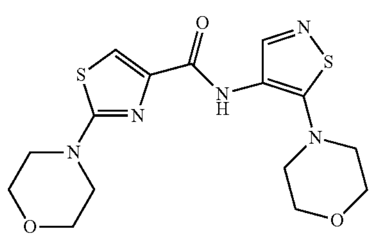 [SMILES: O=C(Nc1cnsc1N1CCOCC1)c1csc(N2CCOCC2)n1] | ¹H NMR (400 MHz, CDCl₆) δ 3.13-3.15 (m, 4H), 3.50-3.52 (m, 4H), 3.85-3.87 (m, 8H), 7.53 (s, 1H), 8.78 (s, 1H), 8.93 (s, 1H) | M + 1: 382 |
| 25 | 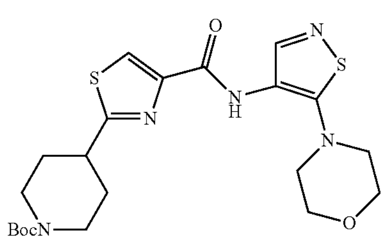 [SMILES: CC(C)(C)OC(=O)N1CCC(c2nc(C(=O)Nc3cnsc3N3CCOCC3)cs2)CC1] | ¹H NMR (400 MHz, CDCl₆) δ 1.48 (s, 9H), 1.78-1.80 (m, 2H), 2.17-2.18 (m, 2H), 2.96-2.98(m, 2H), 3.14-3.17 (m, 4H), 3.87-3.89 (m, 4H), 4.22-4.23 (m, 2H), 8.12 (s, 1H), 8.91 (s, 1H), 8.93 (s, 1H) | M + 1: 480 |
| 26 | 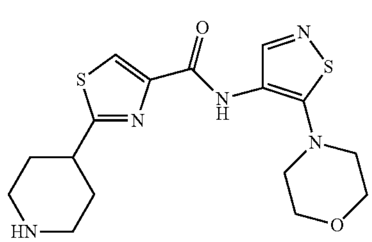 [SMILES: O=C(Nc1cnsc1N1CCOCC1)c1csc(C2CCNCC2)n1] | ¹H NMR (400 MHz, DMSO-d₆) δ 1.91-1.93 (m, 2H), 2.25-2.26 (m, 2H), 3.06-3.08(m, 2H), 3.13-3.15 (m, 4H), 3.37-3.40 (m, 3H), 3.69-3.71 (m, 4H), 8.28 (s, 1H), 8.36 (s, 1H), 8.61-8.68 (m, 1H), 8.92-8.93 (s, 1H), 9.68 (s, 1H) | M + 1: 380 |

-continued

| | Structure | ¹HNMR | MS |
|---|---|---|---|
| 27 | 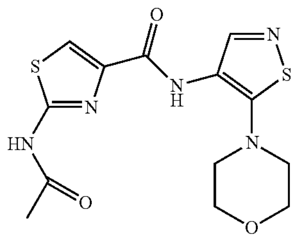 [SMILES: CC(=O)Nc1nc(C(=O)Nc2cnsc2N2CCOCC2)cs1] | ¹H NMR (400 MHz, CDCl₃) δ 2.34 (s, 3H), 3.13-3.15 (m, 4H), 3.86-3.88 (m, 4H), 7.88 (s, 1H), 8.60 (s, 1H), 8.85 (s, 1H), 8.90 (s, 1H) | M + 1: 354 |
| 28 | 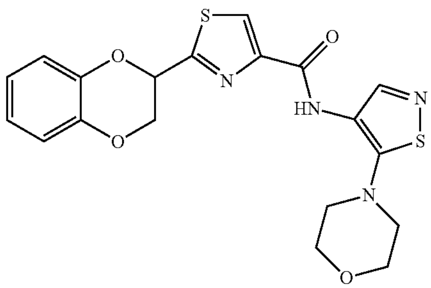 [SMILES: O=C(Nc1cnsc1N1CCOCC1)c1csc(C2COc3ccccc3O2)n1] | ¹H NMR (400 MHz, CDCl₃) 3.15-3.16 (m, 4H), 3.88-3.90 (m, 4H), 4.35-4.39 (m 1H), 4.64-4.67 (m, 1H), 5.55-5.57 (m, 1H), 6.94-6.95 (m, 3H), 7.04 (m, 1H), 8.28 (s, 1H), 8.85 (s, 1H), 8.92 (s, 1H) | M + 1: 431 |
| 29 | 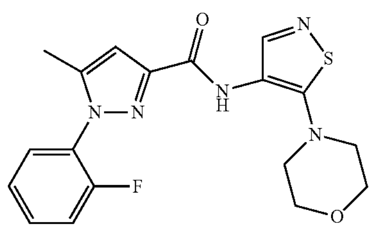 [SMILES: Cc1cc(C(=O)Nc2cnsc2N2CCOCC2)nn1-c1ccccc1F] | ¹H NMR (400 MHz, CDCl₃) δ 2.27 (s, 3H), 3.13-3.15 (m, 4H), 3.81-3.83 (m, 4H), 6.82 (s, 1H), 7.31-7.36 (m, 3H), 7.40-7.47 (m, 2H), 8.39 (s, 1H), 8.82 (s, 1H), | M + 1: 388 |
| 30 | 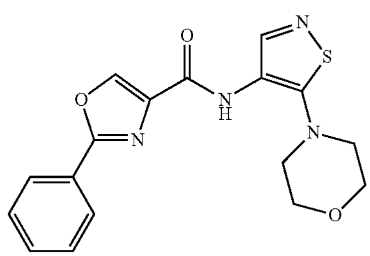 [SMILES: O=C(Nc1cnsc1N1CCOCC1)c1coc(-c2ccccc2)n1] | ¹H NMR (400 MHz, CDCl₃) δ 3.17-3.19 (m, 4H), 3.92-3.94 (m, 4H), 7.51-7.55 (m, 3H), 8.06-8.08 (m, 2H), 8.35 (s, 1H), 8.61 (s, 1H), 8.92 (s, 1H) | M: 356 |
| 31 | 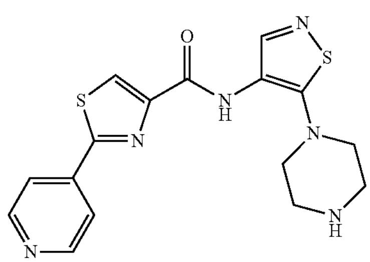 | ¹H NMR (400 MHz, DMSO-d₆) δ 2.97-2.98 (m, 4H), 3.27-3.30 (m, 4H), 8.06-8.07 (d, J = 5.2 Hz, 2H), 8.25 (s, 1H), 8.61 (s, 1H), 8.77-8.78 (d, J = 5.2 Hz, 2H), 10.02 (s, 1H), | M + 1: 373 |
| 32 | 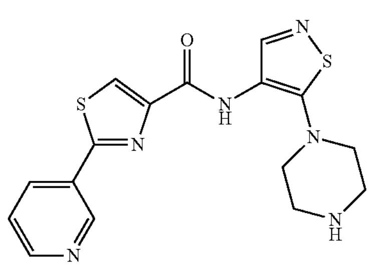 [SMILES: O=C(Nc1cnsc1N1CCNCC1)c1csc(-c2cccnc2)n1] | ¹H NMR (400 MHz, DMSO-d₆) δ 3.14-3.15 (m, 4H), 3.42-3.44 (m, 4H), 7.59-7.61 (m, 1H), 8.30 (s, 1H), 8.46-8.47 (m, 1H), 8.57 (s, 1H), 8.54-8.55 (m, 1H), 9.34-9.35 (s, 1H), 10.02 (s, 1H), | M + 1: 373 |

| | Structure | ¹HNMR | MS |
|---|---|---|---|
| 33 | 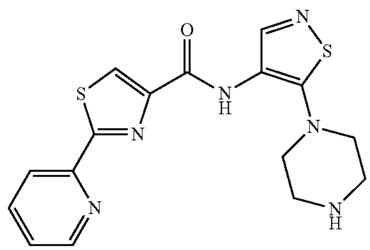 [SMILES: O=C(Nc1cnsc1N1CCNCC1)c1csc(-c2ccccn2)n1] | ¹H NMR (400 MHz, CDCl₆) δ 3.11-3.18 (m, 8H), 7.40-7.42 (m, 1H), 7.87-7.90(m, 1H), 8.17-8.19 (d, J = 5.2 Hz, 1H), 8.31 (s, 1H), 8.66-8.67 (d, J = 5.2 Hz, 1H), 9.00 (s, 1H), 9.02(s, 1H), | M + 1: 373 |
| 34 | 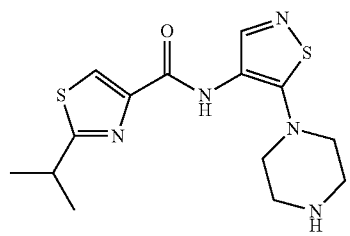 [SMILES: CC(C)c1nc(C(=O)Nc2cnsc2N2CCNCC2)cs1] | ¹H NMR (400 MHz, CDCl₆) δ 1.45-1.46(d, J = 6.8 Hz, 4H), 3.17-3.24(m, 8H), 3.32-3.35 (m, 1H), 4.16(s, 1H), 8.09(s, 1H), 8.98 (s, 1H), 9.03(s, 1H), | M + 1: 338 |
| 35 | 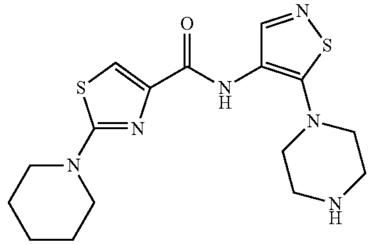 [SMILES: O=C(Nc1cnsc1N1CCNCC1)c1csc(N2CCCCC2)n1] | ¹H NMR (400 MHz, DMSO-d₆) δ 1.61(m, 6H), 2.79-2.81(m, 4H), 3.06-3.08 (m, 4H), 3.49-3.50 (m, 4H), 7.51 (s, 1H), 8.36 (s, 1H), 9.30 (s, 1H), | M + 1: 379 |
| 36 | 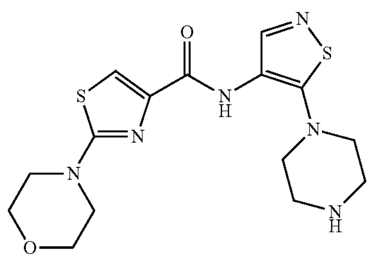 [SMILES: O=C(Nc1cnsc1N1CCNCC1)c1csc(N2CCOCC2)n1] | ¹H NMR (400 MHz, CDCl₆) δ 3.03-3.05 (m, 4H), 3.09-3.11(m, 4H), 3.50-3.52 (m, 4H), 3.85-3.87(m, 4H), 7.53(s, 1H), 8.78 (s, 1H), 8.95(s, 1H), | M + 1: 381 |
| 37 | 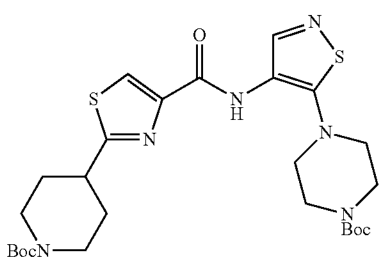 [SMILES: CC(C)(C)OC(=O)N1CCC(c2nc(C(=O)Nc3cnsc3N3CCN(C(=O)OC(C)(C)C)CC3)cs2)CC1] | ¹H NMR (400 MHz, CDCl₆) δ 1.40 (s, 18H), 1.78-1.80 (m, 2H), 2.12-2.13 (m, 2H), 2.94-2.93(m, 2H), 3.09-3.10 (m, 4H), 3.60-3.83 (m, 4H), 4.22-4.24 (m, 2H), 8.13 (s, 1H), 8.90 (s, 1H), 8.95 (s, 1H) | M: 579 |
| 38 | 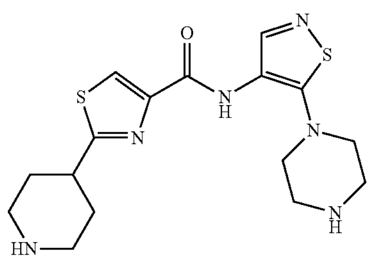 [SMILES: O=C(Nc1cnsc1N1CCNCC1)c1csc(C2CCNCC2)n1] | ¹H NMR (400 MHz, DMSO-d₆) δ 1.90-1.93(m, 2H), 2.26-2.29(m, 2H), 3.09-3.12 (m, 2H), 3.38-3.40 (m, 2H), 3.41-3.43 (m, 9H), 8.27 (s, 1H), 8.38 (s, 1H), 8.53 (m, 1H), 8.80(m, 1H), 8.98 (s, 1H), 9.77 (s, 1H), | M + 1: 379 |

-continued
| | Structure | ¹HNMR | MS |
|---|---|---|---|
| 39 | 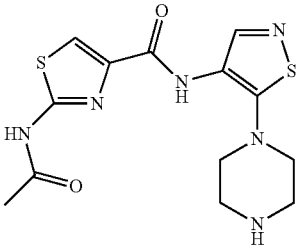 [SMILES: CC(=O)Nc1nc(C(=O)Nc2cnsc2N2CCNCC2)cs1] | ¹H NMR (400 MHz, DMSO-d₆) δ 2.18(s, 3H), 2.79-2.81(m, 4H), 3.07-3.09 (m, 4H), 7.91 (s, 1H), 8.32 (s, 1H), 9.18 (s, 1H), | M + 1: 353 |
| 40 | 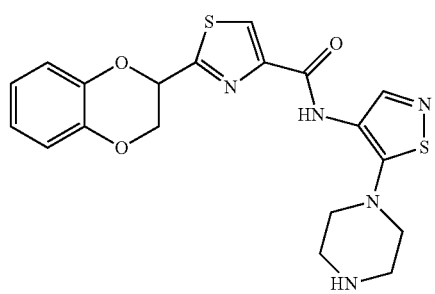 [SMILES: O=C(Nc1cnsc1N1CCNCC1)c1csc(C2COc3ccccc3O2)n1] | ¹H NMR (400 MHz, CDCl₃) δ 3.18-3.24 (m, 8H), 4.35-4.39 (dd, J = 11.6 Hz, J = 6.4 Hz, 1H), 4.64-4.67(dd, 11.6 Hz, J = 6.4 Hz, 1H), 5.56-5.58(dd, J = 11.6 Hz, J = 6.4 Hz, 1H), 6.93-6.94(m, 3H), 7.03-7.06 (m, 1H), 8.27 (s, 1H), 8.84(s, 1H), 8.94 (s, 1H), | M + 1: 430 |
| 41 | 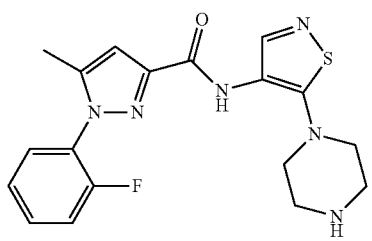 [SMILES: Cc1cc(C(=O)Nc2cnsc2N2CCNCC2)nn1-c1ccccc1F] | ¹H NMR (400 MHz, CDCl₃) δ 2.27(s, 3H), 3.00-3.12 (m, 8H), 6.82 (s, 1H), 7.31-7.33 (m, 2H), 7.47-7.50 (m, 2H), 8.39 (s, 1H), 8.83(s, 1H), | M + 1: 387 |
| 42 | 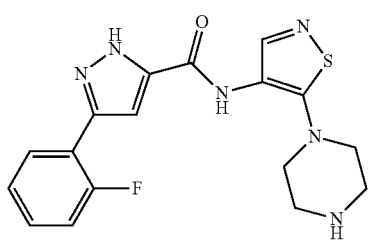 [SMILES: O=C(Nc1cnsc1N1CCNCC1)c1cc(-c2ccccc2F)n[nH]1] | ¹H NMR (400 MHz, DMSO-d₆) δ 2.78-2.79(m, 4H), 3.12-3.15 (m, 4H), 7.32-7.34 (m, 3H), 7.93 (m, 1H), 9.75 (s, 1H), 13.97 (s, 1H) | M + 1: 373 |
| 43 | 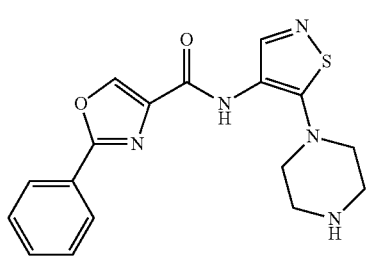 [SMILES: O=C(Nc1cnsc1N1CCNCC1)c1coc(-c2ccccc2)n1] | ¹H NMR (400 MHz, CDCl₃) δ 3.12-3.15 (m, 8H), 7.54 (m, 4H), 8.07-8.08(m, 2H), 8.36 (s, 1H), 8.63(s, 1H), 8.94 (s, 1H), | M + 1: 356 |
| 44 | 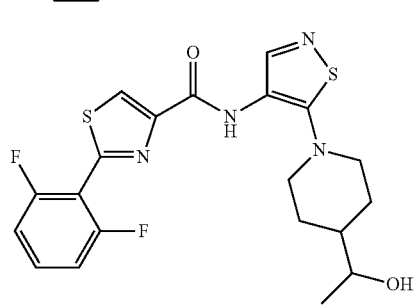 | ¹H NMR (400 MHz, CDCl₃) δ 1.23-1.25 (d, J = 6.4 Hz, 3H), 1.40 (m, 2H), 1.60 (m, 1H), 1.74 (m, 1H), 1.93 (m, 1 H), 2.79-2.80 (m, 2H), 3.51-3.53 (m, 2 H), 3.68 (m, 1H), 7.07-7.12 (m, 2H), 7.43-7.45 (m, 1H), 8.39 (m, 1H), 9.09 (m, 1H), 9.16 (m, 1H) | M: 450 |

-continued

| | Structure | ¹HNMR | MS |
|---|---|---|---|
| 45 | 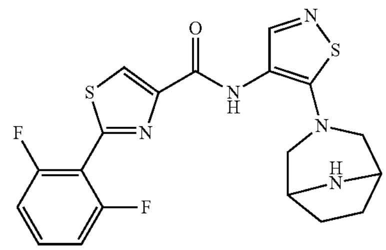 [SMILES: O=C(Nc1cnsc1N1CC2CCC(C1)N2)c1csc(-c2c(F)cccc2F)n1] | ¹H NMR (400 MHz, DMSO-d₆) δ 1.92-1.94 (m, 2H), 2.07-2.09 (m, 2H), 3.23-3.26 (m, 2H), 3.48-3.51(m, 2 H), 4.10 (m, 2H), 7.35-7.39 (m, 2H), 7.69 (m, 1H), 8.32 (s, 1H), 8.72 (s, 1H), 8.97 (m, 2H), 9.86 (s, 1H) | M + 1: 434 |
| 46 | 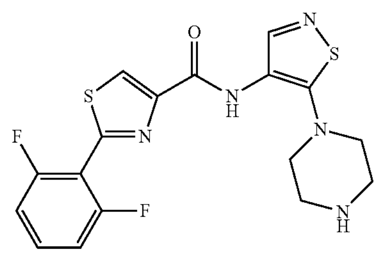 [SMILES: O=C(Nc1cnsc1N1CCNCC1)c1csc(-c2c(F)cccc2F)n1] | ¹H NMR (400 MHz, MeOD-d₄) δ 3.67 (m, 8H), 7.41 (m, 2H), 7.81-7.82 (m, 3H), 8.74 (s, 1H), 9.09(s, 1H), | M + 23: 450 |
| 47 | 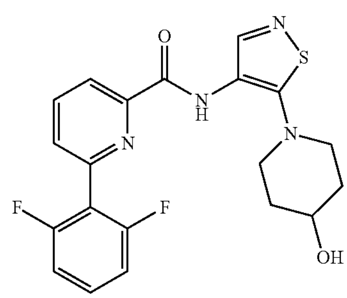 [SMILES: O=C(Nc1cnsc1N1CCC(O)CC1)c1cccc(-c2c(F)cccc2F)n1] | ¹H NMR (400 MHz, CDCl₃) δ 1.73-1.74 (m, 2H), 1.97-1.98 (m, 2 H), 2.95 (m, 2H), 3.38-3.41 (m, 2H), 3.89 (m, 1H), 7.06-7.09 (m, 2H), 7.28 (m, 1H), 7.74 (d, 4 Hz, 1H), 8.03 (m, 1H), 8.29-8.31 (d, J = 4 Hz, 1H), 9.10 (s, 1H), 9.82 (s, 1H) | M + 1: 417 |
| 48 | 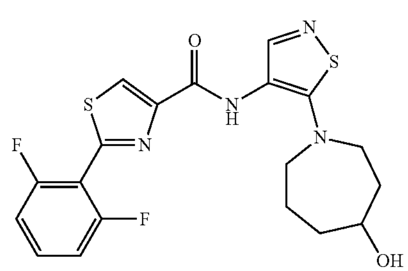 [SMILES: O=C(Nc1cnsc1N1CCCC(O)CC1)c1csc(-c2c(F)cccc2F)n1] | ¹H NMR (400 MHz, CDCl₃) δ 1.62-1.64 (m, 4H), 1.84-1.85 (m, 2H), 3.37-3.42(m, 3 H), 3.54-3.56(m, 1H), 3.93-3.94 (m, 1H), 7.08-7.12 (m, 2H), 7.42-7.45(m, 1H), 8.39 (s, 2H), 8.83(s, 1H), | M + 1: 437 |
| 49 | 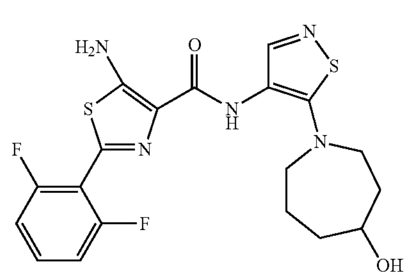 [SMILES: Nc1sc(-c2c(F)cccc2F)nc1C(=O)Nc1cnsc1N1CCCC(O)CC1] | ¹H NMR (400 MHz, DMSO) δ 1.62-1.64 (m, 6H), 1.84-1.85 (m, 2H), 3.48-3.51(m, 1 H), 3.69-3.70(m, 1H), 4.56-4.57 (m, 1H), 7.26-7.30 (m, 2H), 7.52-7.57 (m, 4H), 7.95-7.96 (m, 1H), 8.93-8.96 (m, 1H), | M + 1: 452 |

| | Structure | ¹HNMR | MS |
|---|---|---|---|
| 50 | 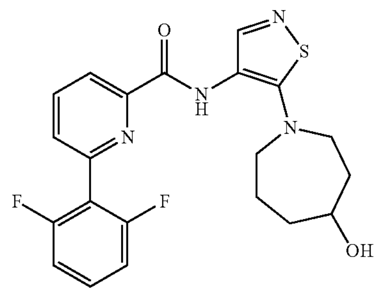 [SMILES: O=C(Nc1cnsc1N1CCCC(O)CC1)c1cccc(-c2c(F)cccc2F)n1] | ¹H NMR (400 MHz, CDCl₃) δ 1.62-1.64(m, 4H), 1.84-1.85(m, 2H), 3.37-3.42(m, 3H), 3.54-3.56 (m, 1H), 3.93-3.94 (m, 1H), 7.04-7.08 (m, 2H), 7.40-7.44(m, 1H), 7.70-7.72(d, J = 4.0 Hz, 1H), 8.00-8.02 (m, 1H), 8.29-8.30 (d, J = 4 Hz, 1H), 8.45 (s, 1H), 9.47(s, 1H) | M + 1: 431 |
| 51 | 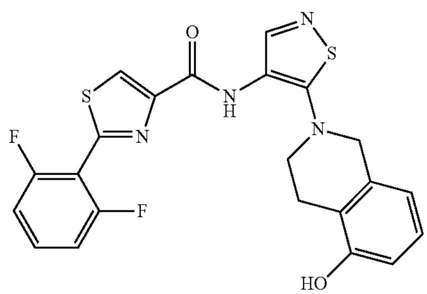 [SMILES: O=C(Nc1cnsc1N1CCc2c(O)cccc2C1)c1csc(-c2c(F)cccc2F)n1] | ¹H NMR (400 MHz, DMSO) δ 2.69 (m, 2H), 3.55-3.56 (m, 2 H), 4.38 (s, 2H), 6.55 (m, 1H), 6.67 (m, 1H), 6.96 (m, 1H), 7.36 (m, 2H), 7.67-7.69 (m, 1H), 8.26 (s, 1H), 8.71 (s, 1H), 9.47 (s, 1H), 9.85 (s, 1H) | M − 1: 469 |
| 52 | 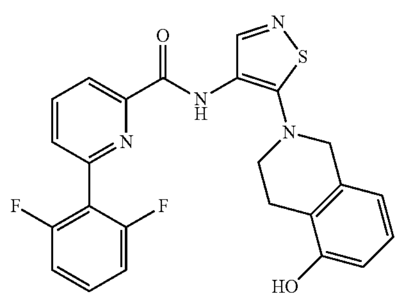 [SMILES: O=C(Nc1cnsc1N1CCc2c(O)cccc2C1)c1cccc(-c2c(F)cccc2F)n1] | ¹H NMR (400 MHz, DMSO) δ 2.69 (m, 2H), 3.51 (m, 2 H), 4.35 (s, 2H), 6.49 (m, 1H), 6.68-6.70 (m, 1H), 6.94 (m, 1H), 7.26 (m, 2H), 7.58-4.59 (m, 1H), 7.90 (m, 1H), 8.18 (m, 2H), 8.41 (s, 1H), 9.56 (s, 1H), 10.07 (s, 1H) | M − 1: 463 |
| 53 | 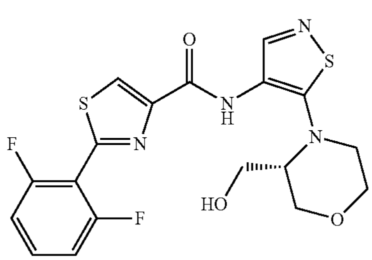 [SMILES: O=C(Nc1cnsc1N1CCOC[C@@H]1CO)c1csc(-c2c(F)cccc2F)n1] | ¹H NMR (400 MHz, CDCl₃) δ 2.61-2.63 (m, 1H), 3.12-3.14(m, 1H), 3.45-3.47(m, 2H), 3.86-3.92(m, 5H), 7.13 (m, 1H), 7.47(m, 2H), 8.41(s, 1H), 8.85 (s, 1H), 9.44 (s, 1H), | M − 1: 437 |
| 54 | 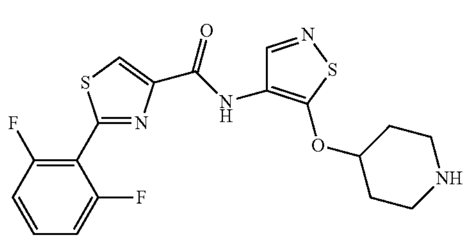 [SMILES: O=C(Nc1cnsc1OC1CCNCC1)c1csc(-c2c(F)cccc2F)n1] | ¹H NMR (400 MHz, CD₃OD) δ: 1.83-1.91 (m, 2H), 2.14-2.20 (m, 2H), 2.74-2.80 (m, 2H), 3.12-3.17 (m, 2H), 4.46-4.51 (m, 1H), 7.27 (t, J = 8.7 Hz, 2H), 7.59-7.67 (m, 1H), 8.60 (s, 1H), 8.85 (s, 1H) | M + 1: 431 |

-continued

| | Structure | ¹HNMR | MS |
|---|---|---|---|
| 55 | 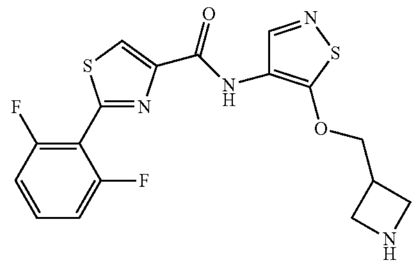 [SMILES: O=C(Nc1cnsc1OCC1CNC1)c1csc(-c2c(F)cccc2F)n1] | ¹H NMR (400 MHz, DMSO-d6) δ 2.99-3.13 (m, 1H), 3.35 (d, J = 7.78 Hz, 2H), 3.59 (t, J = 7.53 Hz, 2H), 4.39 (d, J = 6.27 Hz, 2H), 7.38 (t, J = 9.16 Hz, 3H), 7.62-7.75 (m, 1H), 8.60 (s, 1H), 8.72 (s, 1H) | M + 1: 409 |
| 56 | 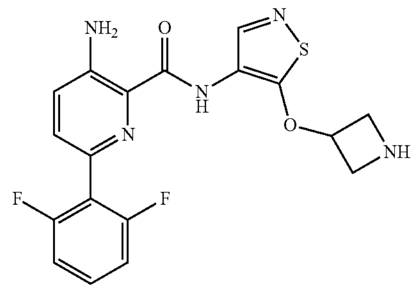 [SMILES: Nc1ccc(-c2c(F)cccc2F)nc1C(=O)Nc1cnsc1OC1CNC1] | ¹H NMR (400 MHz, CD₃OD) δ: 4.29 (d, J = 10.79 Hz, 2H), 4.49-4.59 (m, 2H), 5.22 (bs, 1H), 7.10 (t, J = 7.40 Hz, 2H), 7.32 (d, J = 8.78 Hz, 1H), 7.40-7.53 (m, 2H), 8.80 (s, 1H) | M + 1: 404 |
| 57 | 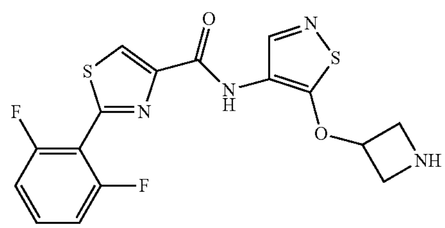 [SMILES: O=C(Nc1cnsc1OC1CNC1)c1csc(-c2c(F)cccc2F)n1] | ¹H NMR (400 MHz, DMSO-d6) δ: 4.16 (d, J = 10.79 Hz, 2H), 4.33-4.47 (m, 2H), 5.18 (bs, 1H), 7.38 (t, J = 9.41 Hz, 2H), 7.63-7.79 (m, 1H), 8.56 (s, 1H), 8.74 (s, 1H), 9.87 (s, 1H) | M + 1: 395 |
| 58 | 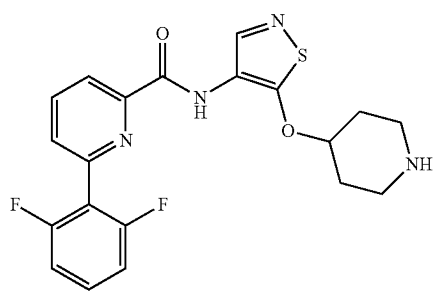 [SMILES: O=C(Nc1cnsc1OC1CCNCC1)c1cccc(-c2c(F)cccc2F)n1] | ¹H NMR (400 MHz, DMSO-d6) δ: 1.95-2.03 (m, 2H), 2.14-2.20 (m, 2H), 3.11-3.16 (m, 2H), 3.23-3.28 (m, 2H), 4.58-4.63(m, 1H), 7.31-7.35 (m, 2H), 7.59-7.66 (m, 1H), 7.91-7.93 (m, 1H), 8.18-8.26 (m, 1H), 8.59 (bs, 2H), 10.09 (s, 1H), | M + 1: 417 |
| 59 | 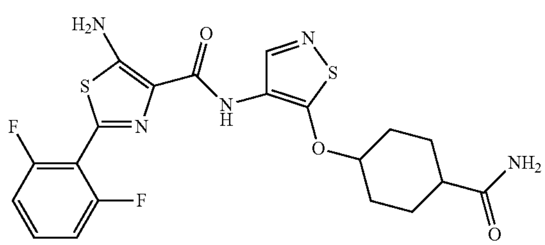 [SMILES: NC(=O)C1CCC(Oc2sncc2NC(=O)c2nc(-c3c(F)cccc3F)sc2N)CC1] | ¹H NMR (400 MHz, CD₃OD) δ: 1.40-1.66 (m, 4H), 1.81-1.89 (m, 2H), 2.10-2.23 (m, 3H), 3.46 (bs, 1H), 7.11-7.25 (m, 2H), 7.54-7.71 (m, 1H), 9.10 (s, 1H) | M: 479 |
| 60 | 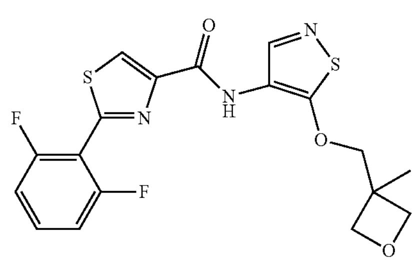 [SMILES: CC1(COc2sncc2NC(=O)c2csc(-c3c(F)cccc3F)n2)COC1] | ¹H NMR (400 MHz, DMSO-d6) δ: 1.37 (s, 3H), 4.29 (d, J = 6.0 Hz, 2H), 4.34 (s, 2H), 4.52 (d, J = 6.0 Hz, 2H), 7.37 (t, J = 8.8 Hz, 2H), 7.63-7.72 (m, 1H), 8.62 (s, 1H), 8.72 (s, 1H), 9.70 (s, 1H) | M: 423 |

| | Structure | ¹HNMR | MS |
|---|---|---|---|
| 61 | 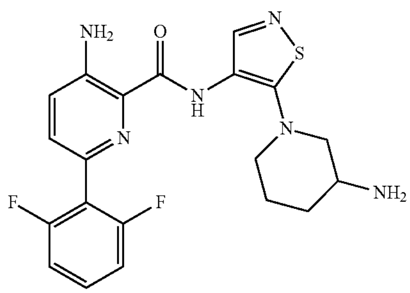 [SMILES: Nc1ccc(-c2c(F)cccc2F)nc1C(=O)Nc1cnsc1N1CCCC(N)C1] | ¹H NMR (400 MHz, CDCl₃) δ: 1.19-1.42 (m, 3H), 1.73-1.97 (m, 2H), 2.50-2.72 (m, 1H), 2.83-2.93 (m, 2H), 2.93-2.99 (m, 1H), 2.98-3.09 (m, 1H), 3.32-3.47 (m, 1H), 6.04-6.30(m, 2H), 7.02 (t, J = 7.66 Hz, 3H), 7.11-7.17 (m, 1H), 7.29-7.39 (m, 2H), 7.40-7.49 (m, 1H), 8.82-9.00 (m, 1H), 9.71-9.88 (m, 1H), | M + 1: 431 |
| 62 | 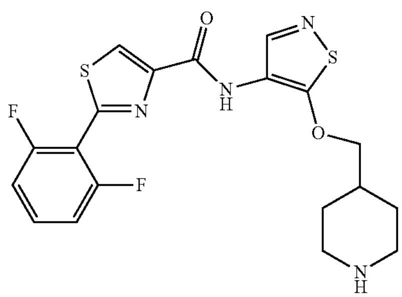 [SMILES: O=C(Nc1cnsc1OCC1CCNCC1)c1csc(-c2c(F)cccc2F)n1] | ¹H NMR (400 MHz, CDCl₃) δ: 0.86 (d, J = 14.31 Hz, 1H), 1.32-1.46 (m, 2H), 1.91 (d, J = 12.05 Hz, 2H), 2.73 (t, J = 12.17 Hz, 2H), 3.21 (d, J = 12.05 Hz, 2H), 4.05 (d, J = 6.02 Hz, 2H), 7.10 (t, J = 9.16 Hz, 2H), 7.39-7.50 (m, 1H), 8.37 (s, 1H), 9.11 (s, 1H), 9.21 (bs, 1H) | M + 1: 437 |
| 63 | 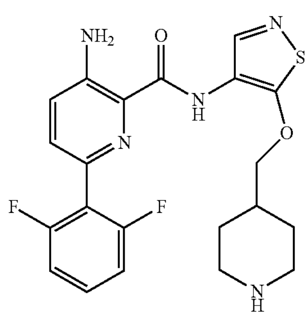 [SMILES: Nc1ccc(-c2c(F)cccc2F)nc1C(=O)Nc1cnsc1OCC1CCNCC1] | ¹H NMR (400 MHz, DMSO-d6) δ: 1.34 (bs, 2H), 1.78 (bs, 2H), 2.69 (bs, 3H), 3.12 (bs, 3H), 4.11 (bs, 1H), 7.07-7.40 (m, 5H), 7.53 (bs, 2H), 8.33 (bs, 1H), 8.86 (bs, 1H), 9.83 (bs, 1H) | M + 1: 446 |
| 64 | 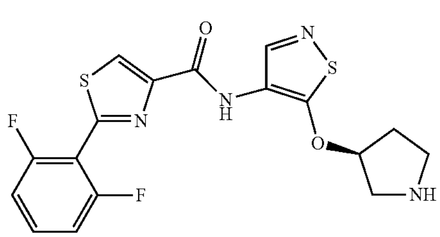 [SMILES: O=C(Nc1cnsc1O[C@H]1CCNC1)c1csc(-c2c(F)cccc2F)n1] | ¹H NMR (400 MHz, CDCl₃) δ: 1.76 (bs, 1H), 2.21 (bs, 1H), 2.37 (bs, 1H), 3.50-3.78 (m, 3H), 4.85 (bs, 1H), 7.11 (t, J = 9.41 Hz, 2H), 7.37-7.51 (m, 1H), 8.37 (s, 1H), 9.03-9.26 (m, 2H) | M + 1: 409 |
| 65 | 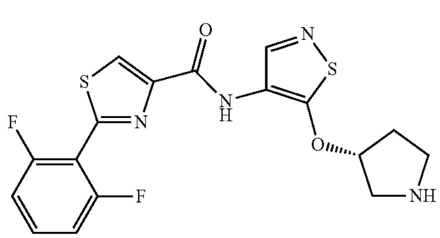 [SMILES: O=C(Nc1cnsc1O[C@@H]1CCNC1)c1csc(-c2c(F)cccc2F)n1] | ¹H NMR (400 MHz, CDCl₃) δ: 1.76 (bs, 1H), 2.21 (bs, 1H), 2.37 (bs, 1H), 3.50-3.78 (m, 3H), 4.85 (bs, 1H), 7.11 (t, J = 9.41 Hz, 2H), 7.37-7.51 (m, 1H), 8.37 (s, 1H), 9.03-9.26 (m, 2H) | M + 1: 409 |

-continued

| | Structure | ¹HNMR | MS |
|---|---|---|---|
| 66 | 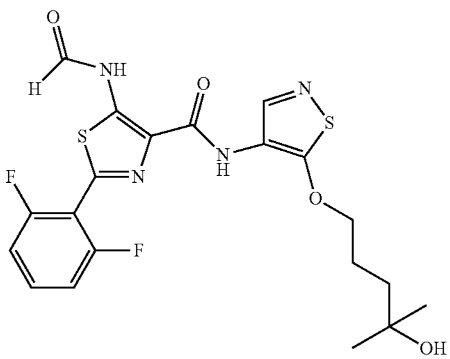 [SMILES: CC(C)(O)CCCOc1sncc1NC(=O)c1nc(-c2c(F)cccc2F)sc1NC=O] | ¹H NMR (400 MHz, CD₃OD) δ: 1.12 (s, 6H), 1.39-1.50 (m, 2H), 1.70-1.81 (m, 2H), 4.21 (t, J = 6.76 Hz, 2H), 7.11-7.25 (m, 2H), 7.54-7.71 (m, 1H), 9.10 (s, 1H), 11.90 (s, 1H) | M: 482 |
| 67 | 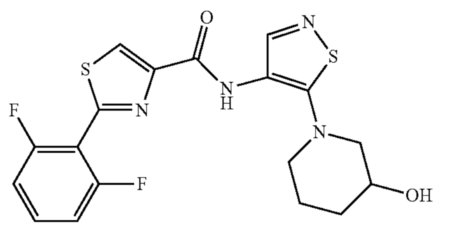 [SMILES: O=C(Nc1cnsc1N1CCCC(O)C1)c1csc(-c2c(F)cccc2F)n1] | ¹H NMR (400 MHz, CDCl₃) δ: 1.66-1.80 (m, 2H), 1.80-1.94 (m, 1H), 1.94-2.15 (m, 1H), 2.28-2.51 (m, 1H), 3.01-3.36 (m, 3H), 3.86-4.14 (m, 1H), 6.92-7.19 (m, 2H), 7.37-7.58 (m, 1H), 8.28-8.54 (m, 1H), 8.94 (s, 1H), 9.08-9.31 (m, 1H) | M: 422 |
| 68 | 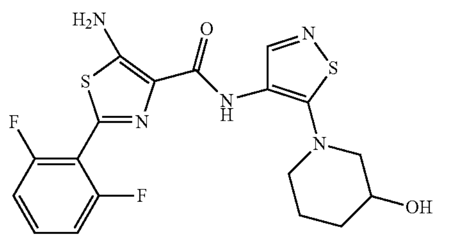 [SMILES: Nc1sc(-c2c(F)cccc2F)nc1C(=O)Nc1cnsc1N1CCCC(O)C1] | ¹H NMR (400 MHz, CDCl₃) δ: 1.66-1.77 (m, 2H), 1.78-1.91 (m, 1H), 1.95-2.12 (m, 1H), 2.40-2.63 (m, 1H), 2.98-3.40 (m, 3H), 3.83-4.10 (m, 1H), 5.98-6.38 (m, 2H), 6.89-7.14 (m, 2H), 7.32-7.49 (m, 1H), 8.53-8.74 (m, 1H), 8.75-8.89 (m, 1H) | M + 1: 438 |
| 69 | 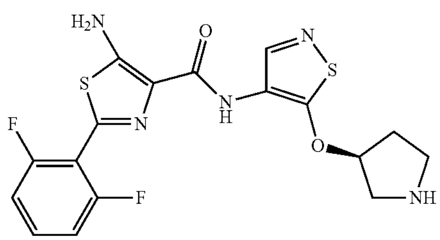 [SMILES: Nc1sc(-c2c(F)cccc2F)nc1C(=O)Nc1cnsc1O[C@H]1CCNC1] | ¹H NMR (400 MHz, CD₃OD) δ: 3.06 (t, J = 4.39 Hz, 2H), 3.14 (t, J = 7.78 Hz, 2H), 4.32 (t, J = 7.78 Hz, 2H), 4.50 (t, J = 4.39 Hz, 1H), 7.12-7.34 (m, 2H), 7.48-7.72 (m, 1H), 9.10 (s, 1H) | M + 1: 424 |
| 70 | 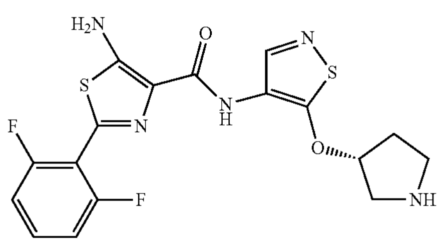 [SMILES: Nc1sc(-c2c(F)cccc2F)nc1C(=O)Nc1cnsc1O[C@@H]1CCNC1] | ¹H NMR (400 MHz, CD₃OD) δ: 3.06 (t, J = 4.39 Hz, 2H), 3.14 (t, J = 7.78 Hz, 2H), 4.32 (t, J = 7.78 Hz, 2H), 4.50 (t, J = 4.39 Hz, 1H), 7.12-7.34 (m, 2H), 7.48-7.72 (m, 1H), 9.10 (s, 1H) | M + 1: 424 |
| 71 | 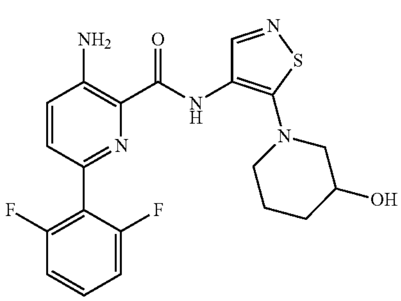 [SMILES: Nc1ccc(-c2c(F)cccc2F)nc1C(=O)Nc1cnsc1N1CCCC(O)C1] | ¹H NMR (400 MHz, CDCl₃) δ: 1.13-1.43 (m, 1H), 2.14-2.37 (m, 1H), 2.96-3.15 (m, 3H), 3.22-3.36 (m, 1H), 3.74-4.02 (m, 1H), 5.90-6.29 (m, 2H), 6.89-7.20 (m, 4H), 7.30-7.41 (m, 2H), 7.41-7.59 (m, 1H), 8.72-8.99 (m, 1H), 9.64-9.90 (m, 1H) | M + 1: 432 |

-continued

| | Structure | ¹HNMR | MS |
|---|---|---|---|
| 72 | 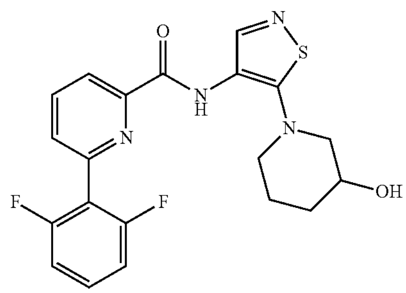 [SMILES: O=C(Nc1cnsc1N1CCCC(O)C1)c1cccc(-c2c(F)cccc2F)n1] | ¹H NMR (400 MHz, CD₃OD) δ: 1.37-1.54 (m, 1H), 1.53-1.75 (m, 1H), 1.76-2.05 (m, 2H), 2.71-3.10 (m, 3H), 3.41-3.52 (m, 1H), 3.66-3.89 (m, 1H), 6.89-7.26 (m, 2H), 7.44-7.63 (m, 1H), 7.75-7.91 (m, 1H), 8.07-8.32 (m, 2H), 8.49-8.81 (m, 1H) | M: 416 |
| 73 | 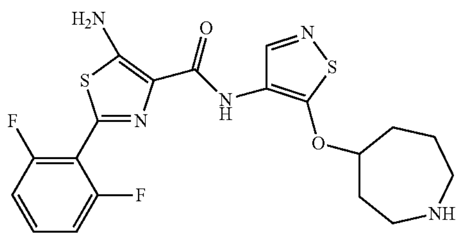 [SMILES: Nc1sc(-c2c(F)cccc2F)nc1C(=O)Nc1cnsc1OC1CCCNCC1] | ¹H NMR (400 MHz, CD₃OD) δ: 1.88 (d, J = 7.78 Hz, 1H), 2.04-2.49 (m, 5H), 3.25 (d, J = 5.52 Hz, 2H), 3.38-3.52 (m, 1H), 4.51-4.74 (m, 2H), 7.14 (t, J = 8.78 Hz, 2H), 7.47 (t, J = 7.28 Hz, 1H), 8.52 (s, 1H), 8.74 (s, 1H) | M + 1: 452 |
| 74 | 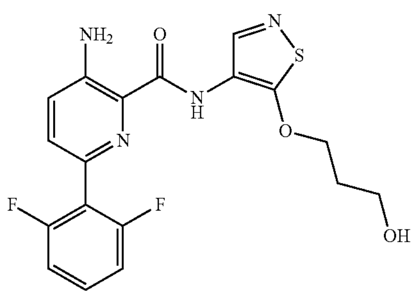 [SMILES: Nc1ccc(-c2c(F)cccc2F)nc1C(=O)Nc1cnsc1OCCCO] | ¹H NMR (400 MHz, DMSO-d6) δ: 1.90 (s, 2H), 3.55 (s, 2H), 3.27 (s, 2H), 4.63 (s, 1H), 7.14 (s, 2H), 7.22 (t, J = 8.32 Hz, 2H), 7.38 (d, J = 5.48 Hz, 1H), 7.50-7.60 (m, 2H), 8.82 (s, 1H), 9.83 (s, 1H) | M: 406 |
| 75 | 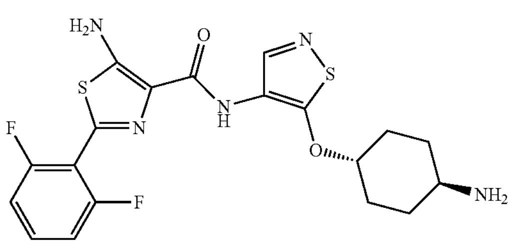 [SMILES: Nc1sc(-c2c(F)cccc2F)nc1C(=O)Nc1cnsc1O[C@H]1CC[C@H](N)CC1] | ¹H NMR (400 MHz, CD₃OD) δ: 1.10-1.51 (m, 2H), 1.64-1.69 (m, 2H), 1.98-2.02 (m, 2H), 2.20-2.23 (m, 2H), 2.84-2.90 (m, 1H), 4.35-4.41 (m, 1H), 7.10-7.28 (m, 2H), 7.47-7.69 (m, 1H), 9.10 (s, 1H) | M + 1: 452 |
| 76 | 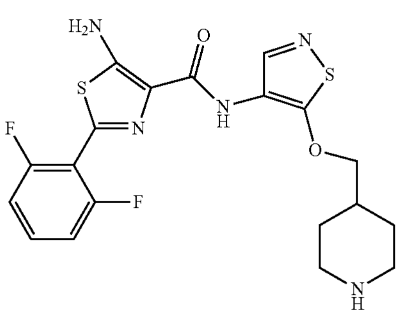 [SMILES: Nc1sc(-c2c(F)cccc2F)nc1C(=O)Nc1cnsc1OCC1CCNCC1] | ¹H NMR (400 MHz, CD₃OD) δ: 1.26-1.29 (m, 2H), 1.91-1.94 (m, 2H), 2.04-2.12 (m, 1H), 2.66-2.69 (m, 2H), 3.10-3.13 (m, 2H), 3.90-3.98 (m, 2H), 7.05-7.27 (m, 2H), 7.39-7.69 (m, 1H), 9.11 (s, 1H) | M + 1: 452 |

| | Structure | ¹HNMR | MS |
|---|---|---|---|
| 77 | 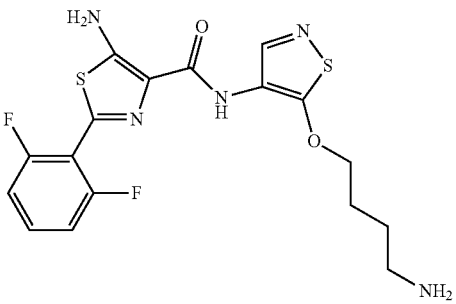 [SMILES: NCCCCOc1sncc1NC(=O)c1nc(-c2c(F)cccc2F)sc1N] | ¹H NMR (400 MHz, CD₃OD) δ: 1.51-1.59 (m, 2H), 1.77-1.79 (m, 2H), 2.81-2.83 (m, 2H), 4.21 (t, J = 5.96 Hz, 2H), 7.10-7.31 (m, 2H), 7.51-7.69 (m, 1H), 9.12 (s, 1H) | M + 1: 426 |
| 78 | 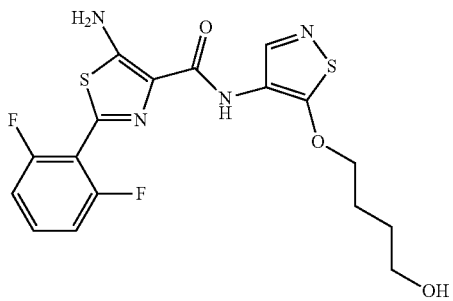 [SMILES: Nc1sc(-c2c(F)cccc2F)nc1C(=O)Nc1cnsc1OCCCCO] | ¹H NMR (400 MHz, CD₃OD) δ: 1.45-1.52 (m, 2H), 1.74-1.78 (m, 2H), 3.36-3.45 (m, 2H), 4.21 (t, J = 5.96 Hz, 2H), 7.08-7.34 (m, 2H), 7.48-7.74 (m, 1H), 9.10 (s, 1H) | M: 426 |
| 79 | 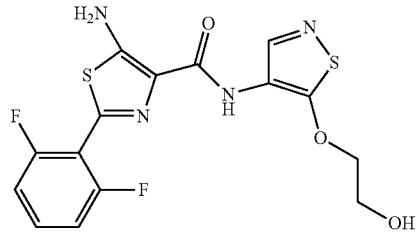 [SMILES: Nc1sc(-c2c(F)cccc2F)nc1C(=O)Nc1cnsc1OCCO] | ¹H NMR (400 MHz, CD₃OD) δ: 3.73-3.81 (m, 2H), 4.20 (t, J = 4.60 Hz, 2H), 7.09-7.32 (m, 2H), 7.45-7.69 (m, 1H), 9.10 (s, 1H) | M: 398 |
| 80 | 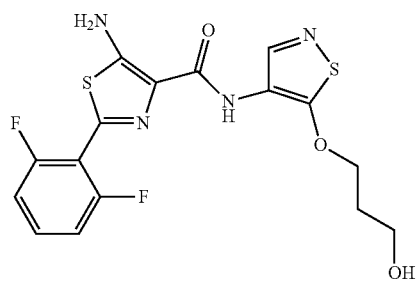 [SMILES: Nc1sc(-c2c(F)cccc2F)nc1C(=O)Nc1cnsc1OCCCO] | ¹H NMR (400 MHz, CD₃OD) δ: 1.89-1.94 (m, 2H), 3.57-3.63 (m, 2H), 4.21 (t, J = 5.96 Hz, 2H), 7.11-7.37 (m, 2H), 7.50-7.68 (m, 1H), 9.11 (s, 1H) | M: 412 |
| 81 | 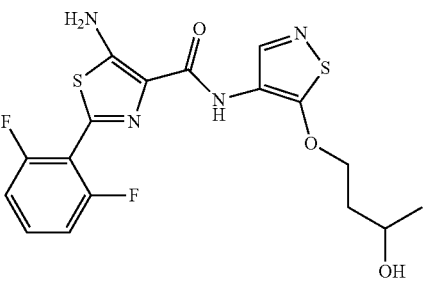 [SMILES: CC(O)CCOc1sncc1NC(=O)c1nc(-c2c(F)cccc2F)sc1N] | ¹H NMR (400 MHz, CD₃OD) δ: 1.01 (s, 3H), 1.59-1.78 (m, 2H), 3.40-3.55 (m, 1H), 4.10-4.25 (m, 2H), 7.18-7.34 (m, 2H), 7.53-7.74 (m, 1H), 9.11 (s, 1H) | M: 426 |

| | Structure | ¹HNMR | MS |
|---|---|---|---|
| 82 | 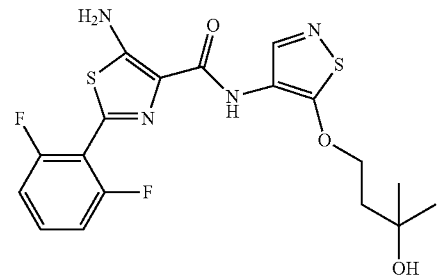 [SMILES: CC(C)(O)CCOc1sncc1NC(=O)c1nc(-c2c(F)cccc2F)sc1N] | ¹H NMR (400 MHz, CD₃OD) δ 1.17 (s, 6H), 1.91-2.02 (m, 2H), 4.33 (t, J = 6.84 Hz, 2H), 7.10-7.28 (m, 2H), 7.55-7.72 (m, 1H), 9.10 (s, 1H) | M: 440 |
| 83 | 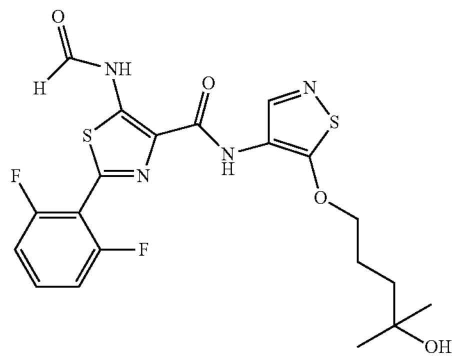 [SMILES: CC(C)(O)CCCOc1sncc1NC(=O)c1nc(-c2c(F)cccc2F)sc1NC=O] | ¹H NMR (400 MHz, CD₃OD) δ: 1.12 (s, 6H), 1.39-1.50 (m, 2H), 1.70-1.81 (m, 2H), 4.21 (t, J = 6.76 Hz, 2H), 7.11-7.25 (m, 2H), 7.54-7.71 (m, 1H), 9.10 (s, 1H), 11.90 (s, 1H) | M: 482 |
| 84 | 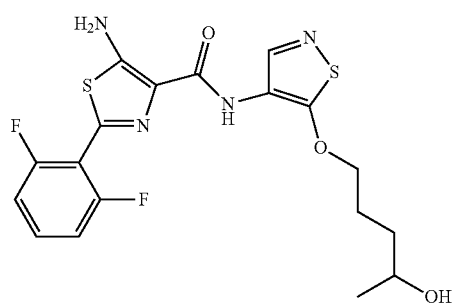 | ¹H NMR (400 MHz, CD₃OD) δ: 1.10 (s, 3H), 1.38-1.45 (m, 2H), 1.78-1.84 (m, 2H), 3.38-3.46 (m, 1H), 4.33 (t, J = 6.84 Hz, 2H), 7.15-7.28 (m, 2H), 7.51-7.69 (m, 1H), 9.11 (s, 1H) | M: 440 |
| 85 | 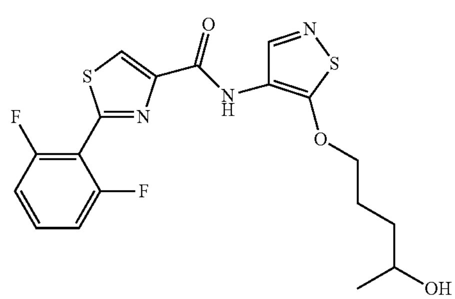 [SMILES: CC(O)CCCOc1sncc1NC(=O)c1csc(-c2c(F)cccc2F)n1] | ¹H NMR (400 MHz, CD₃OD) δ: 1.16 (s, 3H), 1.40-1.45 (m, 2H), 1.80-1.88 (m, 2H), 3.40-3.46 (m, 1H), 4.30 (t, J = 6.80 Hz, 2H), 7.10 (t, J = 9.16 Hz, 2H), 7.40-7.50 (m, 1H), 9.10 (s, 1H), 9.20 (s, 1H) | M: 425 |
| 86 | 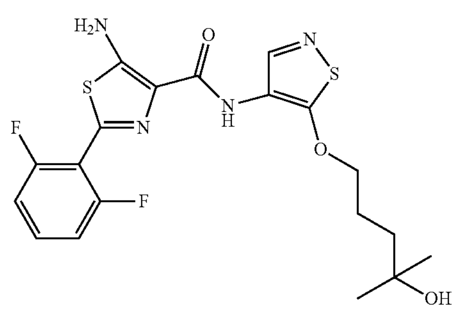 [SMILES: CC(C)(O)CCCOc1sncc1NC(=O)c1nc(-c2c(F)cccc2F)sc1N] | ¹H NMR (400 MHz, CD₃OD) δ: 1.11 (s, 6H), 1.42-1.48 (m, 2H), 1.72-1.80 (m, 2H), 4.21 (t, J = 6.84 Hz, 2H), 7.09-7.25 (m, 2H), 7.49-7.70 (m, 1H), 9.10 (s, 1H) | M: 454 |

-continued
| | Structure | ¹HNMR | MS |
|---|---|---|---|
| 87 | 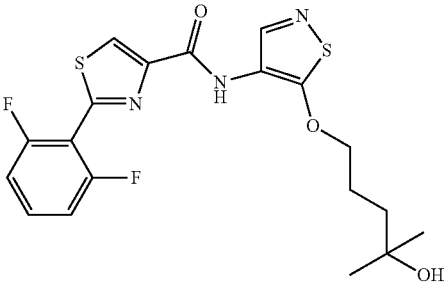 [SMILES: CC(C)(O)CCCOc1sncc1NC(=O)c1csc(-c2c(F)cccc2F)n1] | ¹H NMR (400 MHz, CD₃OD) δ: 1.14 (s, 6H), 1.39-1.48 (m, 2H), 1.69-1.79 (m, 2H), 4.20 (t, J = 6.84 Hz, 2H), 7.12 (t, J = 9.16 Hz, 2H), 7.42-7.52 (m, 1H), 9.10 (s, 1H), 9.20 (s, 1H) | M: 439 |
| 88 | 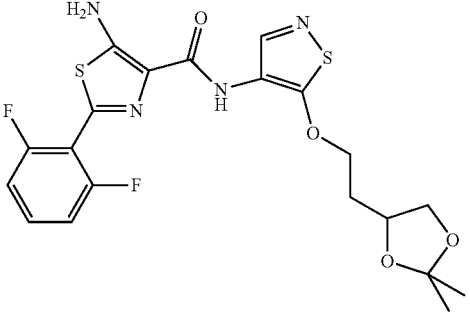 [SMILES: CC1(C)OCC(CCOc2sncc2NC(=O)c2nc(-c3c(F)cccc3F)sc2N)O1] | ¹H NMR (400 MHz, CD₃OD) δ: 1.21 (s, 6H), 2.01-2.20 (m, 2H), 4.10-4.17 (m, 2H), 4.20-4.30 (m, 1H), 4.31-4.40 (m, 2H), 7.18-7.31 (m, 2H), 7.61-7.72 (m, 1H), 9.12 (s, 1H) | M: 482 |
| 89 | 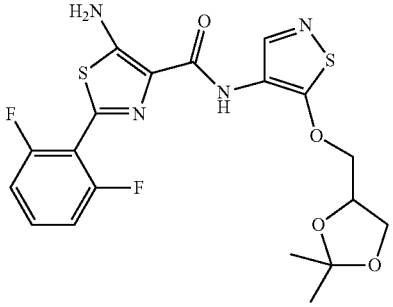 [SMILES: CC1(C)OCC(COc2sncc2NC(=O)c2nc(-c3c(F)cccc3F)sc2N)O1] | ¹H NMR (400 MHz, CD₃OD) δ: 1.38 (s, 3H), 1.40 (s, 3H), 4.04 (t, J = 4.68 Hz, 1H), 4.11 (t, J = 4.20 Hz, 1H), 4.20-4.24 (m, 2H), 4.50-4.65 (m, 1H), 7.11-7.27 (m, 2H), 7.51-7.75 (m, 1H), 9.10 (s, 1H) | M: 468 |
| 90 | 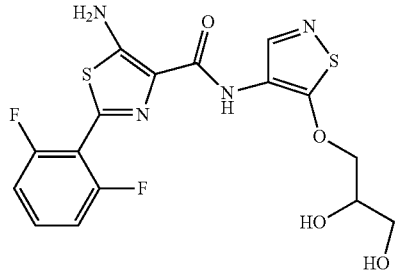 [SMILES: Nc1sc(-c2c(F)cccc2F)nc1C(=O)Nc1cnsc1OCC(O)CO] | ¹H NMR (400 MHz, CD₃OD) δ: 3.52 (bs, 2H), 3.86 (bs, 1H), 4.15-4.25 (m, 2H), 7.10-7.25 (m, 2H), 7.47-7.73 (m, 1H), 9.10 (s, 1H) | M: 428 |
| 91 | 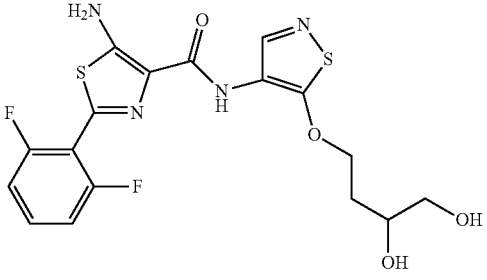 [SMILES: Nc1sc(-c2c(F)cccc2F)nc1C(=O)Nc1cnsc1OCCC(O)CO] | ¹H NMR (400 MHz, CD₃OD) δ: 1.88-2.05 (m, 2H), 3.28 (bs, 2H), 3.70 (bs, 1H), 4.15-4.35 (m, 2H), 7.08-7.26 (m, 2H), 7.47-7.67 (m, 1H), 9.10 (s, 1H) | M: 442 |

| | Structure | ¹HNMR | MS |
|---|---|---|---|
| 92 | 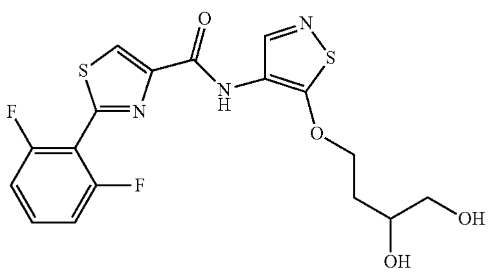 [SMILES: O=C(Nc1cnsc1OCCC(O)CO)c1csc(-c2c(F)cccc2F)n1] | ¹H NMR (400 MHz, CD₃OD) δ: 1.80-1.99 (m, 2H), 3.20 (bs, 2H), 3.70-3.75 (m, 1H), 4.10-4.34 (m, 2H), 7.09 (t, J = 9.16 Hz, 2H), 7.38-7.50 (m, 1H), 9.11 (s, 1H), 9.22 (s, 1H) | M: 427 |
| 93 | 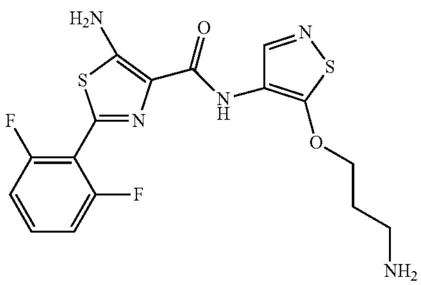 [SMILES: NCCCOc1sncc1NC(=O)c1nc(-c2c(F)cccc2F)sc1N] | ¹H NMR (400 MHz, CD₃OD) δ: 1.86 (bs, 2H), 2.81 (bs, 2H), 4.21 (bs, 2H), 7.21-7.33 (m, 2H), 7.55-7.72 (m, 1H), 9.10 (s, 1H) | M + 1: 412 |
| 94 | 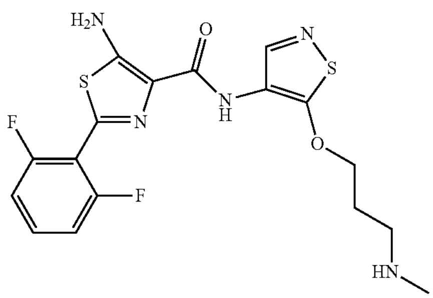 [SMILES: CNCCCOc1sncc1NC(=O)c1nc(-c2c(F)cccc2F)sc1N] | ¹H NMR (400 MHz, CD₃OD) δ: 1.91 (bs, 2H), 2.81 (bs, 2H), 2.85 (s, 3H), 4.22 (bs, 2H), 7.20-7.29 (m, 2H), 7.54-7.68 (m, 1H), 9.11 (s, 1H) | M + 1: 426 |
| 95 | 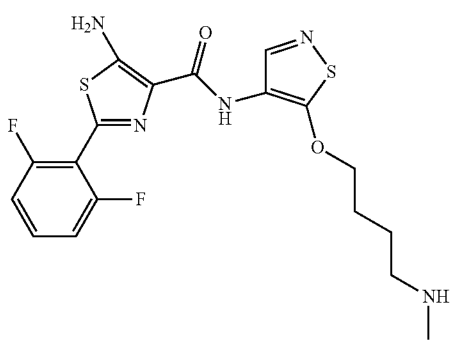 [SMILES: CNCCCCOc1sncc1NC(=O)c1nc(-c2c(F)cccc2F)sc1N] | ¹H NMR (400 MHz, CD₃OD) δ: 1.46-1.59 (m, 2H), 1.77-1.84 (m, 2H), 2.81-2.83 (m, 2H), 2.92 (s, 3H), 4.26 (t, J = 5.96 Hz, 2H), 7.10-7.29 (m, 2H), 7.44-7.65 (m, 1H), 9.10 (s, 1H) | M + 1: 440 |
| 96 | 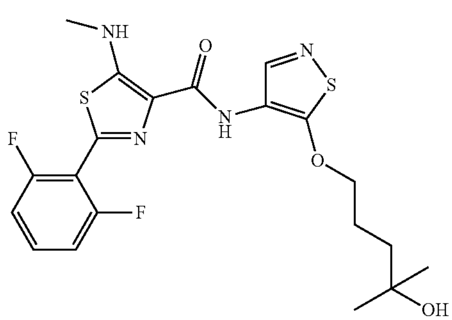 [SMILES: CNc1sc(-c2c(F)cccc2F)nc1C(=O)Nc1cnsc1OCCCC(C)(C)O] | ¹H NMR (400 MHz, CD₃OD) δ: 1.08 (s, 6H), 1.40-1.48 (m, 2H), 1.69-1.81 (m, 2H), 3.20 (s, 3H), 4.20 (t, J = 6.80 Hz, 2H), 7.09-7.25 (m, 2H), 7.50-7.69 (m, 1H), 9.10 (s, 1H) | M: 468 |

Example 97

The biochemical assays used to test the activities of the compounds of the present invention and their results.
In the present invention, the PIM activities of the compounds were tested by BioDuro (Building E, No. 29 Life Science Park Road, Changping District, Beijing, 102206, P.R. China). The method used for testing is PIM Kinase Activity Assay-IMAP Fluorescence Polarization Assay PIM Kinase Activity Assay-IMAP Fluorescence Polarization Assay 1. Principle PIM kinases are serine/threonine protein kinases, and they can phosphorylate 5-FAM labeled small peptide substrates. Fluorescence polarization is less for non-phosphorylated substrates since that can not bind to the binder (metal binding nanoparticles). On the other hand, fluorescence polarization is more for phosphorylated substrates since that can bind to the binder. The level of 5-FAM labeled small peptide substrates phosphorylation reflects the activities of PIM kinase. By measuring their ability of inhibiting PIM kinase of the compounds of the present invention, their activities of inhibiting PIM kinases can be determined 2. Instrument EnVision (PerkinElmer, Waltham, Mass.)

3. Reagents and 384 well plates

PIM1 (Millipore Cat. #14-573) (Millipore Corporation, Billerica, Mass.)
PIM2 (Millipore Cat. #14-607) (Millipore Corporation, Billerica, Mass.)
5-FAM labeled peptide (5-FAM-RSRHSSYPAGT, AnaSpec Cat. #63801) (AnaSpec Inc., Fremont, Calif.)
IMAP FP Screening Express kit (IMAP FP Screening kit) (Molecular Devices Cat. #R8127) (Molecular Devices, Sunnyvale, Calif.)
IMAP Progressive binding reagent
IMAP Progressive binding buffer A (5×)
IMAP Progressive binding buffer B (5×)
384-well black plate (Corning Cat. #3573) (Corning, Midland Mich.)

4. Assay Buffer

Tris-HCl (pH 7.2): 10 mM
$MgCl_2$: 10 mM
Triton X-100:0.01%
DTT: 2 mM

5. Procedure a) 10 mM compound stock solution is diluted to appropriate concentration with 100% DMSO, then diluted 10 fold to targeted concentration with test butter to keep DMSO concentration at 10%
b) Assay volume 10 ul:
1 ul of compound solution and 4 ul of enzyme (PIM-1 final concentration 0.025 nM, PIM-2 concentration 3 nM) is incubated at 23° C. for 15 min, 2.5 ul ATP (for PIM-1 and PIM-2, the final ATP concentrations are 30 uM and 5 uM respectively) 2.5 ul 5-FAM labeled peptide (final concentration 100 nM) was added to start the reaction. The reaction is run at 23° C. for 60 min DMSO is used in place of compound stock solution as maximum reference and assay buffer is used in place of enzyme as minimum reference.
c) add 30 ul IMAP binding reagent (containing 75% IMAP Buffer A, 25% IMAP Buffer B, 1/600 dilution of beads) to stop the reaction, incubated at room temperature for 60 min
d) Measure fluorescence polarization, excitation wavelength: 485 nm, emission wavelength 530 nm.

6. Data process $IC_{50}$ values were calculated using Graphpad Prism®.
PIM kinase assays showed that all 96 compounds in Example 1 through 96 can significantly inhibit PIM kinase activities. At 3 µM concentration, almost all compounds except the compounds listed below showed greater than 50% inhibition against PIM-1 kinase activity, some showed 100% inhibition. These compounds can also inhibit the PIM-2 and PIM-3 activities and some can inhibit 100% of the activities at 3 µM concentration.

The following compounds showed 20-50% inhibition of PIM-1 activity 3 µM concentration:

tert-butyl 4-(4-((5-morpholinoisothiazol-4-yl)carbamoyl)thiazol-2-yl)piperidine-1-carboxylate (25);
N-(5-morpholinoisothiazol-4-yl)-2-(piperidin-4-yl)thiazole-4-carboxamide (26);
2-(2,3-dihydrobenzo[b][1,4]dioxin-2-yl)-N-(5-morpholinoisothiazol-4-yl)thiazole-4-carboxamide (28);
2-morpholino-N-(5-(piperazin-1-yl)isothiazol-4-yl)thiazole-4-carboxamide (36);
2-acetamido-N-(5-(piperazin-1-yl)isothiazol-4-yl)thiazole-4-carboxamide (39);
2-(2,3-dihydrobenzo[b][1,4]dioxin-2-yl)-N-(5-(piperazin-1-yl)isothiazol-4-yl)thiazole-4-carboxamide (40);
1-(2-fluorophenyl)-5-methyl-N-(5-(piperazin-1-yl)isothiazol-4-yl)-1H-pyrazole-3-carboxamide (41);
3-(2-fluorophenyl)-N-(5-(piperazin-1-yl)isothiazol-4-yl)-1H-pyrazole-5-carboxamide (42);
2-phenyl-N-(5-(piperazin-1-yl)isothiazol-4-yl)oxazole-4-carboxamide (43);
6-(2,6-difluorophenyl)-N-(5-(5-hydroxy-3,4-dihydroisoquinolin-2(1H)-yl)isothiazol-4-yl)picolinamide (52).

I claim:

1. A compound having a structure of Formula I:

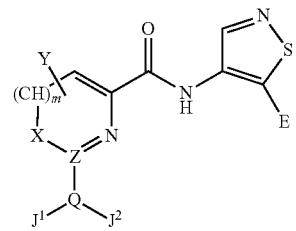

I wherein m is 0 or 1, and when m is 0, X is S, O, N, or CH; when m is 1, X is CH or N;

Z is CH or N;

Y is H, $N(R^1R^2)$, or $N(R^1C(=O)R^2)$, and $R^1$ and $R^2$ are each independently selected from H or an optionally substituted $C_1$-$C_8$ hydrocarbon group;

E is $N(R^3R^4)$,

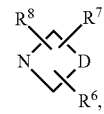

a substituted phenyl group

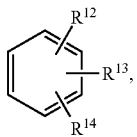

a 5- or 6-membered hetero aromatic group containing 1 or 2 hetero atoms and substituted with $R^{20}$ and $R^{21}$, or $OR^{22}$:

when E is the $N(R^3R^4)$, $R^3$ and $R^4$ are each independently selected from an optionally substituted $C_1$-$C_8$ hydrocarbon group;

when E is the

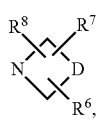

D is a linear chain of 1-5 $CH_2$ and optionally substituted with an O or a $NR^5$ group; $R^5$ is H or an optionally substituted $C_1$-$C_8$ hydrocarbon group; $R^6$, $R^7$, and $R^8$ are each independently selected from H, halogen, $OR^9$, $NR^{10}R^{11}$, or an optionally substituted $C_1$-$C_8$ hydrocarbon group, or $R^6$, $R^7$, $R^8$ are joined together to form a chain so that the ring to which they are attached is an optionally substituted $C_6$-$C_{14}$ membered spiral ring, bicyclic ring, or fused ring group; $R^9$, $R^{10}$, and $R^{11}$ are each independently selected from H or an optionally substituted $C_1$-$C_8$ hydrocarbon group;

when E is the substituted phenyl group

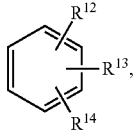

$R^{12}$, $R^{13}$, and $R^{14}$ are each independently selected from H, halogen, $OR^{15}$, $NR^{16}R^{17}$, $C(=O)NR^{18}R^{19}$, or an optionally substituted $C_1$-$C_8$ hydrocarbon group; and $R^{15}$, $R^{16}$, $R^{17}$, $R^{18}$, and $R^{19}$ are each independently selected from H or an optionally substituted $C_1$-$C_8$ hydrocarbon group;

when E is the 5 or 6 membered hetero aromatic group containing 1 or 2 hetero atoms and substituted with $R^{20}$ and $R^{21}$, the hetero atom is N or S; and $R^{20}$ and $R^{21}$ are each independently selected from H, halogen, $OR^{15}$, $NR^{16}R^{17}$, $C(=O)NR^{18}R^{19}$, or an optionally substituted $C_1$-$C_8$ hydrocarbon group;

when E is $OR^{22}$; $R^{22}$ is an optionally substituted $C_1$-$C_8$ hydrocarbon group or a group having a formula

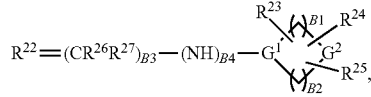

wherein $R^{23}$, $R^{24}$, and $R^{25}$ are each independently selected from H, halogen, $OR^{15}$, $NR^{16}R^{17}$, $C(=O)R^{18}R^{19}$, an optionally substituted $C_1$-$C_8$ hydrocarbon group, or $R^{23}$, $R^{24}$ and $R^{25}$, together with atoms to which they are attached are joined together to form a chain so that the ring to which they are attached is a substituted $C_6$-$C_{14}$ membered spiral ring, bicyclic ring, or fused ring group; $G^1$ is CH or N; $G^2$ is $NR^{28}$, $CHR^{29}$, or O; B1 and B2 each independently represent 0, 1, 2, or 3; B3 is 0, 1, or 2; B4 is 0 or 1; $R^{26}$ and $R^{27}$ are each independently selected from H or an optionally substituted $C_1$-$C_8$ hydrocarbon group; $R^{28}$ is H, an optionally substituted hydrocarbon group, an optionally substituted cyclic hydrocarbon group, an optionally substituted heterocyclic hydrocarbon group, $C(=O)R^{30}$, $C(=O)OR^{30}$, or $C(=O)NHR^{30}$; $R^{29}$ is OH, $NHR^{30}$, $C(=O)OR^{30}$, or $C(=O)NHR^{30}$; $R^{30}$ is H or an optionally substituted $C_1$-$C_8$ hydrocarbon group;

Q is C, CH, or N;

$J^1$ and $J^2$ are each independently selected from H, an optionally substituted $C_1$-$C_8$ hydrocarbon group, $OR^{31}$, $NHR^{31}$, or $C(=O)R^{31}$; $R^{31}$ is H or an optionally substituted $C_1$-$C_8$ hydrocarbon group;

or $J^1$, $J^2$, and a CH to which $J^1$ and $J^2$ are attached are joined together to form a $C_3$-$C_8$ membered cycloalkyl, and the $C_3$-$C_8$ membered cycloalkyl, on one or more position, is optionally substituted with a halogen, $OR^{32}$, $NHR^{33}$, an optionally substituted $C_1$-$C_8$ hydrocarbon group, or a substituted $C_1$-$C_8$ hydrocarbon group having the substituents joined together to form a chain so that the ring to which the substituents are attached is a substituted $C_6$-$C_{14}$ membered spiral ring, bicyclic ring, or fused ring group; $R^{32}$ and $R^{33}$ are each independently selected from H, an optionally substituted $C_1$-$C_8$ hydrocarbon group, an optionally substituted $C_3$-$C_8$ cyclic hydrocarbon group, an optionally substituted $C_4$-$C_7$ membered heterocyclic hydrocarbon group, $C(=O)R^{34}$, $C(=O)OR^{34}$, or $C(=O)NHR^{34}$; $R^{34}$ is H or an optionally substituted $C_1$-$C_8$ hydrocarbon group;

or $J^1$, $J^2$, an atom to which $J^1$ and $J^2$ are attached, and at least one hetero atom are joined together to form a $C_4$-$C_7$ membered heterocycloalkyl, and the $C_4$-$C_7$ membered heterocycloalkyl, on one or more position, is optionally substituted with a halogen, $OR^{32}$, $NHR^{33}$, an optionally substituted $C_1$-$C_8$ hydrocarbon group, or a substituted $C_1$-$C_8$ hydrocarbon group having the substituents joined together to form a chain so that the ring to which the substituents are attached is a substituted $C_6$-$C_{14}$ membered spiral ring, bicyclic ring, or fused ring group;

or $J^1$, $J^2$, and a carbon atom to which $J^1$ and $J^2$ are attached are joined together to form an aromatic ring, or $J^1$, $J^2$, a carbon atom to which $J^1$ and $J^2$ are attached, and at least one heteroatom are joined together to form a $C_5$-$C_6$ membered hetero aromatic ring, and on the aromatic ring or the $C_5$-$C_6$ membered hetero aromatic ring, one or more position is optionally substituted with a halogen, CN, $OR^{32}$, $NHR^{33}$, an optionally substituted $C_1$-$C_8$ hydrocarbon group, or a substituted $C_1$-$C_8$ hydrocarbon group having the substituents joined together to form a chain so that the ring to which the substituents are attached is an optionally substituted $C_6$-$C_{14}$ membered aromatic spiral ring, bicyclic ring, or fused ring group;

or $J^1$, $J^2$, and a nitrogen atom to which $J^1$ and $J^2$ are attached are joined together to form a $C_4$-$C_7$ membered heterocycloalkyl group, or $J^1$, $J^2$, a nitrogen atom to which $J^1$ and $J^2$ are attached, and at least one hetero atom are joined together to form a $C_4$-$C_7$ membered heterocycloalkyl group; on the $C_4$-$C_7$ membered heterocycloalkyl group, one or more position is optionally substituted with a halogen, CN, $OR^{32}$, $NHR^{33}$, an optionally substituted $C_1$-$C_8$ hydrocarbon group, or a substituted $C_1$-$C_8$ hydrocarbon group having the substituents joined together to form a chain so that the ring to which the substituents are attached is an optionally substituted $C_6$-$C_{14}$ membered aromatic spiral ring, bicyclic ring, or fused ring group.

2. The compound according to claim 1, wherein E is the 5 membered hetero aromatic group containing N and S hetero atoms and substituted with $R^{20}$ and $R^{21}$ as in

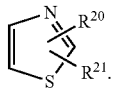

3. The compound according to claim 1, wherein the $J^1$, $J^2$, and the carbon atom to which the $J^1$ and $J^2$ are attached are joined together to form a benzene or a naphthlene, or the $J^1$, $J^2$, the carbon atom to which the $J^1$ and $J^2$ are attached, and at least one heteroatom are joined together to form a $C_5$-$C_6$ membered aromatic heterocycle that is a pyridine, pyrimidine, pyrazine, imidazole, thiazole, isoxazole, oxazole or pyrrole.

4. A compound according to claim 1, wherein the compound is 5-amino-2-(2,6-difluorophenyl)-N-(5-(piperidin-4-yloxy)isothiazol-4-yl)thiazole-4-carboxamide (1), N-(5-(azepan-4-yloxy)isothiazol-4-yl)-2-(2,6-difluorophenyl) thiazole-4-carboxamide (2), N-(5-(4-carbamoylphenyl) isothiazol-4-yl)-2-(2,6-difluorophenyl)thiazole-4-carboxamide (3), N-(5-(4-carbamoylphenyl)isothiazol-4-yl)-6-(2,6-difluorophenyl)picolinamide (4), 2-(2,6-difluorophenyl)-N-(5-(2-morpholinothiazol-4-yl)isothiazol-4-yl)thiazole-4-carboxamide (5), 2-(2,6-difluorophenyl)-N-(5-morpholinoisothiazol-4-yl)thiazole-4-carboxamide (6), 5-amino-2-(2,6-difluorophenyl)-N-(5-morpholinoisothiazol-4-yl)thiazole-4-carboxamide (7), 6-(2,6-difluorophenyl)-N-(5-morpholinoisothiazol-4-yl)picolinamide (8), tert-butyl (1-(4-(2-(2,6-difluorophenyl)thiazole-4-carboxamido)isothiazol-5-yl)piperidin-4-yl)carbamate (9), N-(5-(4-aminopiperidin-1-yl)isothiazol-4-yl)-2-(2,6-difluorophenyl)thiazole-4-carboxamide (10), 5-amino-N-(5-(4-aminopiperidin-1-yl)isothiazol-4-yl)-2-(2,6-difluorophenyl) thiazole-4-carboxamide (11), N-(5-(4-aminopiperidin-1-yl) isothiazol-4-yl)-6-(2,6-difluorophenyl)picolinamide (12), tert-butyl (1-(4-(2-(2,6-difluorophenyl)thiazole-4-carboxamido)isothiazol-5-yl)piperidin-3-yl)carbamate (13), N-(5-(3-aminopiperidin-1-yl)isothiazol-4-yl)-2-(2,6-difluorophenyl)thiazole-4-carboxamide (14), tert-butyl (1-(4-(5-amino-2-(2,6-difluorophenyl)thiazole-4-carboxamido)isothiazol-5-yl)piperidin-3-yl)carbamate (15), N-(5-(3-aminopiperidin-1-yl)isothiazol-4-yl)-6-(2,6-difluorophenyl)picolinamide (16), 5-amino-2-(2,6-difluorophenyl)-N-(5-(4-hydroxypiperidin-1-yl)isothiazol-4-yl)thiazole-4-carboxamide (17), 2-(2,6-difluorophenyl)-N-(5-(4-hydroxypiperidin-1-yl)isothiazol-4-yl)thiazole-4-carboxamide (18), N-(5-morpholinoisothiazol-4-yl)-2-(pyridin-4-yl)thiazole-4-carboxamide (19), N-(5-morpholinoisothiazol-4-yl)-2-(pyridin-3-yl)thiazole-4-carboxamide (20), N-(5-morpholinoisothiazol-4-yl)-2-(pyridin-2-yl)thiazole-4-carboxamide (21), 2-isopropyl-N-(5-morpholinoisothiazol-4-yl)thiazole-4-carboxamide (22), N-(5-morpholinoisothiazol-4-yl)-2-(piperidin-1-yl)thiazole-4-carboxamide (23), 2-morpholino-N-(5-morpholinoisothiazol-4-yl)thiazole-4-carboxamide (24), tert-butyl 4-(4-((5-morpholinoisothiazol-4-yl)carbamoyl)thiazol-2-yl) piperidine-1-carboxylate (25), N-(5-morpholinoisothiazol-4-yl)-2-(pyridin-4-yl)thiazole-4-carboxamide (26), 2-acetamido-N-(5-morpholinoisothiazol-4-yl)thiazole-4-carboxamide (27), 2-(2,3-dihydrobenzo[b][1,4]dioxin-2-yl)-N-(5-morpholinoisothiazol-4-yl)thiazole-4-carboxamide (28), 1-(2-fluorophenyl)-5-methyl-N-(5-morpholinoisothiazol-4-yl)-1H-pyrazole-3-carboxamide (29), N-(5-morpholinoisothiazol-4-yl)-2-phenyloxazole-4-carboxamide (30), N-(5-(piperazin-1-yl)isothiazol-4-yl)-2-(pyridin-4-yl)thiazole-4-carboxamide (31), N-(5-(piperazin-1-yl)isothiazol-4-yl)-2-(pyridin-3-yl)thiazole-4-carboxamide (32), N-(5-(piperazin-1-yl)isothiazol-4-yl)-2-(pyridin-2-yl)thiazole-4-carboxamide (33), 2-isopropyl-N-(5-(piperazin-1-yl) isothiazol-4-yl)thiazole-4-carboxamide (34), N-(5-(piperazin-1-yl)isothiazol-4-yl)-2-(piperidin-1-yl)thiazole-4-carboxamide (35), 2-morpholino-N-(5-(piperazin-1-yl) isothiazol-4-yl)thiazole-4-carboxamide (36), tert-butyl 4-(4-(2-(1-(tert-butoxycarbonyl)piperidin-4-yl)thiazole-4-carboxamido)isothiazol-5-yl)piperazine-1-carboxylate (37), N-(5-(piperazin-1-yl)isothiazol-4-yl)-2-(piperidin-4-yl)thiazole-4-carboxamide (38), 2-acetamido-N-(5-(piperazin-1-yl)isothiazol-4-yl)thiazole-4-carboxamide (39), 2-(2,3-dihydrobenzo[b][1,4]dioxin-2-yl)-N-(5-(piperazin-1-yl) isothiazol-4-yl)thiazole-4-carboxamide (40), 1-(2-fluorophenyl)-5-methyl-N-(5-(piperazin-1-yl)isothiazol-4-yl)-1H-pyrazole-3-carboxamide (41), 3-(2-fluorophenyl)-N-(5-(piperazin-1-yl)isothiazol-4-yl)-1H-pyrazole-5-carboxamide (42), 2-phenyl-N-(5-(piperazin-1-yl) isothiazol-4-yl)oxazole-4-carboxamide (43), 2-(2,6-difluorophenyl)-N-(5-(4-(1-hydroxyethyl)piperidin-1-yl) isothiazol-4-yl)thiazole-4-carboxamide (44), N-(5-(3,8-diazabicyclo[3.2.1]octan-3-yl)isothiazol-4-yl)-2-(2,6-difluorophenyl)thiazole-4-carboxamide (45), 2-(2,6-difluorophenyl)-N-(5-(piperazin-1-yl)isothiazol-4-yl) thiazole-4-carboxamide (46), 6-(2,6-difluorophenyl)-N-(5-(4-hydroxypiperidin-1-yl)isothiazol-4-yl)picolinamide (47), 2-(2,6-difluorophenyl)-N-(5-(4-hydroxyazepan-1-yl) isothiazol-4-yl)thiazole-4-carboxamide (48), 5-amino-2-(2,6-difluorophenyl)-N-(5-(4-hydroxyazepan-1-yl)isothiazol-4-yl)thiazole-4-carboxamide (49), 6-(2,6-difluorophenyl)-N-(5-(4-hydroxyazepan-1-yl)isothiazol-4-yl)picolinamide (50), 2-(2,6-difluorophenyl)-N-(5-(5-hydroxy-3,4-dihydroisoquinolin-2(1H)-yl)isothiazol-4-yl)thiazole-4-carboxamide (51), 6-(2,6-difluorophenyl)-N-(5-(5-hydroxy-3,4-dihydroisoquinolin-2(1H)-yl)isothiazol-4-yl)picolinamide (52), (S)-2-(2,6-difluorophenyl)-N-(5-(3-(hydroxymethyl) morpholino)isothiazol-4-yl)thiazole-4-carboxamide (53), 2-(2,6-difluorophenyl)-N-(5-(piperidin-4-yloxy)isothiazol-4-yl)thiazole-4-carboxamide (54), N-(5-(azetidin-3-yl-methoxy)isothiazol-4-yl)-2-(2,6-difluorophenyl)thiazole-4-carboxamide (55), 3-amino-N-(5-(azetidin-3-yloxy) isothiazol-4-yl)-6-(2,6-difluorophenyl)picolinamide (56), N-(5-(azetidin-3-yloxy)isothiazol-4-yl)-2-(2,6-difluorophenyl)thiazole-4-carboxamide (57), 6-(2,6-difluorophenyl)-N-(5-(piperidin-4-yloxy)isothiazol-4-yl)-picolinamide (58), 5-amino-N-(5-((4-carbamoylcyclohexyl)oxy)isothiazol-4-yl)-2-(2,6-difluorophenyl)thiazole-4-carboxamide (59), 2-(2,6-difluorophenyl)-N-(5-((3-methyloxetan-3-yl)methoxy)isothiazol-4-yl)thiazole-4-carboxamide (60), 3-amino-N-(5-(3-aminopiperidin-1-yl)isothiazol-4-yl)-6-(2,6-difluorophenyl)-picolinamide (61), 2-(2,6-difluorophenyl)-N-(5-(piperidin-4-ylmethoxy)isothiazol-4-yl)thiazole-4-carboxamide (62), 3-amino-6-(2,6-difluorophenyl)-N-(5-(piperidin-4-ylmethoxy)isothiazol-4-yl)picolinamide (63), (S)-2-(2,6-difluorophenyl)-N-(5-(pyrrolidin-3-yloxy) isothiazol-4-yl)thiazole-4-carboxamide (64), (R)-2-(2,6-difluorophenyl)-N-(5-(pyrrolidin-3-yloxy)isothiazol-4-yl)thiazole-4-carboxamide (65), 5-amino-N-(5-(3-aminopiperidin-1-yl)isothiazol-4-yl)-2-(2,6-difluorophenyl)thiazole-4-carboxamide (66), 2-(2,6-difluorophenyl)-N-(5-(3-hydroxypiperidin-1-yl)isothiazol-4-yl)thiazole-4-carboxamide (67), 5-amino-2-(2,6-difluorophenyl)-N-(5-(3- hydroxypiperidin-1-yl)isothiazol-4-yl)thiazole-4-carboxamide (68), (S)-5-amino-2-(2,6-difluorophenyl)-N-(5-(pyrrolidin-3-yloxy)isothiazol-4-yl)thiazole-4-carboxamide (69), (R)-5-amino-2-(2,6-difluorophenyl)-N-(5-(pyrrolidin-3-yloxy)isothiazol-4-yl)thiazole-4-carboxamide (70), 3-amino-6-(2,6-difluorophenyl)-N-(5-(3-hydroxypiperidin-1-yl)isothiazol-4-yl)picolinamide (71), 6-(2,6-difluorophenyl)-N-(5-(3-hydroxypiperidin-1-yl)isothiazol-4-yl)picolinamide (72), 5-amino-N-(5-(azepan-4-yloxy)isothiazol-4-yl)-2-(2,6-difluorophenyl)thiazole-4-carboxamide (73), 3-amino-6-(2,6-difluorophenyl)-N-(5-(3-hydroxypropoxy)isothiazol-4-yl)picolinamide (74), 5-amino-N-(5-((trans-4-aminocyclohexyl)oxy)isothiazol-4-yl)-2-(2,6-difluorophenyl)thiazole-4-carboxamide (75), 5-amino-2-(2,6-difluorophenyl)-N-(5-(piperidin-4-ylmethoxy)isothiazol-4-yl)thiazole-4-carboxamide (76), 5-amino-N-(5-(4-aminobutoxy)isothiazol-4-yl)-2-(2,6-difluorophenyl)thiazole-4-carboxamide (77), 5-amino-2-(2,6-difluorophenyl)-N-(5-(4-hydroxybutoxy)isothiazol-4-yl)thiazole-4-carboxamide (78), 5-amino-2-(2,6-difluorophenyl)-N-(5-(2-hydroxyethoxy)isothiazol-4-yl)thiazole-4-carboxamide (79), 5-amino-2-(2,6-difluorophenyl)-N-(5-(3-hydroxypropoxy)isothiazol-4-yl)thiazole-4-carboxamide (80), 5-amino-2-(2,6-difluorophenyl)-N-(5-(3-hydroxypropoxy)isothiazol-4-yl)thiazole-4-carboxamide (81), 5-amino-2-(2,6-difluorophenyl)-N-(5-(3-hydroxy-3-methylbutoxy)isothiazol-4-yl)thiazole-4-carboxamide (82), 2-(2,6-difluorophenyl)-5-formamido-N-(5-((4-hydroxy-4-methylpentyl)oxy)isothiazol-4-yl)thiazole-4-carboxamide (83), 5-amino-2-(2,6-difluorophenyl)-N-(5-((4-hydroxypentyl)oxy)isothiazol-4-yl)thiazole-4-carboxamide (84), 2-(2,6-difluorophenyl)-N-(5-((4-hydroxypentyl)oxy)isothiazol-4-yl)thiazole-4-carboxamide (85), 5-amino-2-(2,6-difluorophenyl)-N-(5-((4-hydroxy-4-methylpentyl)oxy)isothiazol-4-yl)thiazole-4-carboxamide (86), 2-(2,6-difluorophenyl)-N-(5-((4-hydroxy-4-methylpentyl)oxy)isothiazol-4-yl)thiazole-4-carboxamide (87), 5-amino-2-(2,6-difluorophenyl)-N-(5-(2-(2,2-dimethyl-1,3-dioxolan-4-yl)ethoxy)isothiazol-4-yl)thiazole-4-carboxamide (88), 5-amino-2-(2,6-difluorophenyl)-N-(5-((2,2-dimethyl-1,3-dioxolan-4-yl)methoxy)isothiazol-4-yl)thiazole-4-carboxamide (89), 5-amino-2-(2,6-difluorophenyl)-N-(5-(2,3-dihydroxypropoxy)isothiazol-4-yl)thiazole-4-carboxamide (90), 5-amino-2-(2,6-difluorophenyl)-N-(5-(3,4-dihydroxybutoxy)isothiazol-4-yl)thiazole-4-carboxamide (91), 2-(2,6-difluorophenyl)-N-(5-(3,4-dihydroxybutoxy)isothiazol-4-yl)thiazole-4-carboxamide (92), 5-amino-N-(5-(3-aminopropoxy)isothiazol-4-yl)-2-(2,6-difluorophenyl)thiazole-4-carboxamide (93), 5-amino-2-(2,6-difluorophenyl)-N-(5-(3-(methylamino)propoxy)isothiazol-4-yl)thiazole-4-carboxamide (94), 5-amino-2-(2,6-difluorophenyl)-N-(5-(4-(methylamino)butoxy)isothiazol-4-yl)thiazole-4-carboxamide (95), or 2-(2,6-difluorophenyl)-N-(5-((4-hydroxy-4-methylpentyl)oxy)isothiazol-4-yl)-5-(methylamino)thiazole-4-carboxamide (96).

5. A compound according to claim 4, wherein the compound is 5-amino-2-(2,6-difluorophenyl)-N-(5-(piperidin-4-yloxy)isothiazol-4-yl)thiazole-4-carboxamide (1), N-(5-(azepan-4-yloxy)isothiazol-4-yl)-2-(2,6-difluorophenyl)thiazole-4-carboxamide (2), N-(5-(4-carbamoylphenyl)isothiazol-4-yl)-2-(2,6-difluorophenyl)thiazole-4-carboxamide (3), N-(5-(4-carbamoylphenyl)isothiazol-4-yl)-6-(2,6-difluorophenyl)picolinamide (4), 2-(2,6-difluorophenyl)-N-(5-(2-morpholinothiazol-4-yl)isothiazol-4-yl)thiazole-4-carboxamide (5), N-(5-(4-aminopiperidin-1-yl)isothiazol-4-yl)-2-(2,6-difluorophenyl)thiazole-4-carboxamide (10), 5-amino-N-(5-(4-aminopiperidin-1-yl)isothiazol-4-yl)-2-(2,6-difluorophenyl)thiazole-4-carboxamide (11), N-(5-(4-aminopiperidin-1-yl)isothiazol-4-yl)-6-(2,6-difluorophenyl)picolinamide (12), N-(5-(3-aminopiperidin-1-yl)isothiazol-4-yl)-2-(2,6-difluorophenyl)thiazole-4-carboxamide (14), N-(5-(3-aminopiperidin-1-yl)isothiazol-4-yl)-6-(2,6-difluorophenyl)picolinamide (16), 5-amino-2-(2,6-difluorophenyl)-N-(5-(4-hydroxypiperidin-1-yl)isothiazol-4-yl)thiazole-4-carboxamide (17), 2-(2,6-difluorophenyl)-N-(5-(4-hydroxypiperidin-1-yl)isothiazol-4-yl)thiazole-4-carboxamide (18), N-(5-morpholinoisothiazol-4-yl)-2-(pyridin-2-yl)thiazole-4-carboxamide (21), N-(5-(piperazin-1-yl)isothiazol-4-yl)-2-(pyridin-2-yl)thiazole-4-carboxamide (33), N-(5-(3,8-diazabicyclo[3.2.1]octan-3-yl)isothiazol-4-yl)-2-(2,6-difluorophenyl)thiazole-4-carboxamide (45), 2-(2,6-difluorophenyl)-N-(5-(piperazin-1-yl)isothiazol-4-yl)thiazole-4-carboxamide (46), 2-(2,6-difluorophenyl)-N-(5-(4-hydroxyazepan-1-yl)isothiazol-4-yl)thiazole-4-carboxamide (48), 5-amino-2-(2,6-difluorophenyl)-N-(5-(4-hydroxyazepan-1-yl)isothiazol-4-yl)thiazole-4-carboxamide (49), 6-(2,6-difluorophenyl)-N-(5-(4-hydroxyazepan-1-yl)isothiazol-4-yl)picolinamide (50), 2-(2,6-difluorophenyl)-N-(5-(piperidin-4-yloxy)isothiazol-4-yl)thiazole-4-carboxamide (54), N-(5-(azetidin-3-ylmethoxy)isothiazol-4-yl)-2-(2,6-difluorophenyl)thiazole-4-carboxamide (55), 3-amino-N-(5-(azetidin-3-yloxy)isothiazol-4-yl)-6-(2,6-difluorophenyl)picolinamide (56), N-(5-(azetidin-3-yloxy)isothiazol-4-yl)-2-(2,6-difluorophenyl)thiazole-4-carboxamide (57), 6-(2,6-difluorophenyl)-N-(5-(piperidin-4-yloxy)isothiazol-4-yl)-picolinamide (58), 5-amino-N-(5-((4-carbamoylcyclohexyl)oxy)isothiazol-4-yl)-2-(2,6-difluorophenyl)thiazole-4-carboxamide (59), 2-(2,6-difluorophenyl)-N-(5-((3-methyloxetan-3-yl)methoxy)isothiazol-4-yl)thiazole-4-carboxamide (60), 3-amino-N-(5-(3-aminopiperidin-1-yl)isothiazol-4-yl)-6-(2,6-difluorophenyl)-picolinamide (61), 2-(2,6-difluorophenyl)-N-(5-(piperidin-4-ylmethoxy)isothiazol-4-yl)thiazole-4-carboxamide (62), 3-amino-6-(2,6-difluorophenyl)-N-(5-(piperidin-4-ylmethoxy)isothiazol-4-yl)-picolinamide (63), (S)-2-(2,6-difluorophenyl)-N-(5-(pyrrolidin-3-yloxy)isothiazol-4-yl)thiazole-4-carboxamide (64), (R)-2-(2,6-difluorophenyl)-N-(5-(pyrrolidin-3-yloxy)isothiazol-4-yl)thiazole-4-carboxamide (65), 5-amino-N-(5-(3-aminopiperidin-1-yl)isothiazol-4-yl)-2-(2,6-difluorophenyl)thiazole-4-carboxamide (66), 2-(2,6-difluorophenyl)-N-(5-(3-hydroxypiperidin-1-yl)isothiazol-4-yl)thiazole-4-carboxamide (67), 5-amino-2-(2,6-difluorophenyl)-N-(5-(3-hydroxypiperidin-1-yl)isothiazol-4-yl)thiazole-4-carboxamide (68), (S)-5-amino-2-(2,6-difluorophenyl)-N-(5-(pyrrolidin-3-yloxy)isothiazol-4-yl)thiazole-4-carboxamide (69), (R)-5-amino-2-(2,6-difluorophenyl)-N-(5-(pyrrolidin-3-yloxy)isothiazol-4-yl)thiazole-4-carboxamide (70), 3-amino-6-(2,6-difluorophenyl)-N-(5-(3-hydroxypiperidin-1-yl)isothiazol-4-yl)picolinamide (71), 6-(2,6-difluorophenyl)-N-(5-(3-hydroxypiperidin-1-yl)isothiazol-4-yl)picolinamide (72), 5-amino-N-(5-(azepan-4-yloxy)isothiazol-4-yl)-2-(2,6-difluorophenyl)thiazole-4-carboxamide (73), 3-amino-6-(2,6-difluorophenyl)-N-(5-(3-hydroxypropoxy)isothiazol-4-yl)picolinamide (74), 5-amino-N-(5-((trans-4-aminocyclohexyl)oxy)isothiazol-4-yl)-2-(2,6-difluorophenyl)thiazole-4-carboxamide (75), 5-amino-2-(2,6-difluorophenyl)-N-(5-(piperidin-4-ylmethoxy)isothiazol-4-yl)thiazole-4-carboxamide (76), 5-amino-N-(5-(4-aminobutoxy)isothiazol-4-yl)-2-(2,6-difluorophenyl)thiazole-4-carboxamide (77), 5-amino-2-(2,6-difluorophenyl)-N-(5-(4-hydroxybutoxy)isothiazol-4-yl)thiazole-4-carboxamide (78), 5-amino-2-(2,6- difluorophenyl)-N-(5-(2-hydroxyethoxy)isothiazol-4-yl)thiazole-4-carboxamide (79), 5-amino-2-(2,6-difluorophenyl)-N-(5-(3-hydroxypropoxy)isothiazol-4-yl)thiazole-4-carboxamide (80), 5-amino-2-(2,6-difluorophenyl)-N-(5-(3-hydroxypropoxy)isothiazol-4-yl)thiazole-4-carboxamide (81), 5-amino-2-(2,6-difluorophenyl)-N-(5-(3-hydroxy-3-methylbutoxy)isothiazol-4-yl)thiazole-4-carboxamide (82), 2-(2,6-difluorophenyl)-5-formamido-N-(5-((4-hydroxy-4-methylpentyl)oxy)isothiazol-4-yl)thiazole-4-carboxamide (83), 5-amino-2-(2,6-difluorophenyl)-N-(5-((4-hydroxypentyl)oxy)isothiazol-4-yl)thiazole-4-carboxamide (84), 2-(2,6-difluorophenyl)-N-(5-((4-hydroxypentyl)oxy)isothiazol-4-yl)thiazole-4-carboxamide (85), 5-amino-2-(2,6-difluorophenyl)-N-(5-((4-hydroxy-4-methylpentyl)oxy)isothiazol-4-yl)thiazole-4-carboxamide (86), 2-(2,6-difluorophenyl)-N-(5-((4-hydroxy-4-methylpentyl)oxy)isothiazol-4-yl)thiazole-4-carboxamide (87), 5-amino-2-(2,6-difluorophenyl)-N-(5-(2-(2,2-dimethyl-1,3-dioxolan-4-yl)ethoxy)isothiazol-4-yl)thiazole-4-carboxamide (88), 5-amino-2-(2,6-difluorophenyl)-N-(5-((2,2-dimethyl-1,3-dioxolan-4-yl)methoxy)isothiazol-4-yl)thiazole-4-carboxamide (89), 5-amino-2-(2,6-difluorophenyl)-N-(5-(3,4-dihydroxybutoxy)isothiazol-4-yl)thiazole-4-carboxamide (91), 2-(2,6-difluorophenyl)-N-(5-(3,4-dihydroxybutoxy)isothiazol-4-yl)thiazole-4-carboxamide (92), 5-amino-N-(5-(3-aminopropoxy)isothiazol-4-yl)-2-(2,6-difluorophenyl)thiazole-4-carboxamide (93), 5-amino-2-(2,6-difluorophenyl)-N-(5-(3-(methylamino)propoxy)isothiazol-4-yl)thiazole-4-carboxamide (94), 5-amino-2-(2,6-difluorophenyl)-N-(5-(4-(methylamino)butoxy)isothiazol-4-yl)thiazole-4-carboxamide (95), or 2-(2,6-difluorophenyl)-N-(5-((4-hydroxy-4-methylpentyl)oxy)isothiazol-4-yl)-5-(methylamino)thiazole-4-carboxamide (96).

6. A compound according to claim 5, wherein the compound is 5-amino-2-(2,6-difluorophenyl)-N-(5-(piperidin-4-yloxy)isothiazol-4-yl)thiazole-4-carboxamide (1), N-(5-(azepan-4-yloxy)isothiazol-4-yl)-2-(2,6-difluorophenyl)thiazole-4-carboxamide (2), N-(5-(4-carbamoylphenyl)isothiazol-4-yl)-2-(2,6-difluorophenyl)thiazole-4-carboxamide (3), N-(5-(4-carbamoylphenyl)isothiazol-4-yl)-6-(2,6-difluorophenyl)picolinamide (4), 2-(2,6-difluorophenyl)-N-(5-(2-morpholinothiazol-4-yl)isothiazol-4-yl)thiazole-4-carboxamide (5), N-(5-(4-aminopiperidin-1-yl)isothiazol-4-yl)-2-(2,6-difluorophenyl)thiazole-4-carboxamide (10), 5-amino-N-(5-(4-aminopiperidin-1-yl)isothiazol-4-yl)-2-(2,6-difluorophenyl)thiazole-4-carboxamide (11), N-(5-(4-aminopiperidin-1-yl)isothiazol-4-yl)-6-(2,6-difluorophenyl)picolinamide (12), N-(5-(3-aminopiperidin-1-yl)isothiazol-4-yl)-2-(2,6-difluorophenyl)thiazole-4-carboxamide (14), N-(5-(3-aminopiperidin-1-yl)isothiazol-4-yl)-6-(2,6-difluorophenyl)picolinamide (16), 5-amino-2-(2,6-difluorophenyl)-N-(5-(4-hydroxypiperidin-1-yl)isothiazol-4-yl)thiazole-4-carboxamide (17), 2-(2,6-difluorophenyl)-N-(5-(4-hydroxypiperidin-1-yl)isothiazol-4-yl)thiazole-4-carboxamide (18), N-(5-(3,8-diazabicyclo[3.2.1]octan-3-yl)isothiazol-4-yl)-2-(2,6-difluorophenyl)thiazole-4-carboxamide (45), 5-amino-2-(2,6-difluorophenyl)-N-(5-(4-hydroxyazepan-1-yl)isothiazol-4-yl)thiazole-4-carboxamide (49), 2-(2,6-difluorophenyl)-N-(5-(piperidin-4-yloxy)isothiazol-4-yl)thiazole-4-carboxamide (54), N-(5-(azetidin-3-ylmethoxy)isothiazol-4-yl)-2-(2,6-difluorophenyl)thiazole-4-carboxamide (55), 3-amino-N-(5-(azetidin-3-yloxy)isothiazol-4-yl)-6-(2,6-difluorophenyl)picolinamide (56), N-(5-(azetidin-3-yloxy)isothiazol-4-yl)-2-(2,6-difluorophenyl)thiazole-4-carboxamide (57), 6-(2,6-difluorophenyl)-N-(5-(piperidin-4-yloxy) isothiazol-4-yl)-picolinamide (58), 5-amino-N-(5-((4-carbamoylcyclohexyl)oxy)isothiazol-4-yl)-2-(2,6-difluorophenyl)thiazole-4-carboxamide (59), 2-(2,6-difluorophenyl)-N-(5-((3-methyloxetan-3-yl)methoxy)isothiazol-4-yl)thiazole-4-carboxamide (60), 3-amino-N-(5-(3-aminopiperidin-1-yl)isothiazol-4-yl)-6-(2,6-difluorophenyl)-picolinamide (61), 2-(2,6-difluorophenyl)-N-(5-(piperidin-4-ylmethoxy)isothiazol-4-yl)thiazole-4-carboxamide (62), 3-amino-6-(2,6-difluorophenyl)-N-(5-(piperidin-4-ylmethoxy)isothiazol-4-yl)picolinamide (63), (S)-2-(2,6-difluorophenyl)-N-(5-(pyrrolidin-3-yloxy)isothiazol-4-yl)thiazole-4-carboxamide (64), (R)-2-(2,6-difluorophenyl)-N-(5-(pyrrolidin-3-yloxy)isothiazol-4-yl)thiazole-4-carboxamide (65), 5-amino-N-(5-(3-aminopiperidin-1-yl)isothiazol-4-yl)-2-(2,6-difluorophenyl)thiazole-4-carboxamide (66), 2-(2,6-difluorophenyl)-N-(5-(3-hydroxypiperidin-1-yl)isothiazol-4-yl)thiazole-4-carboxamide (67), 5-amino-2-(2,6-difluorophenyl)-N-(5-(3-hydroxypiperidin-1-yl)isothiazol-4-yl)thiazole-4-carboxamide (68), (S)-5-amino-2-(2,6-difluorophenyl)-N-(5-(pyrrolidin-3-yloxy)isothiazol-4-yl)thiazole-4-carboxamide (69), (R)-5-amino-2-(2,6-difluorophenyl)-N-(5-(pyrrolidin-3-yloxy)isothiazol-4-yl)thiazole-4-carboxamide (70), 3-amino-6-(2,6-difluorophenyl)-N-(5-(3-hydroxypiperidin-1-yl)isothiazol-4-yl)picolinamide (71), 6-(2,6-difluorophenyl)-N-(5-(3-hydroxypiperidin-1-yl)isothiazol-4-yl)picolinamide (72), 5-amino-N-(5-(azepan-4-yloxy)isothiazol-4-yl)-2-(2,6-difluorophenyl)thiazole-4-carboxamide (73), 3-amino-6-(2,6-difluorophenyl)-N-(5-(3-hydroxypropoxy)isothiazol-4-yl)picolinamide (74), 5-amino-N-(5-((trans-4-aminocyclohexyl)oxy)isothiazol-4-yl)-2-(2,6-difluorophenyl)thiazole-4-carboxamide (75), 5-amino-2-(2,6-difluorophenyl)-N-(5-(piperidin-4-ylmethoxy)isothiazol-4-yl)thiazole-4-carboxamide (76), 5-amino-N-(5-(4-aminobutoxy)isothiazol-4-yl)-2-(2,6-difluorophenyl)thiazole-4-carboxamide (77), 5-amino-2-(2,6-difluorophenyl)-N-(5-(4-hydroxybutoxy)isothiazol-4-yl)thiazole-4-carboxamide (78), 5-amino-2-(2,6-difluorophenyl)-N-(5-(3-hydroxypropoxy)isothiazol-4-yl)thiazole-4-carboxamide (80), 5-amino-2-(2,6-difluorophenyl)-N-(5-(3-hydroxypropoxy)isothiazol-4-yl)thiazole-4-carboxamide (81), 5-amino-2-(2,6-difluorophenyl)-N-(5-(3-hydroxy-3-methylbutoxy)isothiazol-4-yl)thiazole-4-carboxamide (82), 2-(2,6-difluorophenyl)-5-formamido-N-(5-((4-hydroxy-4-methylpentyl)oxy)isothiazol-4-yl)thiazole-4-carboxamide (83), 5-amino-2-(2,6-difluorophenyl)-N-(5-((4-hydroxypentyl)oxy)isothiazol-4-yl)thiazole-4-carboxamide (84), 2-(2,6-difluorophenyl)-N-(5-((4-hydroxypentyl)oxy)isothiazol-4-yl)thiazole-4-carboxamide (85), 5-amino-2-(2,6-difluorophenyl)-N-(5-((4-hydroxy-4-methylpentyl)oxy)isothiazol-4-yl)thiazole-4-carboxamide (86), 2-(2,6-difluorophenyl)-N-(5-((4-hydroxy-4-methylpentyl)oxy)isothiazol-4-yl)thiazole-4-carboxamide (87), 5-amino-2-(2,6-difluorophenyl)-N-(5-(2-(2,2-dimethyl-1,3-dioxolan-4-yl)ethoxy)isothiazol-4-yl)thiazole-4-carboxamide (88), 5-amino-2-(2,6-difluorophenyl)-N-(5-((2,2-dimethyl-1,3-dioxolan-4-yl)methoxy)isothiazol-4-yl)thiazole-4-carboxamide (89), 5-amino-2-(2,6-difluorophenyl)-N-(5-(3,4-dihydroxybutoxy)isothiazol-4-yl)thiazole-4-carboxamide (91), 2-(2,6-difluorophenyl)-N-(5-(3,4-dihydroxybutoxy)isothiazol-4-yl)thiazole-4-carboxamide (92), 5-amino-N-(5-(3-aminopropoxy)isothiazol-4-yl)-2-(2,6-difluorophenyl)thiazole-4-carboxamide (93), 5-amino-2-(2,6-difluorophenyl)-N-(5-(3-(methylamino)propoxy)isothiazol-4-yl)thiazole-4-carboxamide (94), 5-amino-2-(2,6-difluorophenyl)-N-(5-(4-(methylamino)butoxy)isothiazol-4-yl)thiazole-4-carboxamide (95), or 2-(2,6-difluorophenyl)-N-(5-((4-hydroxy-4-methylpentyl)oxy)isothiazol-4-yl)-5-(methylamino)thiazole-4-carboxamide (96).

7. A method for preparing the compound of claim 1, comprising

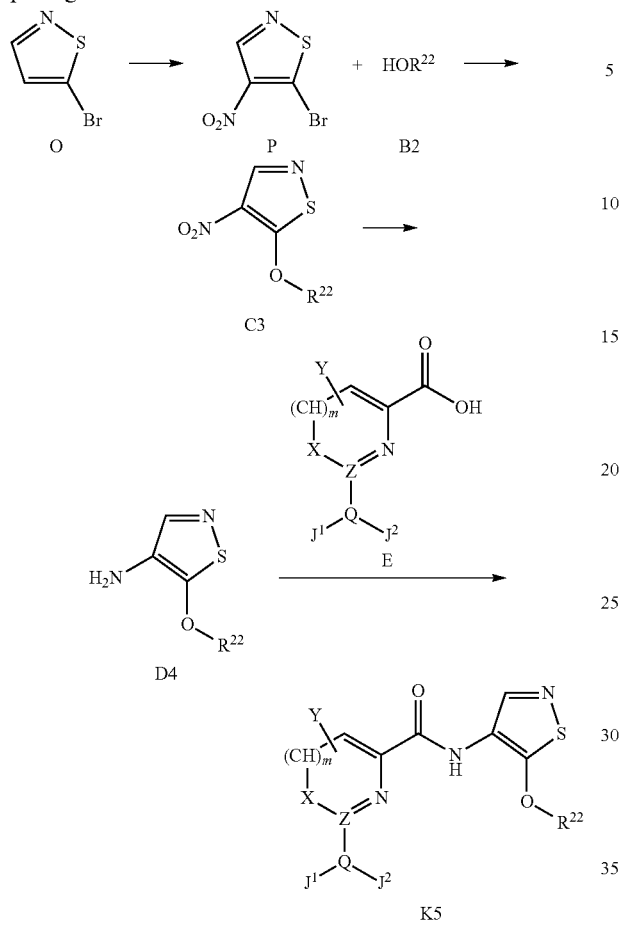

nitrating 5-bromoisothiazole (O) to form 4-nitro-5-bromoisothiazole (P) in a mixed acid having concentrated $H_2SO_4$ and concentrated $HNO_3$ at a ratio of about 3:1, adding a base to a protected or unprotected alcohol (B2) in a first solvent and stirring to form a first mixture, adding the 4-nitro-5-bromoisothiazole (P) to the first mixture, and heating while stirring to form an ether (C3), reacting the ether (C3) with $Na_2S_2O_4$ in a second solvent in presence of a base to form a second mixture, and heating the second mixture to form aminoisothiazole (D4), reacting the aminoisothiazole (D4) with a protected or unprotected carboxylic acid (E) in a third solvent in presence of a coupling reagent and a base at heated condition to form an ether (K5), optionally deprotecting the ether (K5) by treating with a mixture of TFA (trifluoroacetic acid) and dichloromethane at equal volume, and removing solvents to form a final product ether (K5), wherein E is the ether group.

8. A method for preparing the compound of claim 1, comprising

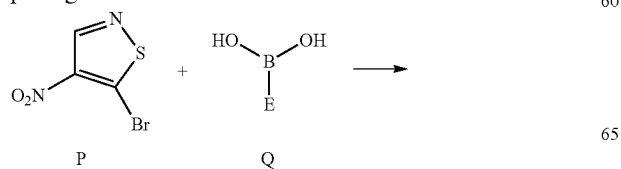

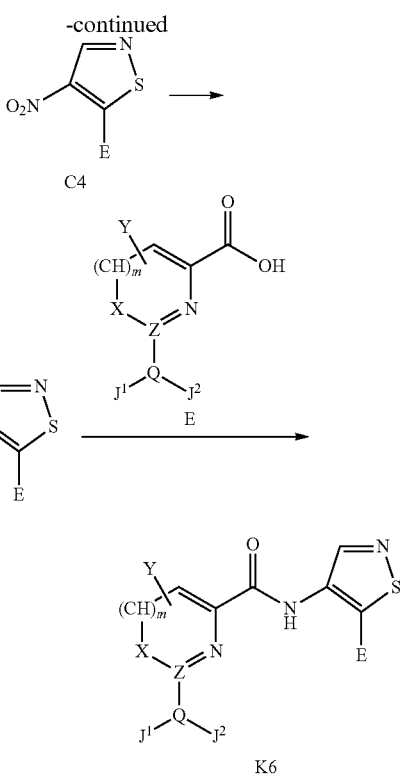

reacting 4-nitro-5-bromoisothiazole (P) with a protected or unprotected boronic acid (Q) in a fourth solvent in presence of a catalyst and a base under heated condition to form a nitroisothiazole intermediate (C4), reacting the nitroisothiazole intermediate C4 with $Na_2S_2O_4$ in a fifth solvent in presence of a base under heated condition to form an aminoisothiazole (D5), reacting a protected or unprotected carboxylic acid (E) with the aminoisothiazole (D5) in a sixth solvent in presence of a coupling reagent and a base at heated conditions to form a biaryl compound (K6), optionally deprotecting the biaryl compound (K6) by treating with a mixture of TFA and dichloromethane at equal volume, and removing solvents in vacuo to obtain a final product of biaryl compound (K6), wherein E is the aromatic or heteroaromatic group in the Formula I.

9. A method for preparing the compound of claim 1, comprising

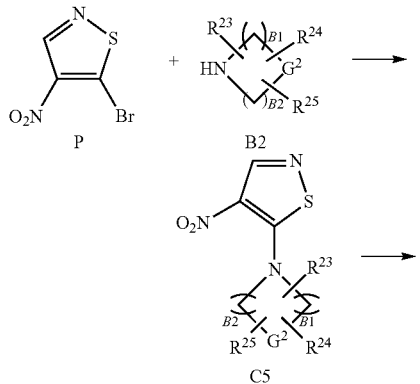

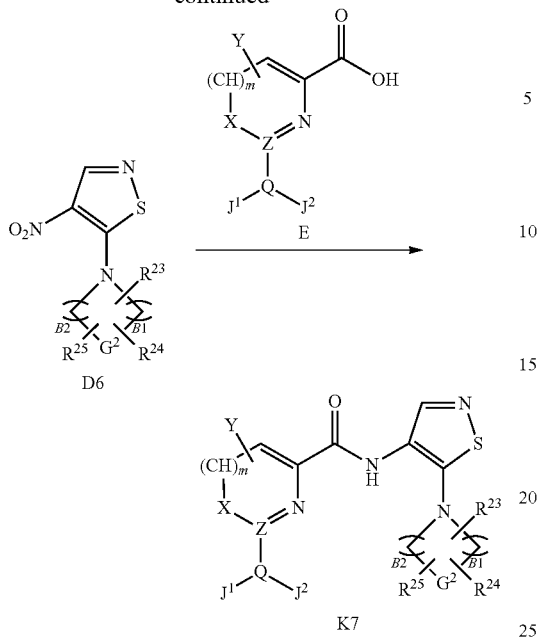

reacting 4-nitro-5-bromoisothiazole (P) with a protected or unprotected secondary amine (B2) in a seventh solvent in presence of a base under heated condition to form a nitroisothiazole intermediate (C5), reacting the nitroisothiazole intermediate (C5) with $Na_2S_2O_4$ in an eighth solvent in presence of a base under heated condition to form aminoisothiazole (D6), reacting a protected or unprotected carboxylic acid (E) with the aminoisothiazole (D6) in a ninth solvent in presence of a coupling reagent and a base at heated condition to form a biaryl compound (K7), optionally deprotecting the biaryl compound (K7) by treating with a mixture of TFA and dichloromethane at equal volume, and removing solvents in vacuo to form a final product biaryl compound (K7), wherein E is the secondary amine group in the Formula I.

10. A pharmaceutical composition comprising the compound of claim 1 as an active pharmaceutical ingredient, and pharmaceutically acceptable carriers and adjuvants.

11. A pharmaceutical composition comprising the Pim kinase inhibitor of claim 5 as an active pharmaceutical ingredient, and pharmaceutically acceptable carriers and adjuvants.

\* \* \* \* \*